United States Patent
Mamada et al.

(10) Patent No.: US 11,322,693 B2
(45) Date of Patent: May 3, 2022

(54) ORGANIC LIGHT-EMITTING ELEMENT, AND LIGHT-EMITTING MATERIAL AND FLUORESCENT BODY USED IN SAME

(71) Applicants: KYUSHU UNIVERSITY, NATIONAL UNIVERSITY CORPORATION, Fukuoka (JP); KYULUX, INC., Fukuoka (JP)

(72) Inventors: Masashi Mamada, Fukuoka (JP); Chihaya Adachi, Fukuoka (JP); Hajime Nakanotani, Fukuoka (JP); YuSeok Yang, Fukuoka (JP)

(73) Assignees: KYUSHU UNIVERSITY NATIONAL UNIVERSITY CORPORATION, Fukuoka (JP); KYULUX, INC., Fukuoka (JP)

( * ) Notice: Subject to any disclaimer, the term of this patent is extended or adjusted under 35 U.S.C. 154(b) by 383 days.

(21) Appl. No.: 16/471,217

(22) PCT Filed: Dec. 20, 2017

(86) PCT No.: PCT/JP2017/045788
§ 371 (c)(1),
(2) Date: Jun. 20, 2019

(87) PCT Pub. No.: WO2018/117179
PCT Pub. Date: Jun. 28, 2018

(65) Prior Publication Data
US 2019/0348617 A1    Nov. 14, 2019

(30) Foreign Application Priority Data
Dec. 20, 2016    (JP) .............................. JP2016-246969

(51) Int. Cl.
| H01L 51/00 | (2006.01) |
| C09K 11/06 | (2006.01) |
| H01L 51/50 | (2006.01) |

(52) U.S. Cl.
CPC .......... H01L 51/0072 (2013.01); C09K 11/06 (2013.01); H01L 51/5004 (2013.01); H01L 51/5016 (2013.01); C09K 2211/1011 (2013.01)

(58) Field of Classification Search
None
See application file for complete search history.

(56) References Cited

U.S. PATENT DOCUMENTS

| 3,838,133 | A | * | 9/1974 | Hall et al. ............ C07D 471/14 546/64 |
| 8,766,249 | B2 | | 7/2014 | Sawada et al. |
| 10,096,786 | B2 | | 10/2018 | Yamada et al. |

FOREIGN PATENT DOCUMENTS

| CN | 103154005 A | 6/2013 |
| CN | 105713045 A | 6/2016 |

(Continued)

OTHER PUBLICATIONS

Lenz et al., Zeitschritft fur Naturforschung, 1994, vol. 49b, pp. 955-957. (Year: 1994).*

(Continued)

*Primary Examiner* — Eli S Mekhlin
(74) *Attorney, Agent, or Firm* — Browdy and Neimark, PLLC

(57) ABSTRACT

Disclosed is an organic light-emitting device using a compound capable of emitting delayed fluorescence and capable of undergoing intramolecular hydron transfer. The compound includes, for example, a compound represented by the (Continued)

general formula. $X^1$ to $X^3$ each represent O or S; $R^1$ to $R^6$ each represent "H or a substituent; n, n1 to n3 each represent an integer of 1 to 3.

5 Claims, 13 Drawing Sheets

(56) References Cited

FOREIGN PATENT DOCUMENTS

| | | |
|---|---|---|
| JP | 2012-523454 A | 10/2012 |
| WO | 2016/012457 A1 | 1/2016 |

OTHER PUBLICATIONS

English language translation of Lenz et al., Zeitschritft fur Naturforschung, 1994, vol. 49b, pp. 955-957. (Year: 1994).*

Ege et al., Tetrahedron Letters, No. 39, pp. 3677-3680 (1977). (Year: 1977).*

Cheney et al., J. Med. Chem., 1983, 26, 729-737 (1983). (Year: 1983).*

Office Action dated Apr. 6, 2021, in corresponding Chinese patent application No. 201780078629.

Gordon, et al., Synthesis of Diquino [2,3-a:2'3'-c]acridine-6,12,18(5H,14H,17H)trione (Triquinolonobenzene), Dyes and Pigments, Jul. 3, 1990, pp. 301-305, vol. 21, No. 27.

Japanese and English version of International Preliminary Report on Patentability of Chapter I/II dated Jun. 25, 2019.

International Search Report and Search Opinion dated Feb. 13, 2018.

Masashi Mamada et al., "Highly-Efficient Thermally Activated Delayed Fluorescence from an Excited-State Intramolecular Proton Transfer System", ACS Central Science, Jul. 7, 2017, 3, 769-777.

Hiroki Uoyama et al., "Highly efficient organic light-emitting diodes from delayed fluorescence", Nature, 2012, 492, 234.

Hiroyuki Tanaka et al., "Efficient green thermally activated delayed fluorescence (TADF) from a phenoxazine-triphenyltriazine (PXZ-TRZ) derivativew", Chem. Commun. 2012, 48, 11392.

Keira Nasu et al., "A highly luminescent spiro-anthracenone-based organic light-emitting diode exhibiting thermally activated delayed fluorescence", Chem. Commun. 2013, 49, 10385.

Qisheng Zhang et al., "Efficient blue organic light-emitting diodes employing thermally activated delayed fluorescence", Nature Photon. 2014, 8, 326.

Ma'rio N. Berberan-Santos et al., "Unusually Strong Delayed Fluorescence of C7", JACS 1996, 118, 9391.

Steven A. Carlson et al., "Delayed Thermal Fluorescence of Anthraquinone in Solutions", JACS 1971, 93, 5611.

Andrzej Maciejewski et al., "Thermally Activated Delayed S1 Fluorescence of Aromatic Thiones", J. Phys. Chem. 1986, 90, 6314.

Ayataka Endo et al, "Thermally Activated Delayed Fluorescence from Sn4þ -Porphyrin Complexes and Their Application to Organic Light-Emitting Diodes—A Novel Mechanism for Electroluminescence", Advanced Material 2009, 21, 4802.

* cited by examiner

[Fig. 1]
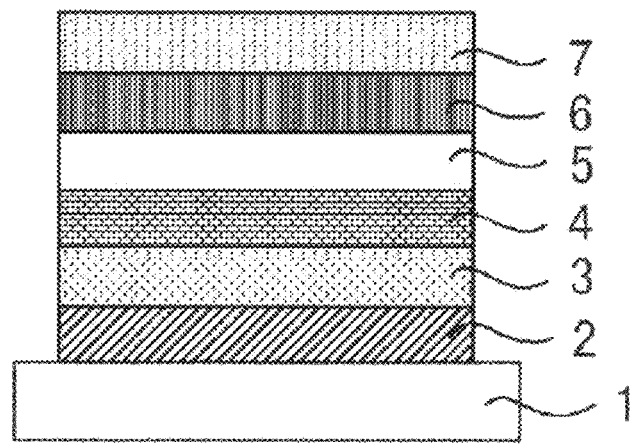
[Fig. 2]
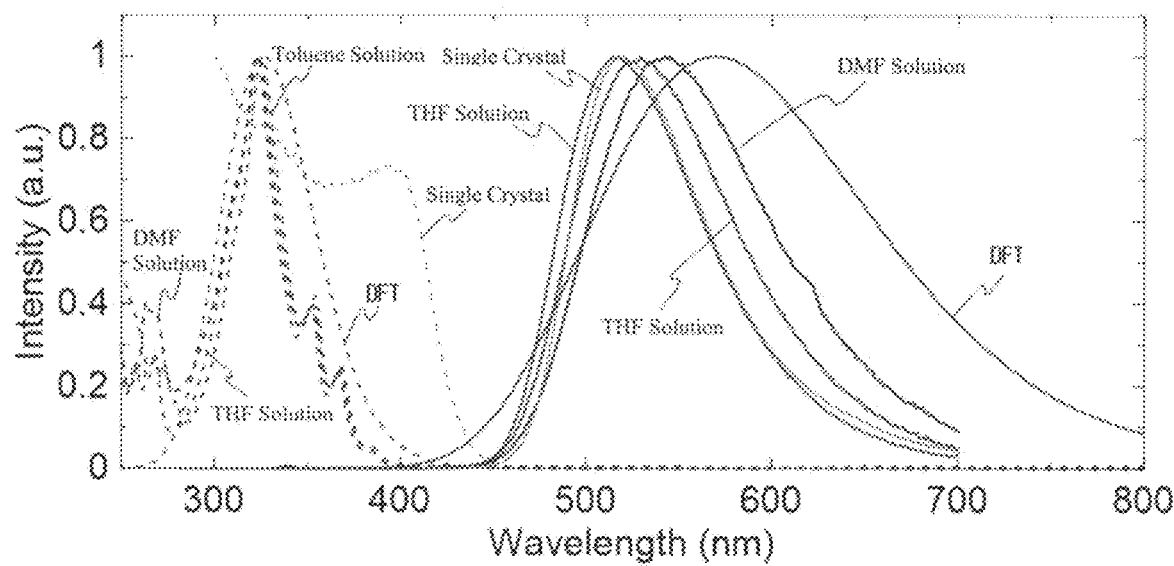

[Fig. 3]
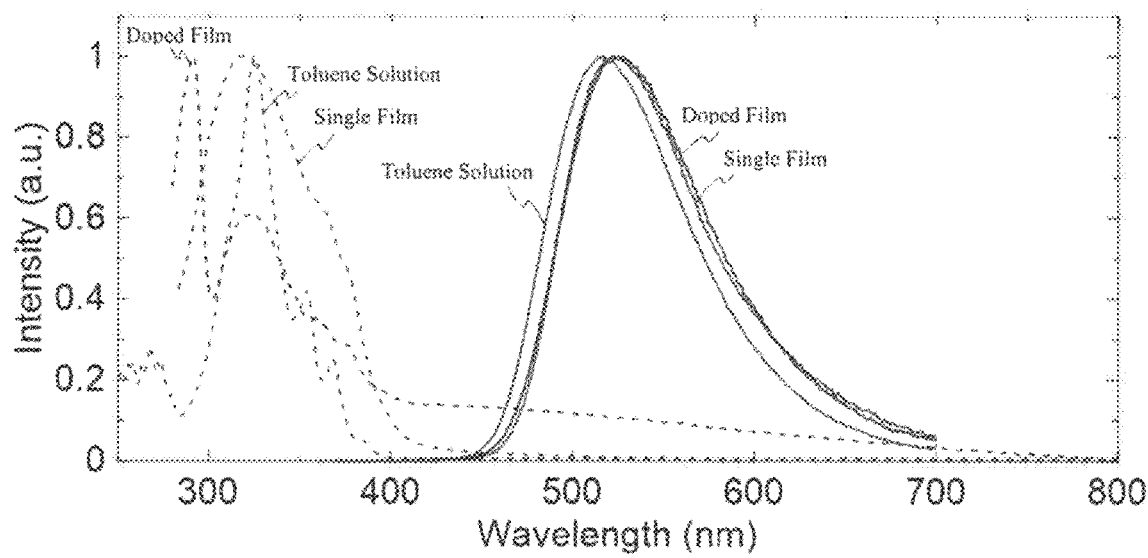
[Fig. 4]
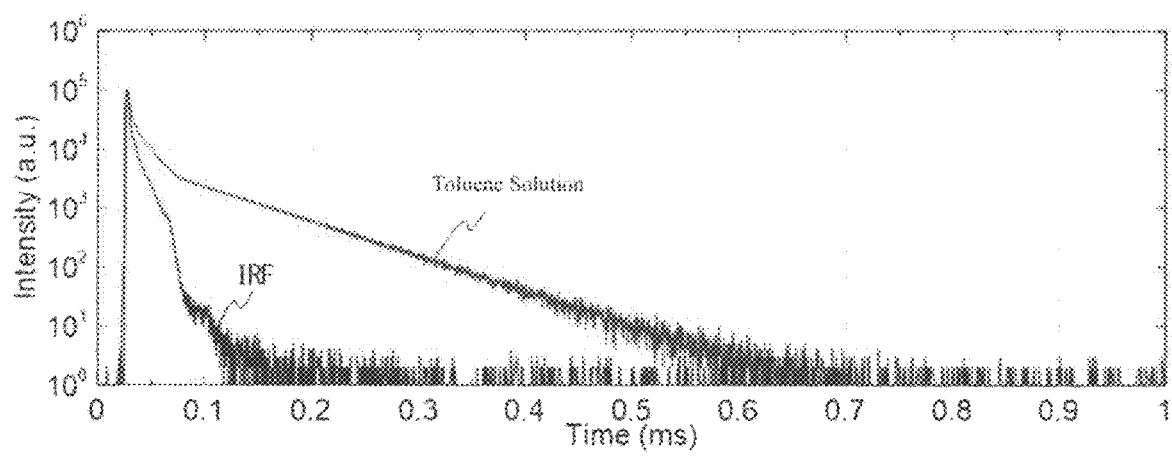

[Fig. 5]
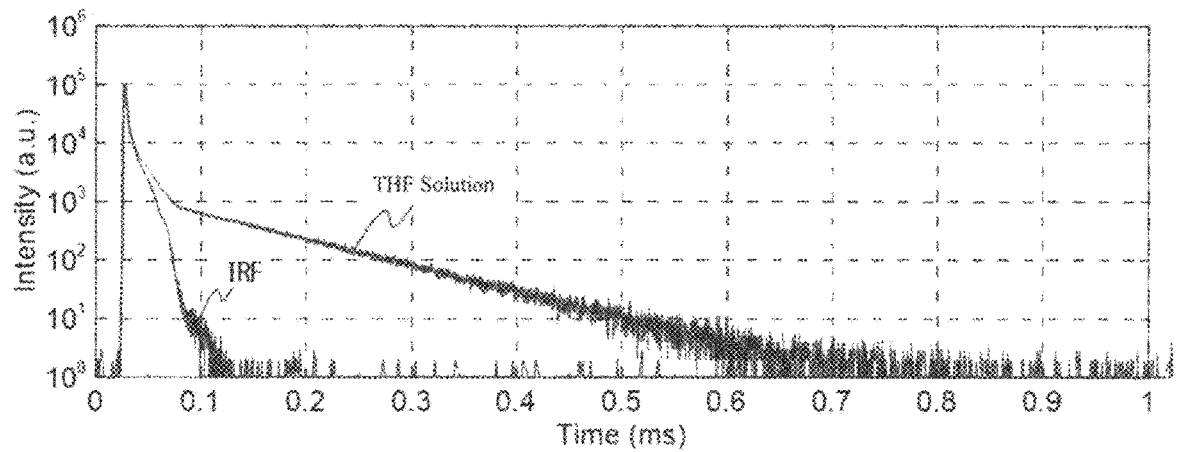
[Fig. 6]
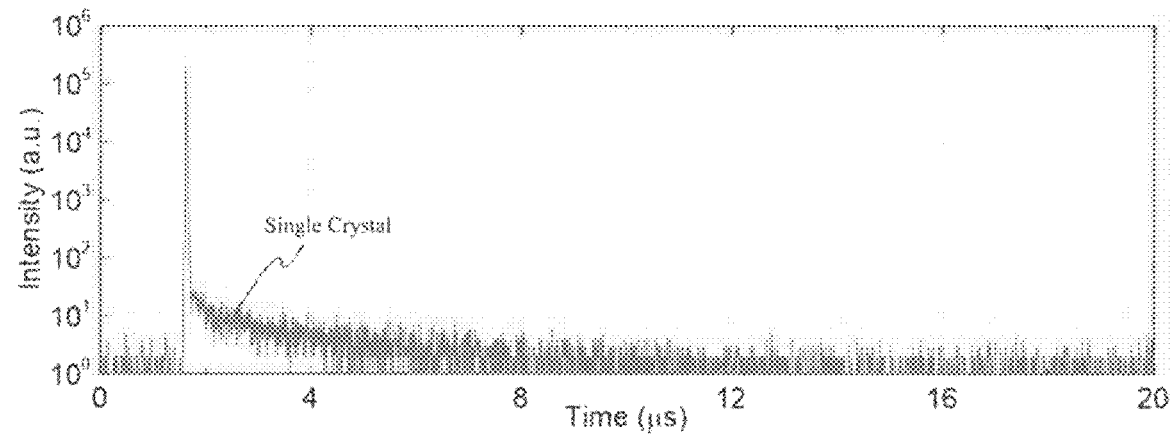

[Fig. 7]
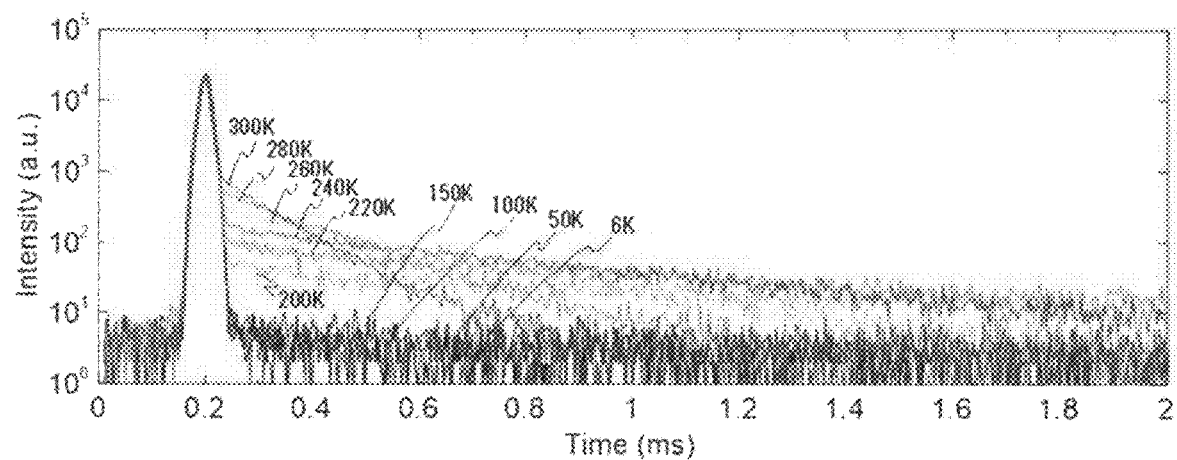
[Fig. 8]
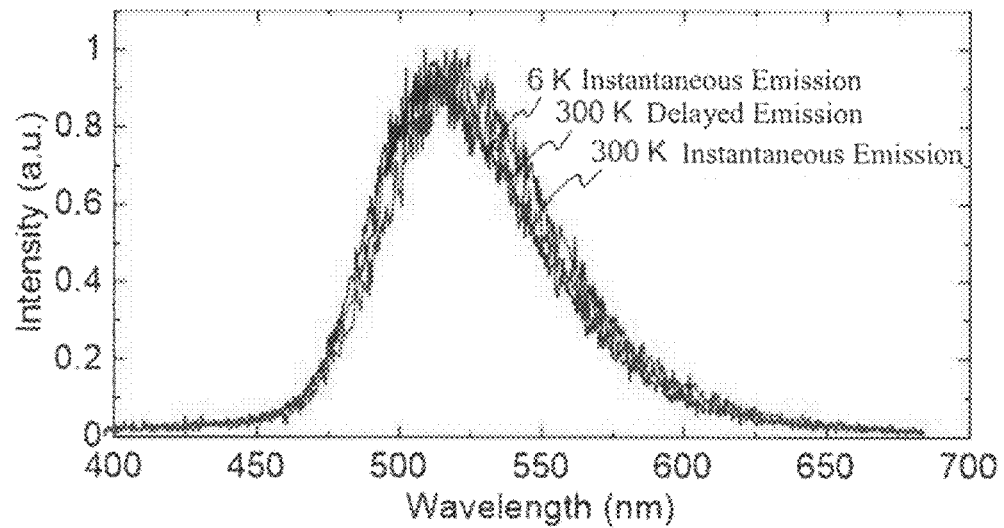

[Fig. 9]
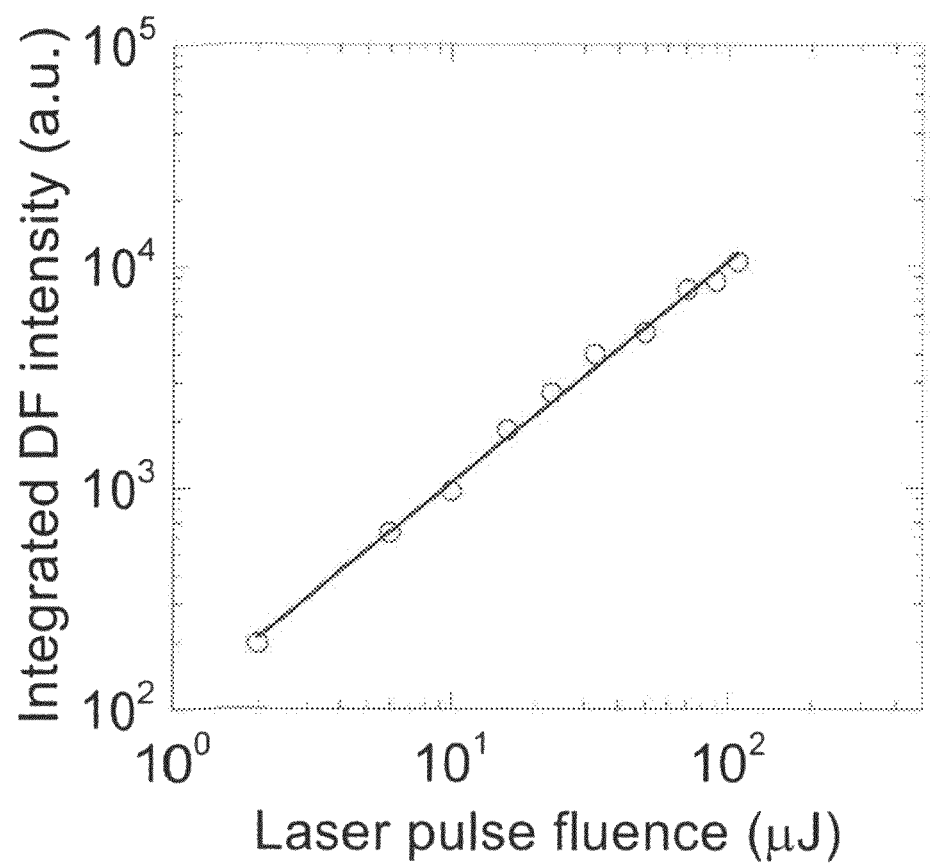

[Fig. 10]
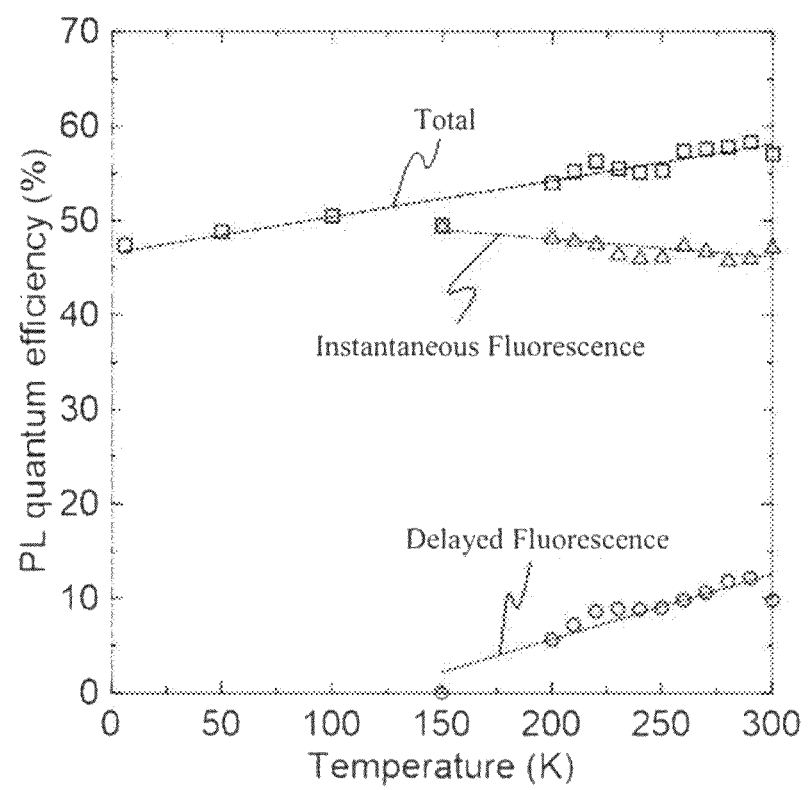

[Fig. 11]
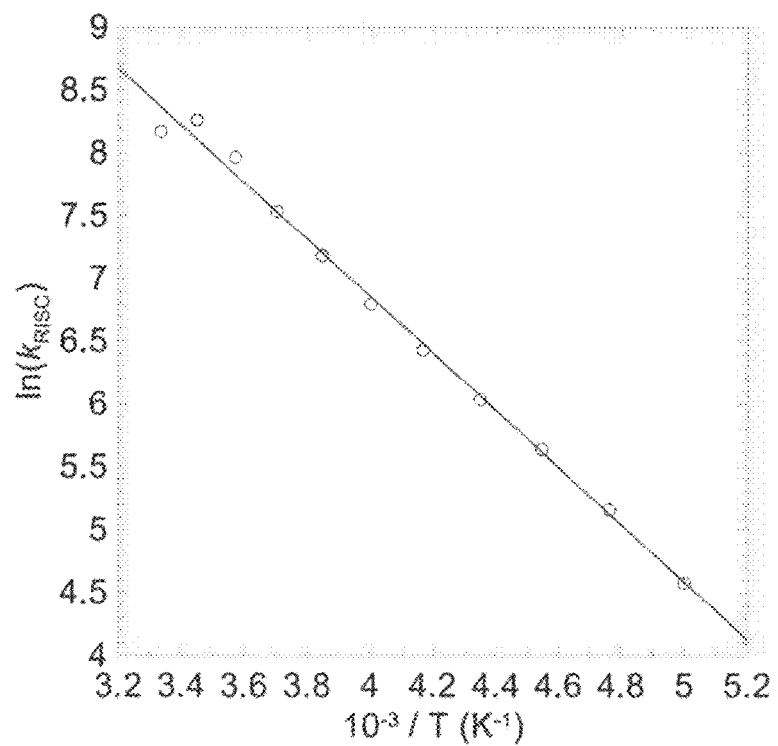
[Fig. 12]
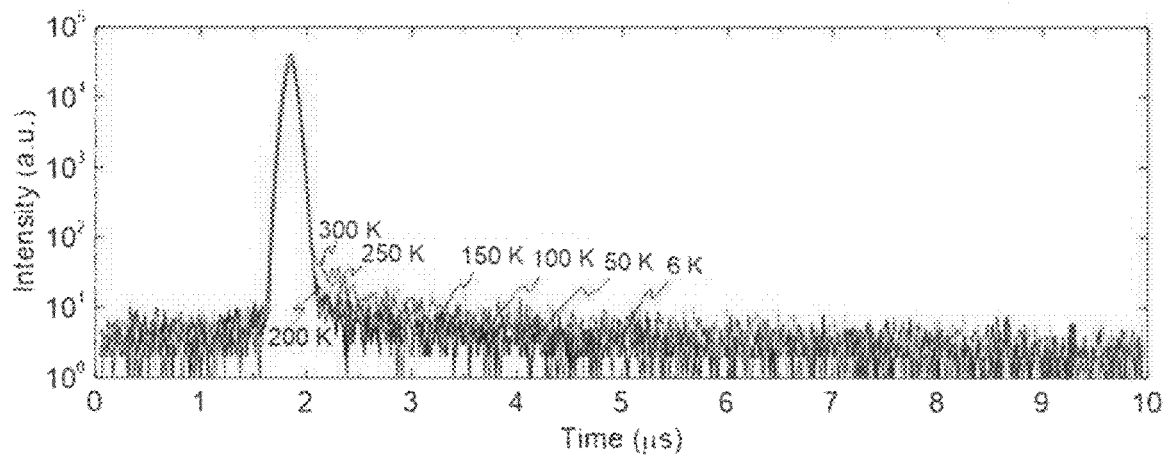

[Fig. 13]
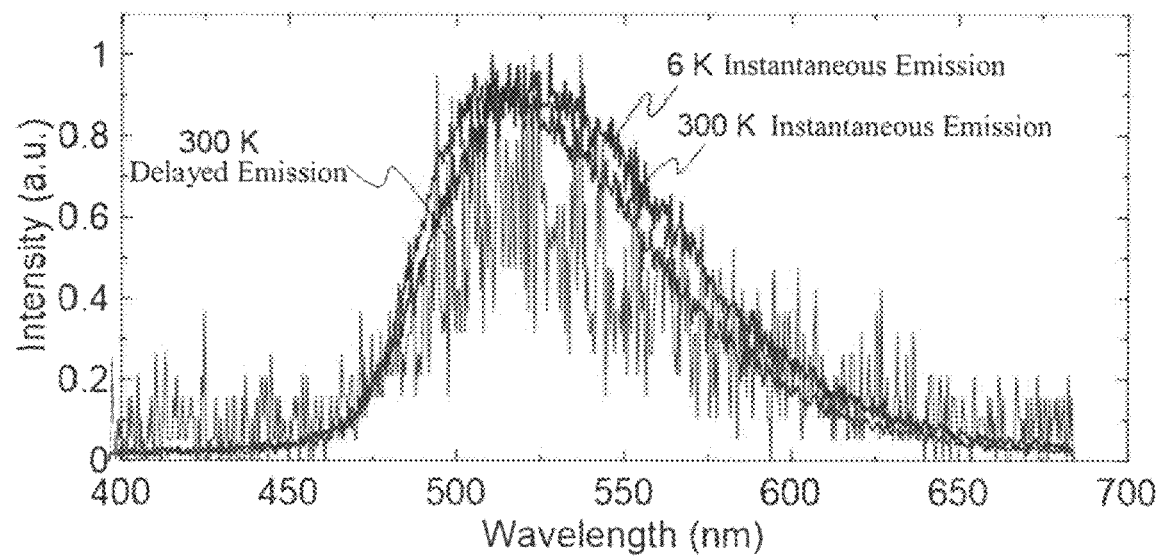
[Fig. 14]
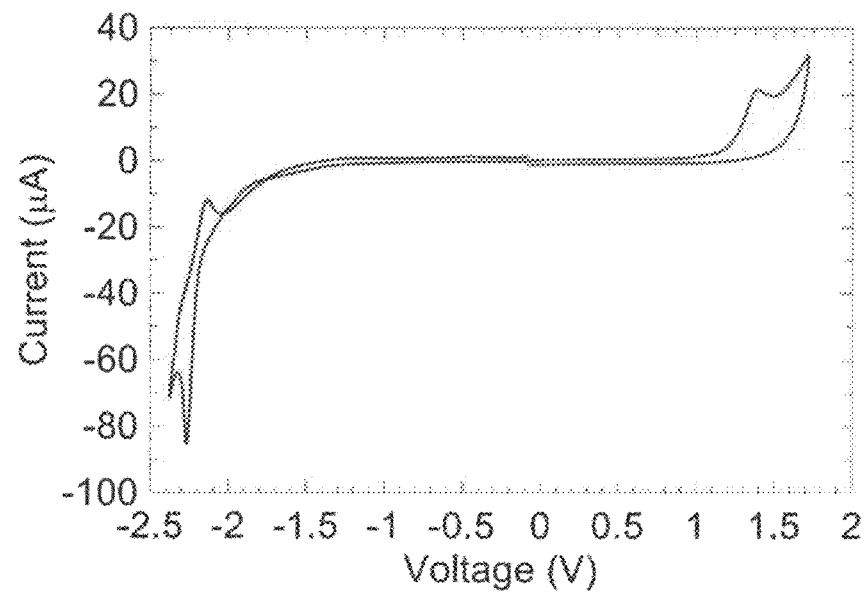

[Fig. 15]
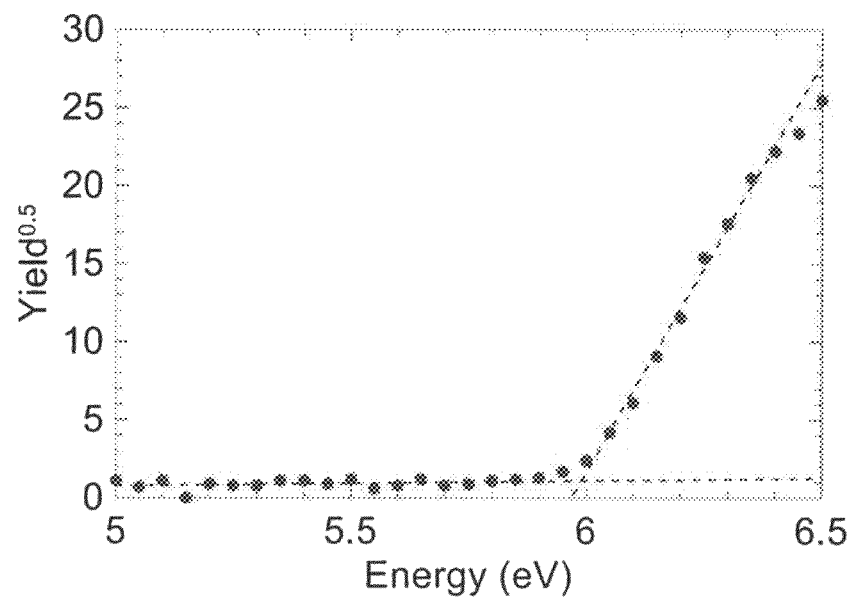
[Fig. 16]
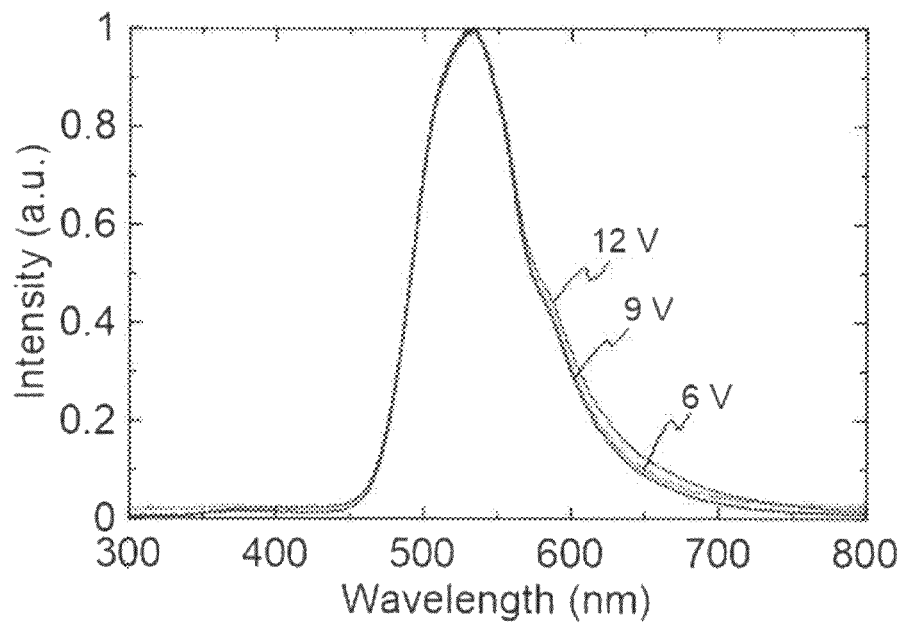

[Fig. 17]
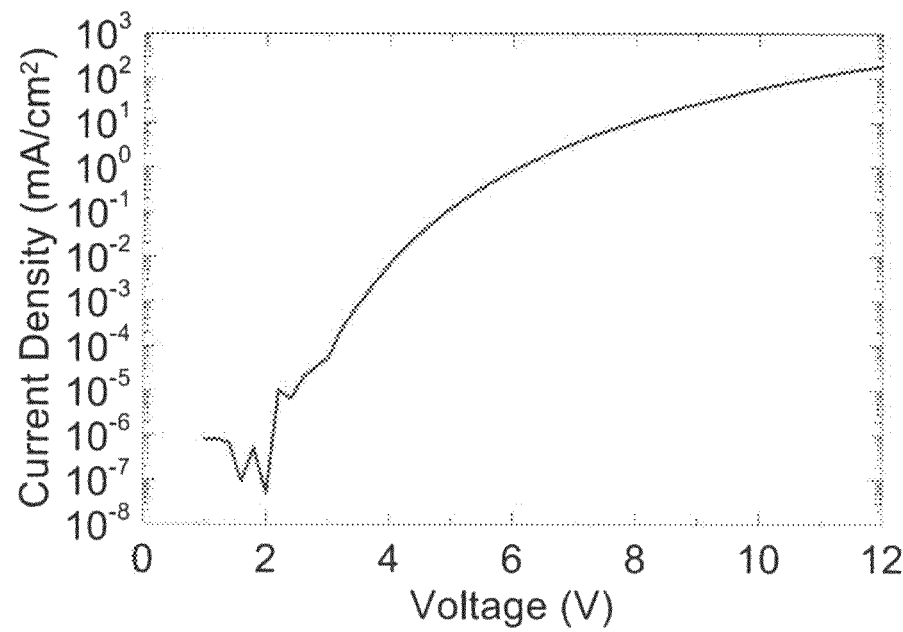
[Fig. 18]
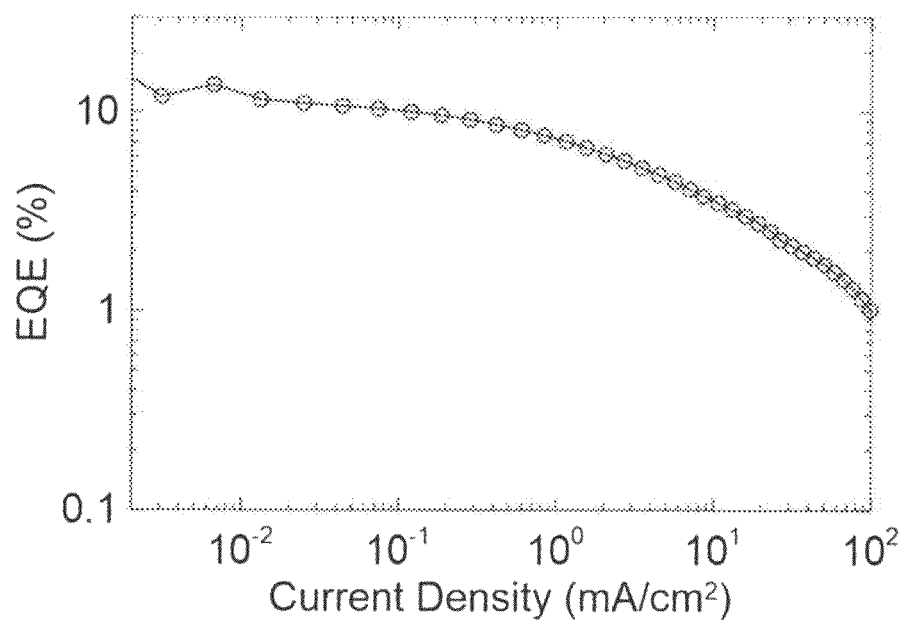

[Fig. 19]
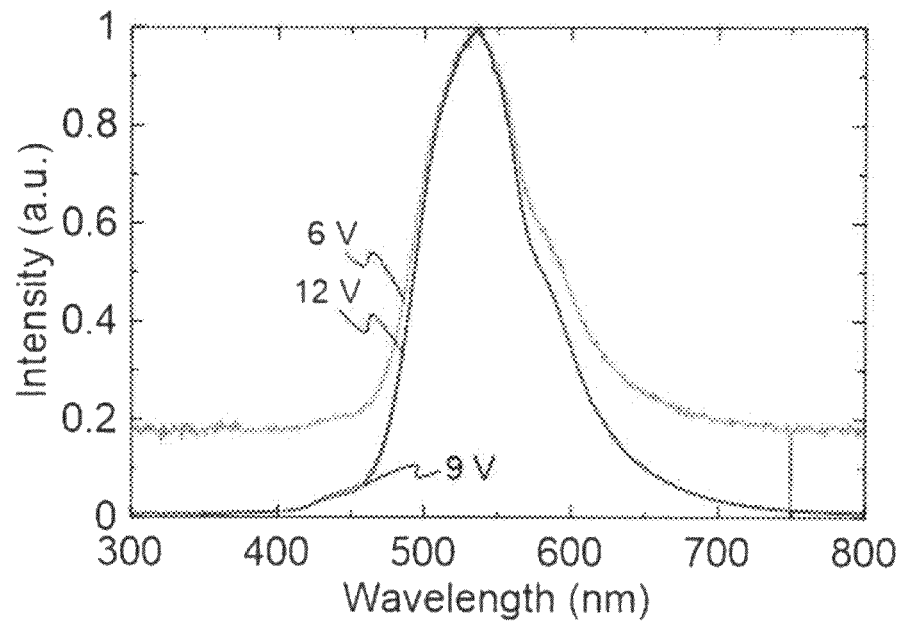
[Fig. 20]
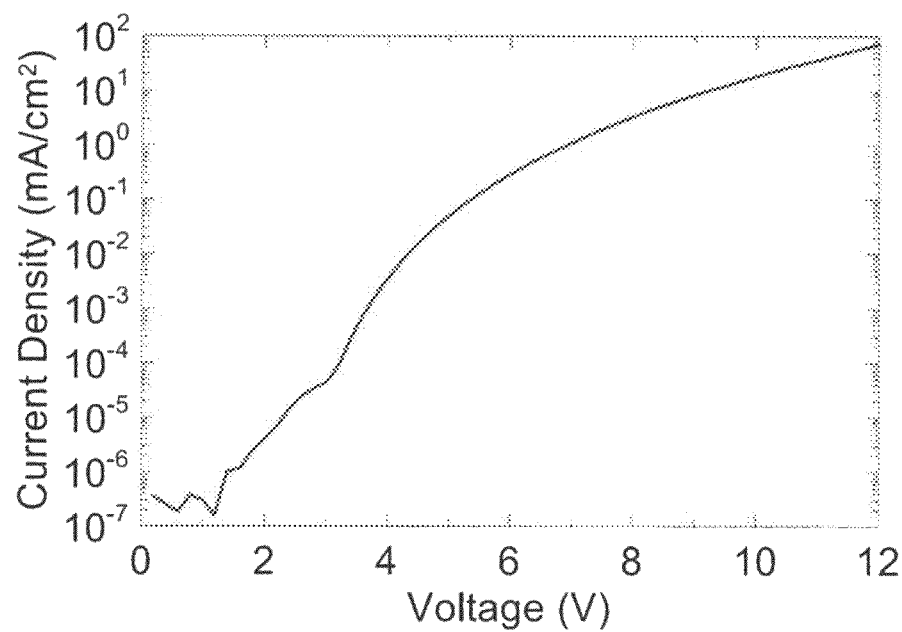

[Fig. 21]
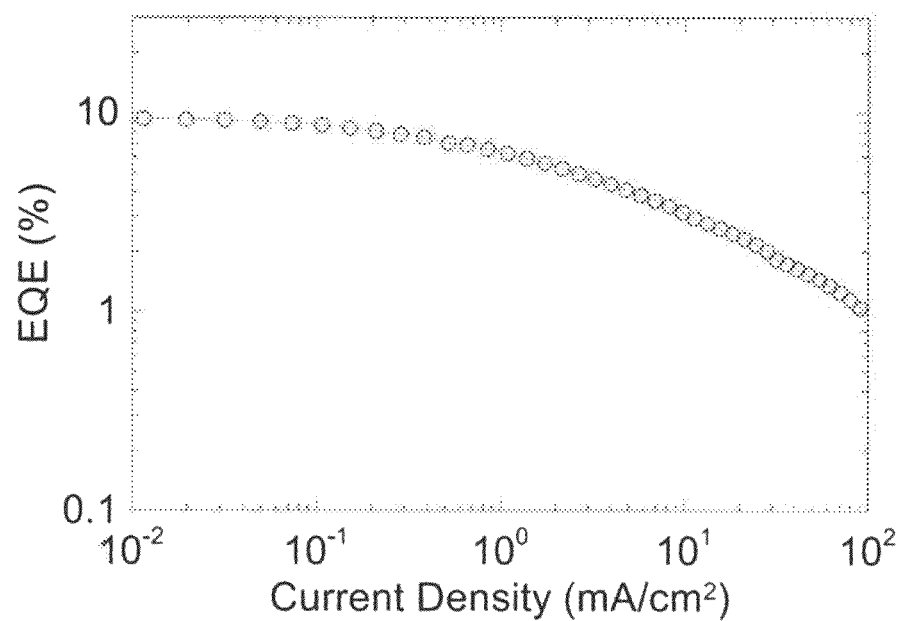
[Fig. 22]
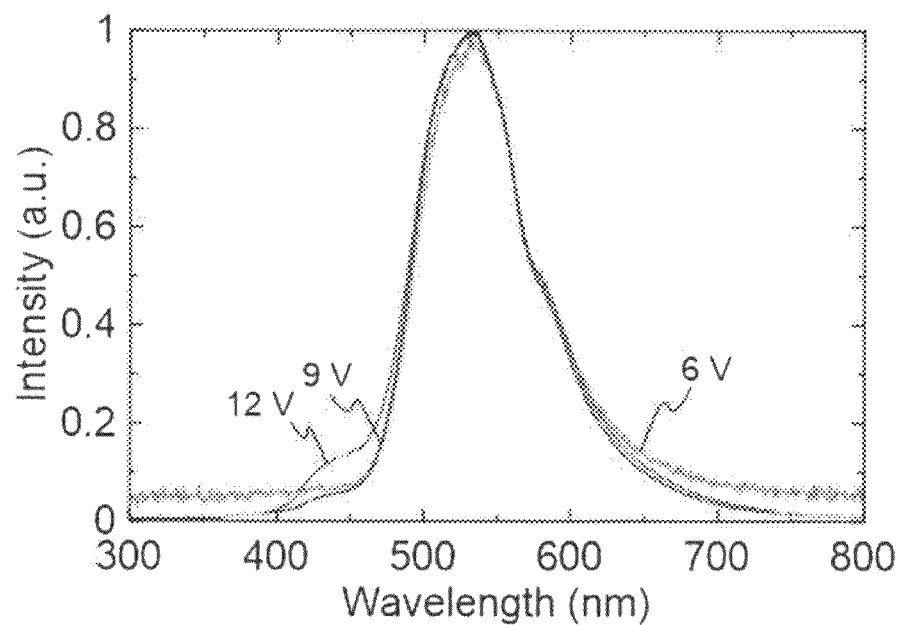

[Fig. 23]
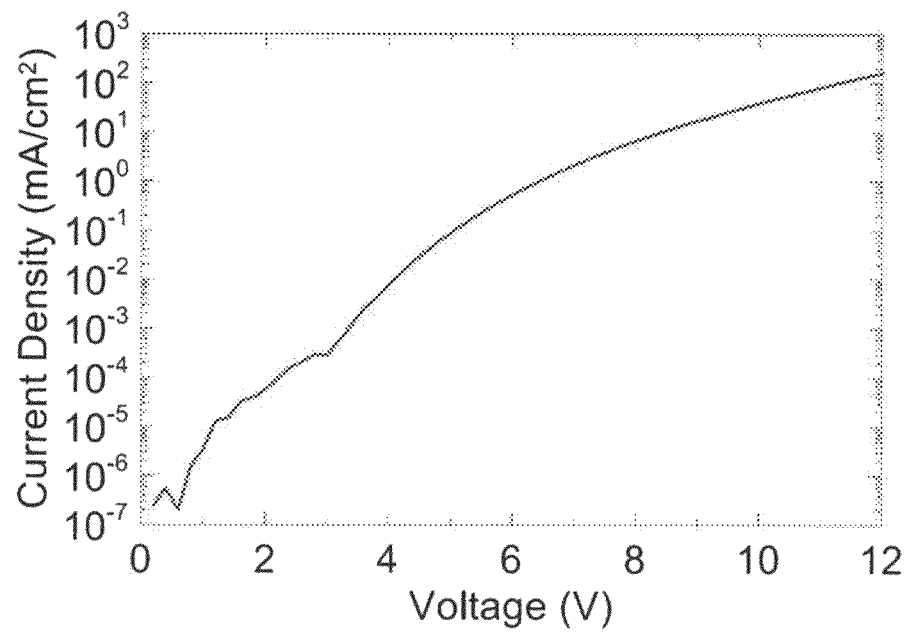
[Fig. 24]
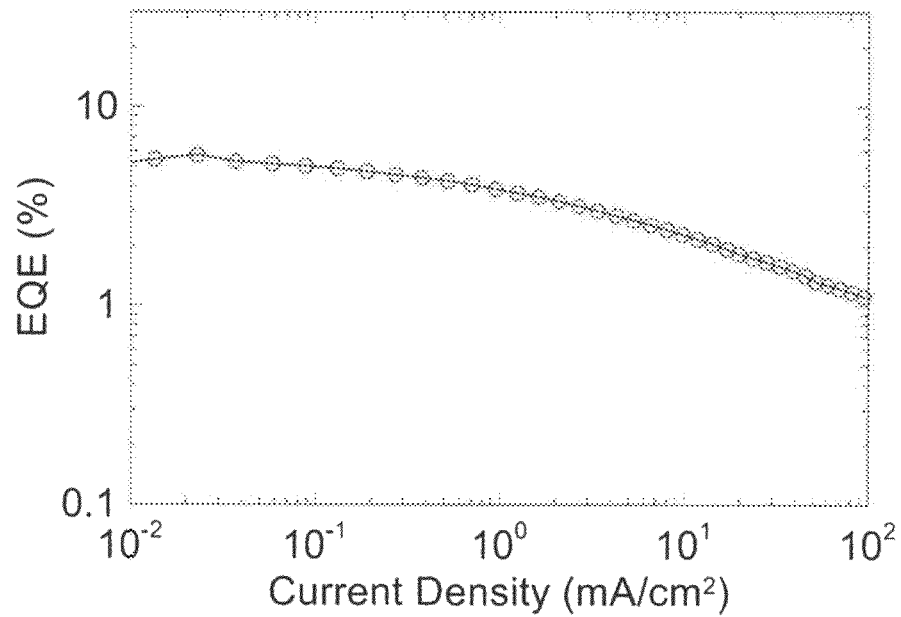

ORGANIC LIGHT-EMITTING ELEMENT, AND LIGHT-EMITTING MATERIAL AND FLUORESCENT BODY USED IN SAME

TECHNICAL FIELD

The present invention relates to an organic light-emitting device using a compound that emits delayed fluorescence.

BACKGROUND ART

Studies for enhancing the light emission efficiency of organic light-emitting devices such as organic electroluminescent devices (organic EL devices) are being made actively. In particular, various kinds of efforts have been made for increasing light emission efficiency by newly developing and combining an electron transfer material, a hole transfer material, a light-emitting material and others to constitute an organic electroluminescent device. Among them, there is known a study relating to an organic electroluminescent device that utilizes a thermal activation type delayed fluorescent material.

A thermal activation type delayed fluorescent material is a compound which, after having transited to an excited triplet state, undergoes reverse intersystem crossing from the excited triplet state to an excited singlet state through absorption of thermal energy, and emits fluorescence when returning back from the excited singlet state to a ground state thereof. Fluorescence through the route is observed later than fluorescence from the excited singlet state directly occurring not via reverse intersystem crossing (ordinary fluorescence), and is therefore referred to as delayed fluorescence. For example, in current excitation of a compound, the occurring probability of the excited singlet state to the excited triplet state is 25%/75%, and therefore improvement of light emission efficiency by the fluorescence alone from the directly occurring excited singlet state is limited. On the other hand, a thermal activation type delayed fluorescent material can effectively utilize also the energy in the excited triplet state occurring in a probability of 75% for fluorescent emission, and can be therefore expected to provide a higher light emission efficiency.

Typical thermal activation type delayed fluorescent materials heretofore known in the art include those having a structure of a donor site (D site) and an acceptor site (A site) bonding to each other in a ground state (D-A type structure), and as specific examples thereof, the following 4 types of compounds are known (NPLs 1 to 4).

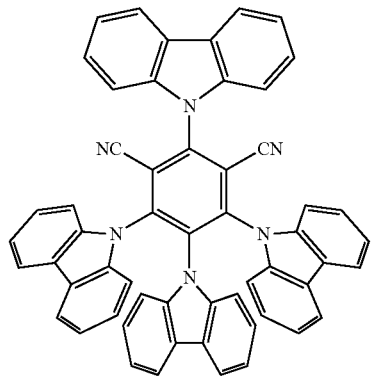

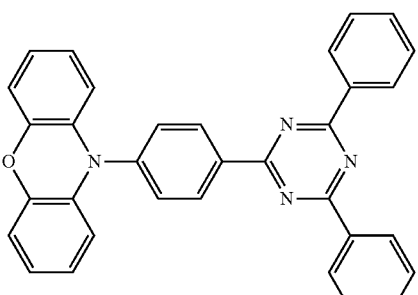

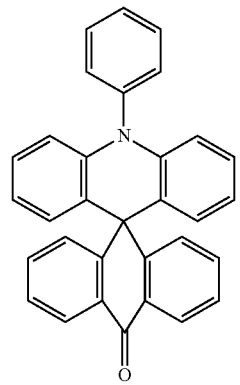

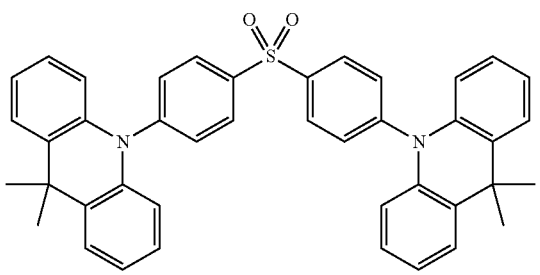

On the other hand, regarding a thermal activation type delayed fluorescent material not containing such a D-A type structure in a ground state, only a few compounds including the following 4 types of compounds are known (NPLs 5 to 8). All these compounds have a low luminescent quantum efficiency, and therefore could not be expected to be applicable to practical use for light-emitting device materials.

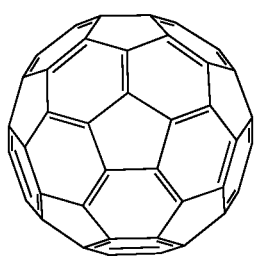

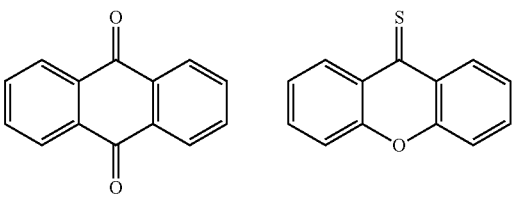

-continued

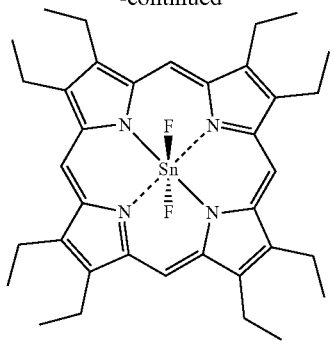

CITATION LIST

Non-Patent Literature

NPL 1: Nature. 2012, 492, 234
NPL 2: Chem. Commun. 2012, 48, 11392
NPL 3: Chem. Commun. 2013, 49, 10385
NPL 4: Nat. Photon. 2014, 8, 326
NPL 5: JACS 1996, 118, 9391
NPL 6: JACS 1971, 93, 5611
NPL 7: J. Phys. Chem. 1986, 90, 6314
NPL 8: Adv. Mater. 2009, 21, 4802

SUMMARY OF INVENTION

Technical Problem

As described above, thermal activation type delayed fluorescent materials not containing a D-A type structure in a ground state that have heretofore been known in the art could not attain a sufficient quantum efficiency. This is considered to be because, in these materials, HOMO (highest occupied molecular orbital) and LUMO (lowest unoccupied molecular orbital) overlap greatly, and therefore owing to the exchange interaction therebetween, the energy level in the excited triplet state where the spin alignment is the same both in HOMO and LUMO is low and the difference $\Delta E_{ST}$ between the lowest excited singlet energy and the lowest excited triplet energy is large, therefore making it difficult to undergo reverse intersystem crossing. Above all, it is considered that, in general, the compounds not containing a D-A type structure in a ground state and having a high planarity could not be excellent thermal activation type delayed fluorescent materials.

Given the situation, the present inventors have made assiduous studies for the purpose of realizing a thermal activation type delayed fluorescent material which, though not containing a D-A type structure in a ground state, can attain a high quantum yield and can be therefore expected to be applicable to practical use as a light-emitting device material, and of providing an organic light-emitting device having a high light emission efficiency that uses the material. Moreover, the present inventors have made further studies for the purpose of developing a thermal activation type delayed fluorescent material having a high planarity to realize such a thermal activation type delayed fluorescent material having high thermochemical stability, high quantum yield and good molecular alignability, thereby providing an organic light-emitting device capable of attaining higher light emission efficiency.

Solution to Problem

As a result of assiduous studies made for the purpose of attaining the above-mentioned objects, the present inventors have found that, among a group of compounds that undergo intramolecular hydron transfer, some compounds can express a property as a delayed fluorescent material through hydron transfer to markedly separate HOMO and LUMO from each other therein. With that, the present inventors have clarified that the compounds capable of undergoing such intramolecular hydron transfer and capable of emitting delayed fluorescence can attain a sufficiently high quantum efficiency enough for practical use even though not having a D-A type structure in a ground state thereof and that, using such a compound, an organic light-emitting device having a high light emission efficiency can be provided. Based on these findings, the present inventors have proposed the present invention, which specifically has the constitution as mentioned below.

[1] An organic light-emitting device using a compound capable of emitting delayed fluorescence and capable of undergoing intramolecular hydron transfer.

[2] The organic light-emitting device according to [1], wherein the compound has 3 or more hydron-transferable sites in the molecule.

[3] The organic light-emitting device according to [1] or [2], wherein the hydron-transferable site is composed of an oxo group and a secondary amino group.

[4] The organic light-emitting device according to [1] or [2], wherein the hydron-transferable site is composed of a carbonyl group and a secondary amino group.

[5] The organic light-emitting device according to any one of [1] to [4], wherein the compound contains a condensed ring structure having 20 or more ring skeleton-constituting atoms.

[6] The organic light-emitting device according to any one of [1] to [4], wherein the compound contains a condensed ring structure having 30 or more ring skeleton-constituting atoms.

[7] The organic light-emitting device according to any one of [1] to [6], wherein the condensed ring structure is a planar structure.

[8] The organic light-emitting device according to any one of [1] to [7], wherein the condensed ring structure contains 3 or more 6-membered rings having a conjugated double bond.

[9] The organic light-emitting device according to [8], wherein the 6-membered rings having a conjugated double bond together form a condensed structure.

[10] The organic light-emitting device according to any one of [4] to [9], wherein the condensed ring structure contains a carbon atom of a carbonyl group and a nitrogen atom of a secondary amino group as the ring skeleton-constituting atoms.

[11] The organic light-emitting device according to any one of [1] to [10], wherein the difference $\Delta E_{ST}$ between the lowest excited singlet energy level $S_1$ and the lowest excited triplet energy level $T_1$ of the compound capable of emitting delayed fluorescence and capable of undergoing intramolecular hydron transfer is 0.3 eV or less.

[12] The organic light-emitting device according to any one of [1] to [11], wherein the rate constant $k_{RISC}$ of reverse intersystem crossing of the compound capable of emitting delayed fluorescence and capable of undergoing intramolecular hydron transfer is $1 \times 10^2$ s$^{-1}$ or more.

[13] The organic light-emitting device according to any one of [1] to [12], wherein the compound capable of emitting delayed fluorescence and capable of undergoing intramolecular hydron transfer is a compound represented by the following general formula (1).

General Formula (1)

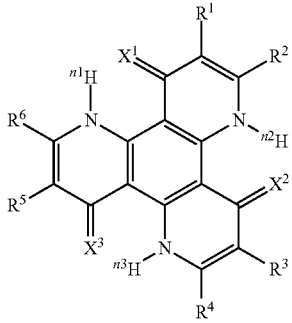

In the general formula (1), $X^1$ to $X^3$ each independently represent O or S. $R^1$ to $R^6$ each independently represent $^n$H or a substituent. n, n1 to n3 each independently represent an integer of 1 to 3. $R^1$ and $R^2$, $R^3$ and $R^4$, $R^5$ and $R^6$ each may bond to each other to form a cyclic structure.

[14] The organic light-emitting device according to [13], wherein $R^1$ and $R^2$, $R^3$ and $R^4$, $R^5$ and $R^6$ in the general formula (1) each bond to each other to form a cyclic structure.

[15] The organic light-emitting device according to any one of [1] to [12], wherein the compound capable of emitting delayed fluorescence and capable of undergoing intramolecular hydron transfer is a compound represented by the following general formula (2).

General Formula (2)

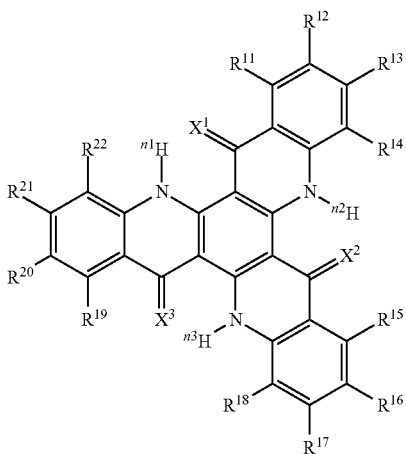

In the general formula (2), $X^1$ to $X^3$ each independently represent O or S. $R^{11}$ to $R^{22}$ each independently represent $^n$H or a substituent. n, n1 to n3 each independently represent an integer of 1 to 3. $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$, $R^{21}$ and $R^{22}$ each may bond to each other to form a cyclic structure.

[16] The organic light-emitting device according to [15], wherein $R^{11}$, $R^{14}$, $R^{15}$, $R^{18}$, $R^{19}$ and $R^{22}$ each are $^n$H.

[17] The organic light-emitting device according to any one of [1] to [16], which has a light-emitting layer containing the compound capable of emitting delayed fluorescence and capable of undergoing intramolecular hydron transfer on a substrate.

[18] The organic light-emitting device according to [17], wherein the light-emitting layer contains a light-emitting material that contains the compound capable of emitting delayed fluorescence and capable of undergoing intramolecular hydron transfer.

[19] The organic light-emitting device according to any one of [1] to [18], wherein the device is an organic electroluminescent device.

[20] The organic light-emitting device according to any one of [1] to [18], wherein the device is an organic light-emitting transistor.

[21] A light-emitting material containing the compound represented by the general formula (1).

[22] A delayed fluorescent material containing the compound represented by the general formula (1).

Advantageous Effects of Invention

In the present invention, a compound capable of emitting delayed fluorescence and capable of undergoing intramolecular hydron transfer is used as a material of an organic light emitting device. The compound capable of emitting delayed fluorescence and capable of undergoing intramolecular hydron transfer exhibits a sufficiently high quantum yield enough for practical use even though not having a D-A type structure in a ground state thereof, and can be effectively used as a delayed fluorescent material for use in a light-emitting device. Consequently, the present invention can realize an organic light-emitting device having a high light emission efficiency and can realize a delayed fluorescent material having a broad latitude in molecular planning of a delayed fluorescent material, having high planarity and having good stability or alignability.

BRIEF DESCRIPTION OF DRAWINGS

FIG. 1 This is a schematic cross-sectional view showing a layer configuration example of an organic electroluminescent device.

FIG. 2 This shows absorption spectra and light emission spectra of a dimethylformamide solution (DMF solution), a tetrahydrofuran solution (THF solution) and a toluene solution (Toluene solution) and a single crystal of a compound 1, and an absorption spectrum and a light emission spectrum obtained through calculation in density functional theory (DFT) of the compound 1.

FIG. 3 This shows absorption spectra and light emission spectra of a single film, a doped film and a toluene solution of the compound 1.

FIG. 4 This shows a transient decay curve in light emission of a toluene solution of the compound 1, measured with nitrogen bubbling.

FIG. 5 This shows a transient decay curve in light emission of a tetrahydrofuran solution of the compound 1, measured with nitrogen bubbling.

FIG. 6 This shows a transient decay curve in light emission of a single crystal of the compound 1.

FIG. 7 This shows a transient decay curve in light emission of a doped film with the compound 1, measured at a temperature of 6 K to 300 K.

FIG. 8 This shows light emission spectra of instantaneous light emission of a doped film with the compound 1 observed at 6 K, instantaneous light emission thereof at 300 K and delayed light emission thereof at 300 K.

FIG. 9 This is a graph of light emission intensity of a doped film with the compound 1 in irradiation with a laser light at a different intensity, as plotted relative to the laser light intensity.

FIG. 10 This is a graph of a photoluminescence quantum efficiency of instantaneous fluorescence, delayed fluorescence and phosphorescence of a doped film with the compound 1 observed under different temperature conditions, as plotted relative to the temperature.

FIG. 11 This is a graph (Arrhenius plot) of a logarithm of the rate constant $k_{RISC}$ of reverse intersystem crossing, as plotted relative to the reciprocal of the absolute temperature.

FIG. 12 This is a transient decay curve in light emission of a single film of the compound 1, measured at a temperature of 6 K to 300 K.

FIG. 13 This shows light emission spectra of instantaneous light emission of a single film of the compound 1 observed at 6 K, instantaneous light emission thereof at 300 K and delayed light emission thereof at 300 K.

FIG. 14 This is a cyclic voltammogram of a thin film of the compound 1, as measured using an Ag/Ag$^+$ electrode and shown as based on ferrocene/ferrocenium (Fc/Fc$^+$).

FIG. 15 This is a graph showing UV irradiation energy dependency of (photoelectric emission yield)$^{0.5}$ of a thin film of the compound 1, measured using a photoelectron spectrometer.

FIG. 16 This shows light emission spectra of an organic electroluminescent device produced in Example 2.

FIG. 17 This is a graph showing a current density-voltage characteristic of an organic electroluminescent device produced in Example 2.

FIG. 18 This is a graph showing an external quantum efficiency (EQE)-current density characteristic of an organic electroluminescent device produced in Example 2.

FIG. 19 This shows light emission spectra of an organic electroluminescent device produced in Example 3.

FIG. 20 This is a graph showing a current density-voltage characteristic of an organic electroluminescent device produced in Example 3.

FIG. 21 This is a graph showing an external quantum efficiency (EQE)-current density characteristic of an organic electroluminescent device produced in Example 3.

FIG. 22 This shows light emission spectra of an organic electroluminescent device produced in Example 4.

FIG. 23 This is a graph showing a current density-voltage characteristic of an organic electroluminescent device produced in Example 4.

FIG. 24 This is a graph showing an external quantum efficiency (EQE)-current density characteristic of an organic electroluminescent device produced in Example 4.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description, a numerical value range expressed using "A to B" denotes a range including numerical values before and after "to" as a minimum value and a maximum value, respectively.

In the present invention, a compound capable of emitting delayed fluorescence and capable of undergoing intramolecular hydron transfer is used as a material for the organic light-emitting device. In the following, the compound for use in the organic light-emitting device of the present invention is described.

[Compound Capable of Emitting Delayed Fluorescence and Capable of Undergoing Intramolecular Hydron Transfer]

The compound for use in the organic light-emitting device of the present invention is a compound capable of emitting delayed fluorescence and capable of undergoing intramolecular hydron transfer.

"Delayed fluorescence" in the present invention means fluorescence which a compound having been in an excited state after given energy emits after the compound has undergone reverse intersystem crossing from an excited triplet state to an excited singlet state and when it returns back from the excited singlet state to a ground state. In general, fluorescence emitted via reverse intersystem crossing is observed later than fluorescence (instantaneous fluorescence) from the excited singlet state that has occurred not via reverse intersystem crossing. In the present invention, a compound that emits fluorescence having an emission lifetime of 50 ns or more is referred to as a compound that "emits delayed fluorescence".

"Intramolecular hydron transfer" in the present invention means that an $^n$H bonding to one atom that constitutes a compound bonds to any other atom positioning around it after the bond to that one atom has cut or along with change in the bonding mode to that atom, or means that, in the case where an $^n$H bonds both to one atom constituting the compound and to any other atom, the bonding between that $^n$H and that one atom is cut, or the bonding mode between that $^n$H and that one atom changes to thereby change the bonding mode between that $^n$H and the other atom. The bonding mode between one atom and an $^n$H, or between any other atom and an $^n$H includes a covalent bond and a hydrogen bond. In one example of intramolecular hydron transfer, an $^n$H bonding to one atom via a covalent bond bonds to any other atom via a covalent bond, after the covalent bond of that $^n$H to that one atom is cut. An $^n$H bonding to one atom via a covalent bond before intramolecular hydron transfer may bond to any other atom via a hydrogen bond, and the $^n$H having bonded to the other atom via a covalent bond through intramolecular hydron transfer may bond to that one atom having covalent-bonded before the intramolecular hydron transfer, via a hydrogen bond. The atom (one atom) to which an $^n$H bonds before intramolecular hydron transfer, and the atom to which an $^n$H transfers (the other atom) are not specifically limited, but for example, they may be an atom having a high electronegativity, concretely including a nitrogen atom, an oxygen atom, a sulfur atom, and a fluorine atom. The inducing factor for intramolecular hydron transfer includes, though not specifically limited thereto, light irradiation and injected carrier recombination, and a phenomenon of a compound in an excited state to cause intramolecular hydron transfer is known as excited-state intramolecular proton-transfer (ESIPT).

"$^n$H" in the present invention is a concept to include isotopes of hydrogen atom. n is 1, 2 or 3, and n is preferably 1 or 2. When n is 1, $^n$H represents a light hydrogen atom (H) in which the atomic nucleus is composed of one proton; when n is 2, $^n$H represents a deuterium atom (D) in which the atomic nucleus is composed of one proton and one neutron; and when n is 3, $^n$H represents a tritium atom (T) in which the atomic nucleus is composed of one proton and 2 neutrons.

"Hydron" in the present invention is a concept including isotopes of hydrogen cation ($^n$H$^+$). n is 1, 2 or 3, and n is preferably 1 or 2. When n is 1, hydron represents a proton (H$^+$) composed of one proton; when n is 2, hydron represents a deuteron (D$^+$) composed of one proton and one neutron; and when n is 3, hydron represents triton (T$^+$) composed of one proton and 2 neutrons.

A compound that can undergo intramolecular hydron transfer can be identified by (1) the Stokes shift in the absorption-emission spectrum thereof is more than 100 nm, (2) the conformation thereof can form an intramolecular hydrogen bond, or (3) the hydron transfer process thereof is extremely rapid as compared with the radiative process, and the hydron transfer occurs in the compound within an order of picosecond.

A compound capable of emitting delayed fluorescence and capable of undergoing intramolecular hydron transfer as mentioned above exhibits a sufficiently high quantum yield enough for practical use even though not having a D-A type structure or a twisted structure in the ground state thereof, and can be effectively used as a delayed fluorescent material applicable to light-emitting devices. Consequently, according to the present invention, an organic light-emitting device having a high emission efficiency can be realized, and a delayed fluorescent material having a broad latitude in molecular planning of a delayed fluorescent material, having high planarity and having good stability or alignability can be realized. Using a delayed fluorescent material having such good alignability, the emission efficiency of an organic light-emitting device can be increased. The reason why a compound capable of emitting delayed fluorescence and capable of undergoing intramolecular hydron transfer can have a high quantum yield is presumed to be because of the following mechanism.

Specifically, for obtaining a high quantum yield by making a compound emit delayed fluorescence, the difference $\Delta E_{ST}$ between the lowest excited singlet energy level $S_1$ and the lowest excited triplet energy level $T_1$ of the compound must be small so as to facilitate reverse intersystem crossing from the excited triplet state to the excited singlet state in the compound. Therefore, already-existing delayed fluorescent materials are so designed that the molecule thereof in a ground state is made to have a D-A type structure or a twisted structure to thereby spatially separate HOMO (highest occupied molecular orbital) and LUMO (lowest unoccupied molecular orbital) from each other and to reduce the exchange interaction therebetween so as to thereby reduce $\Delta E_{ST}$.

As opposed to the above, a compound capable of emitting delayed fluorescence and capable of undergoing intramolecular hydron transfer can be in an excited state as given energy through light irradiation or injected carrier recombination to induce hydron transfer, even though HOMO and LUMO are distributed unbiasedly in a state before intramolecular hydron transfer, and therefore the electron condition around the hydron transferred site changes locally. As a result, it is considered that HOMO and LUMO may markedly separate from each other to reduce $\Delta E_{ST}$. Consequently, the compound of the type can efficiently emit delayed fluorescence even though not having a D-A type structure or a twisted structure in a ground state, and can attain a high quantum yield.

The number of the hydron-transferable sites existing in the molecule of the compound may be 1 or more, and is, for example, preferably 3 or more. Here, the "hydron-transferable site" means a combination of an atomic group containing an ″H and an atom or an atomic group to which that ″H transfers, and for example, a combination of a secondary amino group (—N″HR), a hydroxyl group (—O″H) or a thiol group (—S″H), and a group containing an oxo group (═O) or a thioxo group (═S). Specific examples thereof include a combination of a secondary amino group (—N″HR) and a carbonyl group [—C(═O)—], a combination of a hydroxy group (—O″H) and a carbonyl group [—C(═O)—], a combination of a hydroxy group (—O″H) and a thiocarbonyl group [—C(═S)—], a combination of a hydroxy group (—O″H) and an aldehyde group (—C″HO), a combination of a hydroxy group (—O″H) and a hetero ring nitrogen atom (pyridine-type nitrogen), and a combination of a secondary amino group (—N″HR) and a hetero ring nitrogen atom (pyridine-type nitrogen). Above all, preferably, the "hydron-transferable site" is composed of a combination of a secondary amino group and a carbonyl group. In the combination of a secondary amino group and a carbonyl group, ″H leaves from the nitrogen atom of the secondary amino group (—N″HR) and bonds to the oxygen atom of the carbonyl group [—C(═O)—], and the nitrogen atom from which ″H has left forms an imino structure (—N═R), and the oxygen atom having bonded to ″H forms a hydroxy group (—O″H) along with the ″H, thereby attaining hydron transfer. Here, R in the above-mentioned —N″HR and —N═R represents a substituent, which may bond to the atomic group to which —N″HR or —N═R bonds to thereby form a cyclic structure. Of the hydron-transferable sites, all or a part may actually undergo hydron transfer in an excited state. In the case where the number of hydron-transferable sites existing in the molecule is 2 or more, the plural hydron-transferable sites may be the same or different.

Preferably, the compound capable of emitting delayed fluorescence and capable of undergoing intramolecular hydron transfer for use in the present invention contains a condensed ring structure, more preferably contains a condensed ring structure having 20 or more ring skeleton-constituting atoms, and even more preferably contains a condensed ring structure having 30 or more ring skeleton-constituting atoms. Also preferably, the condensed ring structure that the compound contains is a planar structure, and preferably contains a carbon atom of a carbonyl group and a nitrogen atom of a secondary amino group as the ring skeleton-constituting atoms. Here, the "planar structure" means that all the carbon atoms constituting the condensed ring structure have an sp2 hybrid orbital. Among them, those where the entire molecule also has a planar structure are preferred. A structure that the entire molecule has a planar structure means that all the atoms except ″H that constitute the molecule can configure in one plane. When the compound has a planar structure, the molecular alignability increases to further increase the emission efficiency of the organic light-emitting device using the compound. In addition, also preferably, the condensed ring structure that the compound contains can contain 3 or more 6-membered rings having a conjugated double bond, in which, preferably, the 6-membered rings do not together form a condensed structure. In the case where the condense ring structure contains a benzene ring as a 6-membered ring having a conjugated double bond, preferably, two carbon atoms of one benzene ring bond to the two carbon atoms of the other benzene ring each via a divalent linking group, in which, preferably, hydron transfer occurs between the linking groups. Further, the condensed ring structure that the compound contains preferably has a rotationally symmetrical structure, more preferably a threefold symmetrical structure.

The compound capable of emitting delayed fluorescence and capable of undergoing intramolecular hydron transfer for use in the present invention is preferably such that the difference $\Delta E_{ST}$ between the lowest excited singlet energy level $S_1$ and the lowest excited triplet energy level $T_1$ thereof is 0.3 eV or less, more preferably 0.25 eV or less, even more preferably 0.2 eV or less, still more preferably 0.15 eV or less, and especially preferably 0.1 eV or less. The compound capable of emitting delayed fluorescence and capable of undergoing intramolecular hydron transfer is also preferably such that the rate constant $k_{RISC}$ of reverse intersystem crossing thereof from the lowest excited triplet state to the lowest excited single state is $1 \times 10^2$ s$^{-1}$ or more, more preferably $1 \times 10^3$ s$^{-1}$ or more, even more preferably $3 \times 10^3$ s$^{-1}$ or more, still more preferably $1 \times 10^4$ s$^{-1}$ or more, and especially preferably $1 \times 10^5$ s$^{-1}$ or more. The compound of the type can efficiently emit delayed fluorescence and can attain a high quantum yield. Here, $\Delta E_{ST}$ and $k_{RISC}$ of the compound can be calculated through measurement of the emission lifetime of instantaneous fluorescence and delayed fluorescence thereof. Regarding the concrete measurement methods and measurement conditions, the section of Examples to be given hereinunder is referred to.

The compound capable of emitting delayed fluorescence and capable of undergoing intramolecular hydron transfer for use in the present invention has relatively high thermochemical stability. The glass transition temperature (Tg) of the compound is preferably 80° C. or higher, more preferably 130° C. or higher, even more preferably 180° C. or higher. When a compound having high thermochemical stability is used, degradation of devices (lifetime reduction) to be caused by compound degradation can be prevented. In addition, production of devices be attained at a high temperature, and therefore the latitude in device planning can be broadened and the industrial applicability of the invention can be thereby increased.

The compound for use in the present invention is preferably a compound represented by the following general formula (1).

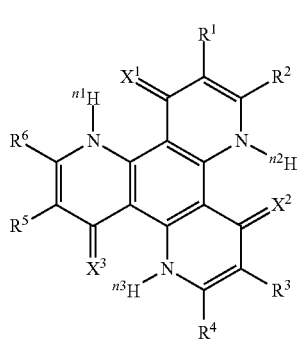

General Formula (1)

In the general formula (1), $X^1$ to $X^3$ each independently represent O or S. $R^1$ to $R^6$ each independently represent "H or a substituent. n, n1 to n3 each independently represent an integer of 1 to 3, preferably 1 or 2. $R^1$ and $R^2$, $R^3$ and $R^4$, $R^5$ and $R^6$ each may bond to each other to form a cyclic structure. In the case where two or more of $R^1$ to $R^6$ each are a substituent, plural substituents may be the same or different.

Preferably, the compound represented by the general formula (1) includes a compound represented by the following general formula (2).

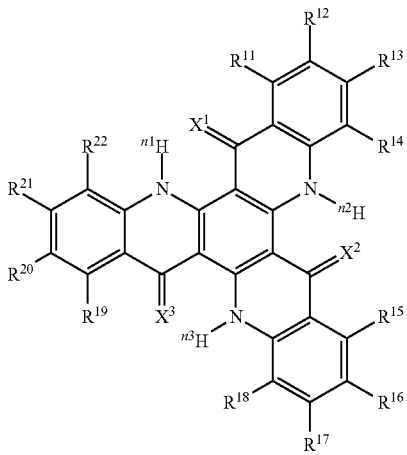

General Formula (2)

In the general formula (2), $X^1$ to $X^3$ each independently represent O or S. $R^{11}$ to $R^{22}$ each independently represent "H or a substituent. The number of the substituents is not specifically limited, and all of $R^{11}$ to $R^{22}$ may be unsubstituted (that is, "H). Of $R^{11}$ to $R^{22}$, preferably, $R^{11}$, $R^{14}$, $R^{15}$, $R^{18}$, $R^{19}$ and $R^{22}$ each are "H. In the case where two or more of $R^{11}$ to $R^{22}$ are substituents, plural substituents may be the same or different. n, n1 to n3 each independently represent an integer of 1 to 3, preferably 1 or 2. $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$, $R^{21}$ and $R^{22}$ each may bond to each other to form a cyclic structure.

In the general formula (1) and the general formula (2), examples of the substituents that $R^{11}$ to $R^{22}$ can take include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms and a nitro group. Of these specific examples, those that may be further substituted with a substituent may be substituted. More preferred substituents are a halogen atom, a cyano group, a substituted or unsubstituted alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 3 to 40 carbon atoms, and a dialkyl-substituted amino group having 1 to 20 carbon atoms. Even more preferred substituents are a fluorine atom, a chlorine atom, a cyano group, a substituted or unsubstituted alkyl group having 1 to 10 carbon atoms, a substituted or unsubstituted alkoxy group having 1 to 10 carbon atoms, a substituted or unsubstituted aryl group having 6 to 15 carbon atoms, and a substituted or unsubstituted heteroaryl group having 3 to 12 carbon atoms.

$R^1$ and $R^2$, $R^3$ and $R^4$, $R^5$ and $R^6$, $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$, $R^{21}$ and $R^{22}$ each may bond to each other to form a cyclic structure. The cyclic structure may be an aromatic ring or an aliphatic ring, or may also be a ring containing a hetero atom. Further, the cyclic structure may be a condensed ring of 2 or more rings. Here, the hetero atom is preferably selected from the group consisting of a nitrogen atom, an oxygen atom and a sulfur atom. Examples of the cyclic structure to be formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazole ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

The cyclic structure to be formed by $R^1$ and $R^2$, $R^3$ and $R^4$, $R^5$ and $R^6$ each bonding to each other is preferably an aromatic ring, more preferably an aromatic ring whose ring skeleton-constituting atoms are carbon atoms alone, and even more preferably contains a benzene ring, and is especially preferably a benzene ring. Preferably, $R^1$ and $R^2$, $R^3$ and $R^4$, $R^5$ and $R^6$ each bond to each other to form a cyclic structure.

In the compounds represented by the general formula (1) and the general formula (2), the secondary amino group (—N″H—) and the carbonyl group [—C(=O)—] or the thiocarbonyl group [—C(=S)—] constitute a hydron-transferable site, and after given exciting energy, ″H leaves from the nitrogen atom of the secondary amino group (—N″H—) and bonds to the oxygen atom of the carbonyl group [—C(=O)—] or to the sulfur atom of the thiocarbonyl group [—C(=S)—], and the nitrogen atom from which ″H has left forms an imino structure (—N=), and the oxygen atom or the sulfur atom having bonded to ″H forms a hydroxy group (—O″H) or a thiol group (—S″H) along with that ″H. At this time, in the compounds represented by the general formula (1) and the general formula (2), hydron transfer can occur at all the above-mentioned hydron-transferable sites. Accordingly, for example, a compound represented by the general formula (2) where $R^{11}$ to $R^{22}$ are all ″H, that is, represented by the following formula (A), which is referred to herein as one example, may take a structure represented by the following formula (A-1) in which one hydron-transferable ″H has transferred after given exciting energy, a structure represented by the following formula (A-2) in which two ″H's have transferred, and a structure represented by the following formula (A-3) in which three ″H's have transferred. The compound in the present invention may be a light-emitting species in any state, but preferably, the compound emits in a state where one hydron-transferable site has undergone hydron transfer, and for example, among the formulae (A-1) to (A-3), the compound preferably emits as a light-emitting species in a state represented by the formula (A-1).

In the general formulae to be described hereinunder after this paragraph, the hydrogen atom for which the expression of ″H is omitted may be a light hydrogen atom ($^1$H), or may be a deuterium atom ($^2$H, D), or may be a tritium atom ($^3$H, T). Preferred is a case of a light hydrogen atom ($^1$H) or a deuterium atom ($^2$H, D); and a typical example is a case where all are light hydrogen atoms ($^1$H). In the structural formulae of concrete compounds to be described hereinunder after this paragraph, the hydrogen atom for which the expression of ″H is omitted represents a light hydrogen atom ($^1$H). Compounds where a part or all of the hydrogen atoms of these concrete compounds are changed to deuterium atom ($^2$H, D) or tritium atoms ($^3$H, T) can be readily exemplified.

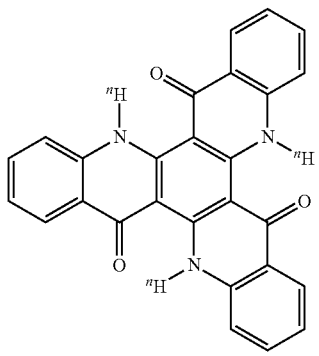

Formula (A)

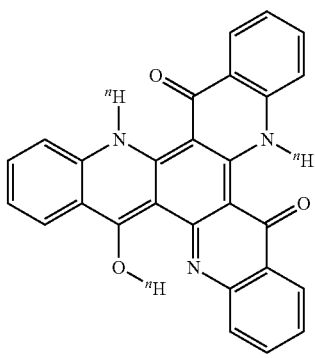

Formula (A-1)

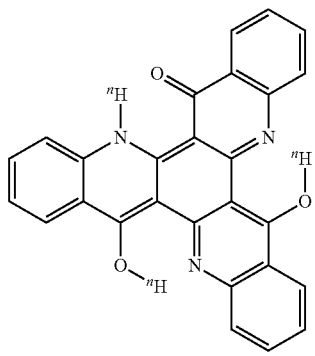

Formula (A-2)

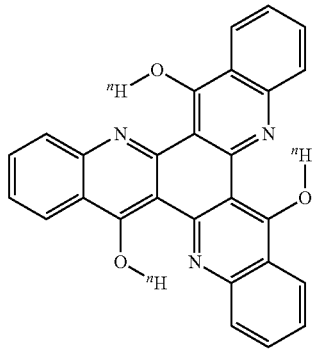

Formula (A-3)

In the following, specific examples of the compound represented by the general formula (1) are shown. However, the compounds represented by the formula (1) and usable in the present invention should not be limitatively interpreted by these specific examples. In the following specific examples, an expression "H" represents $^1$H (light hydrogen atom), and an expression "D" represents $^2$H (deuterium hydrogen atom).
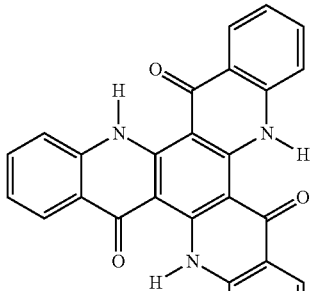
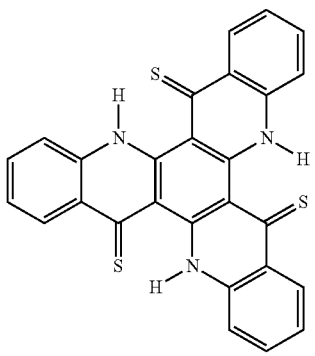
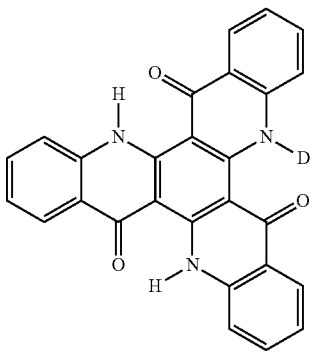
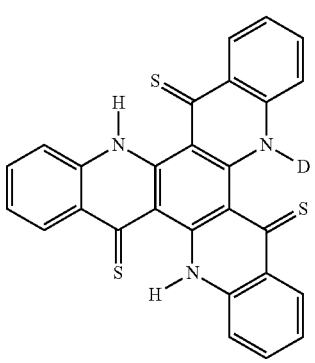
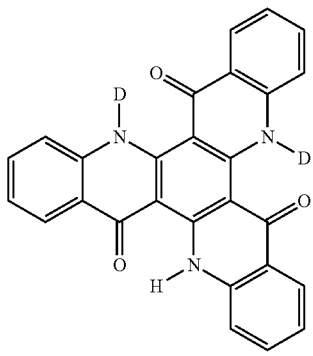
-continued
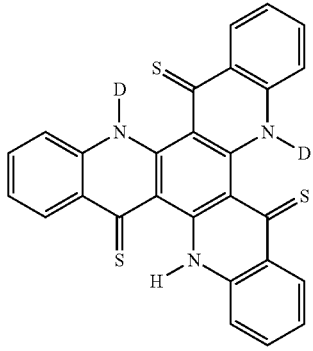
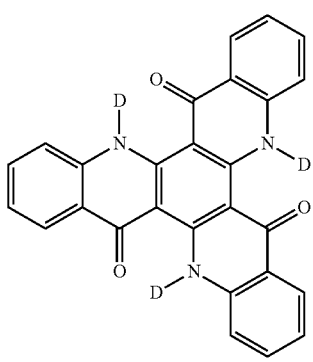
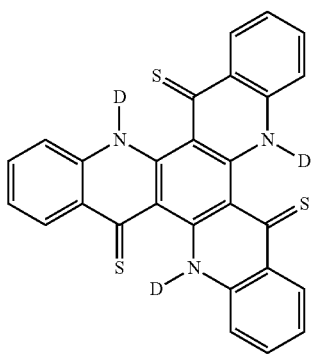

-continued
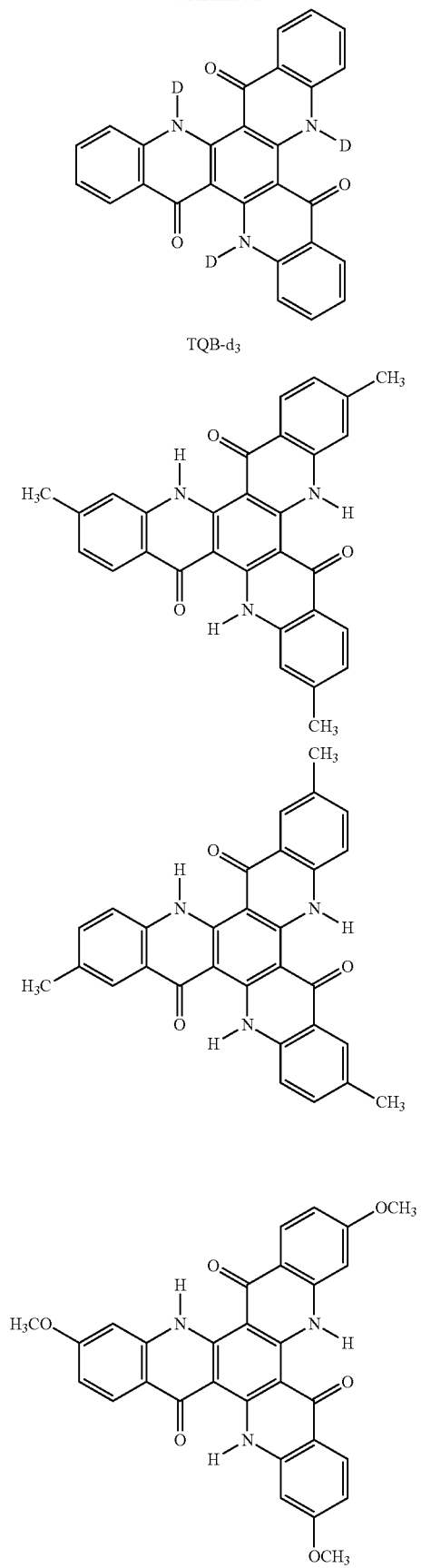
TQB-d₃
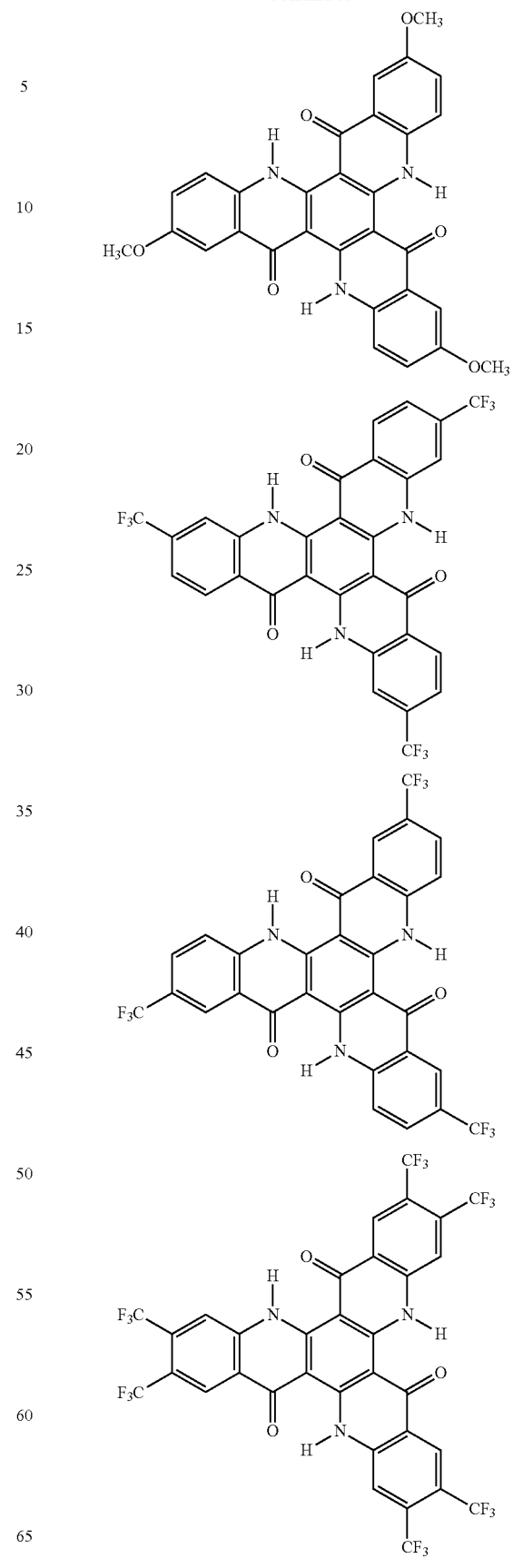

-continued
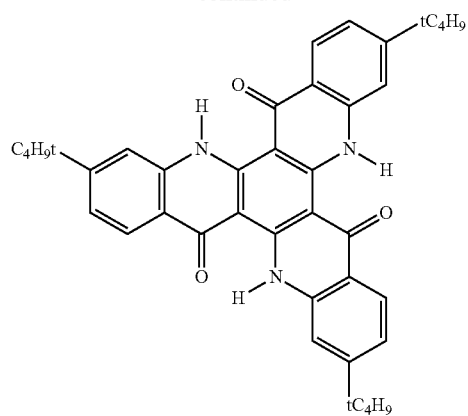
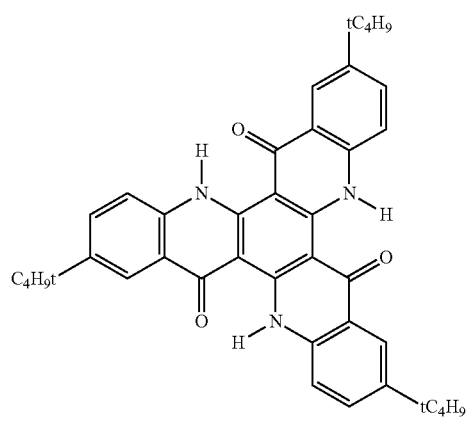
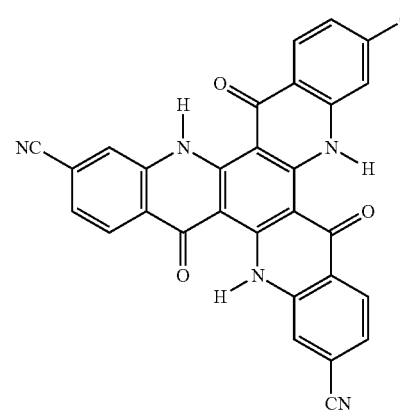
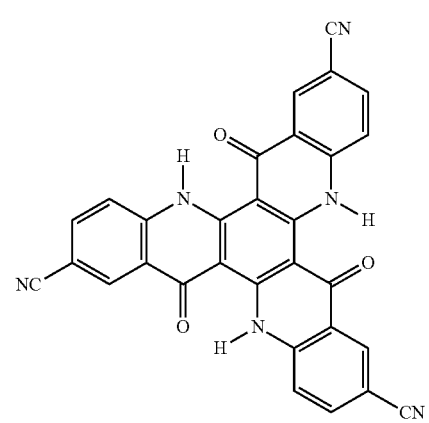
-continued
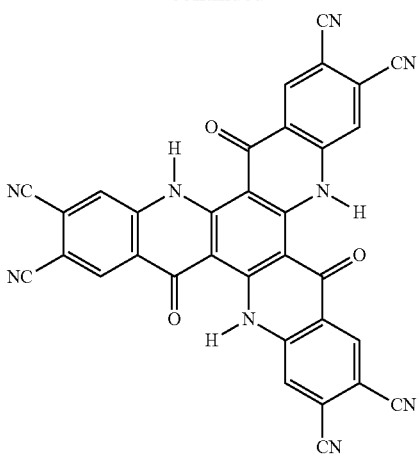
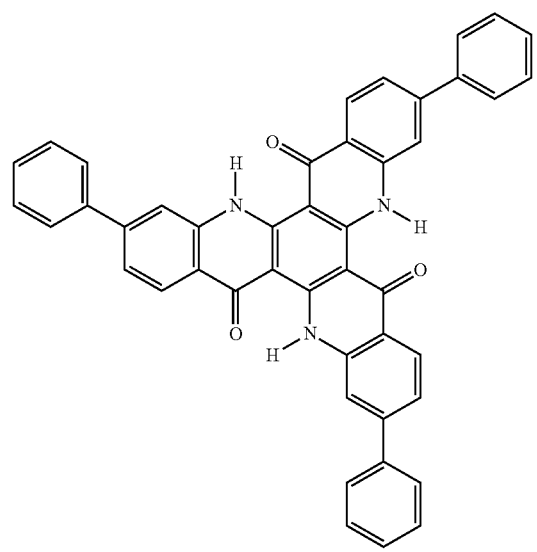
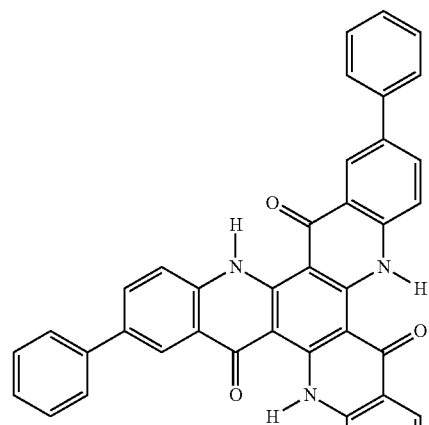

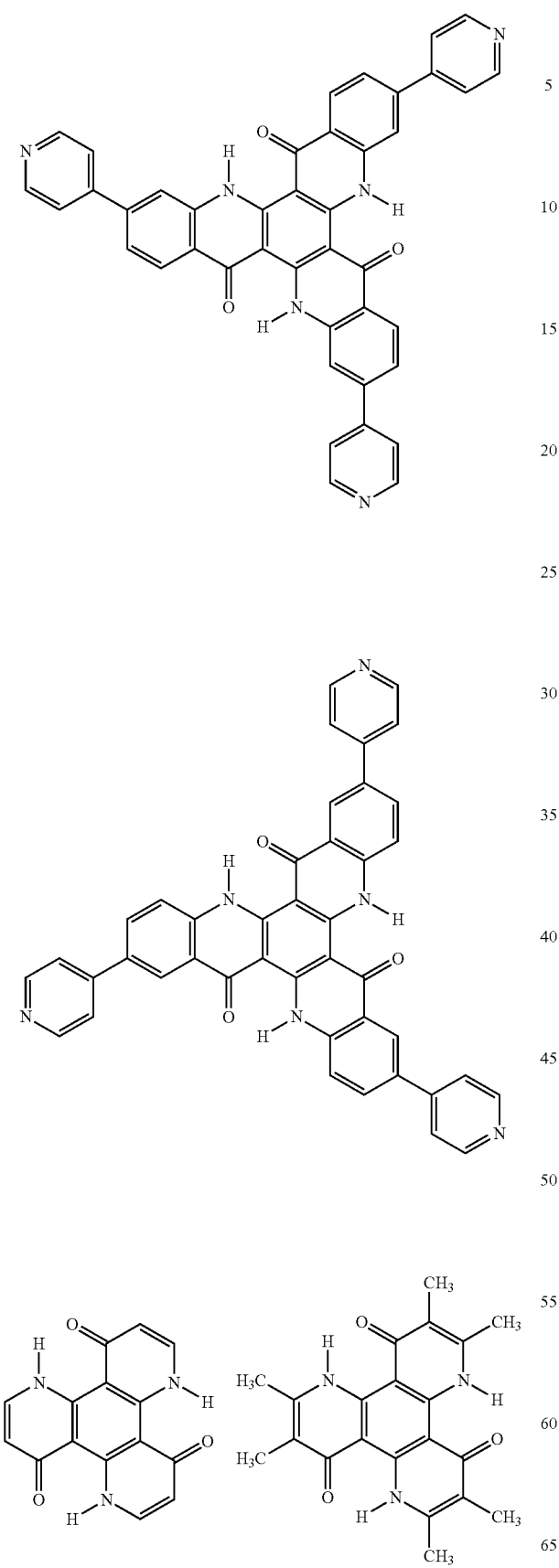
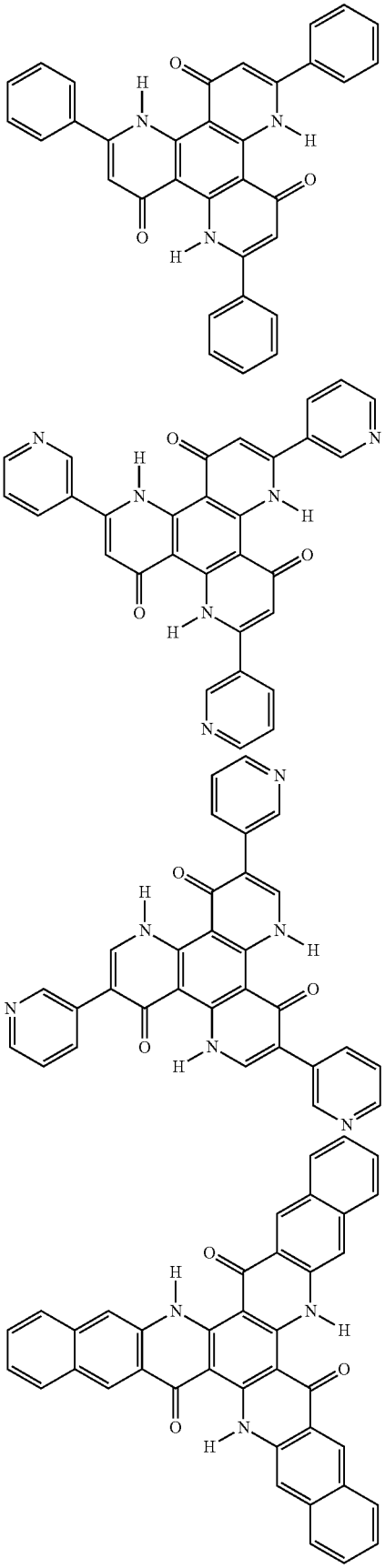

-continued
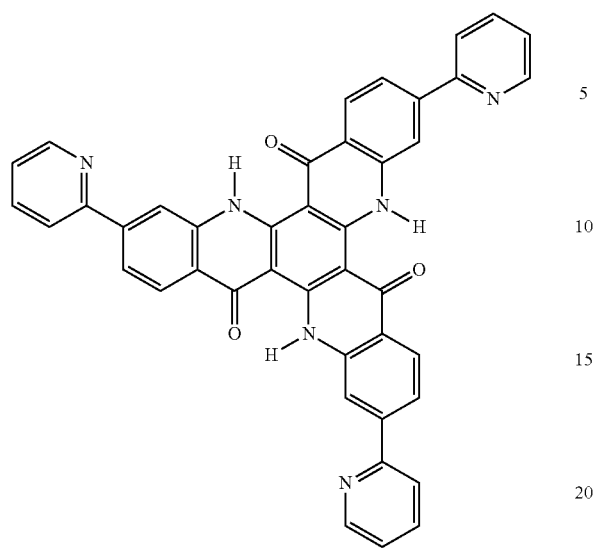
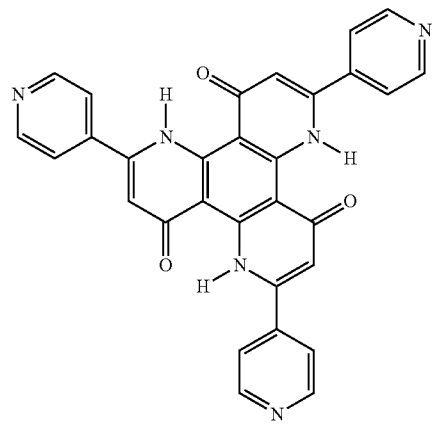
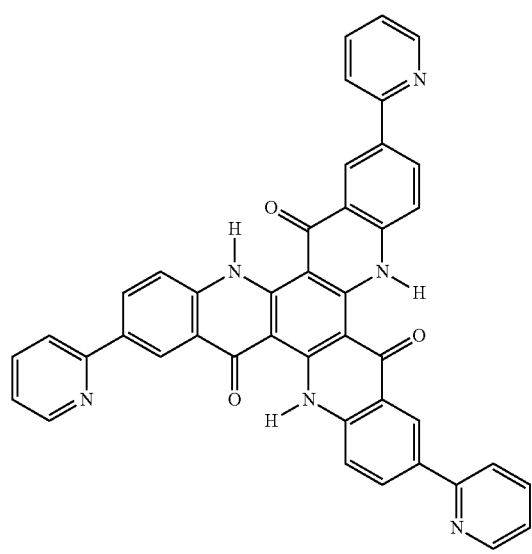
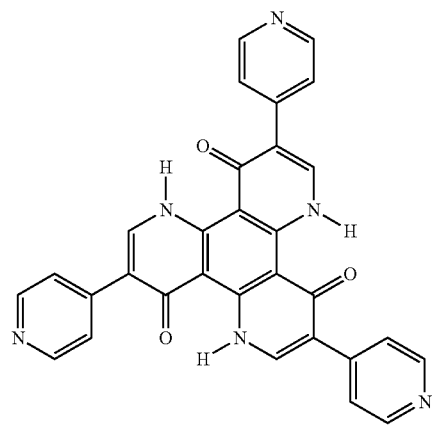
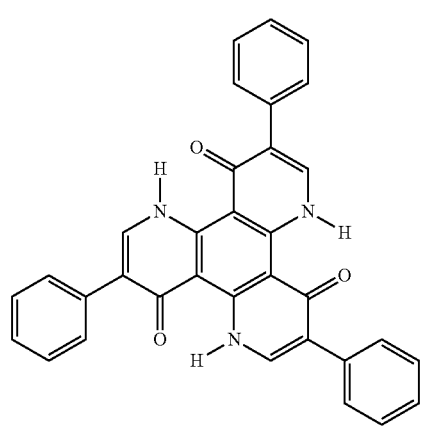
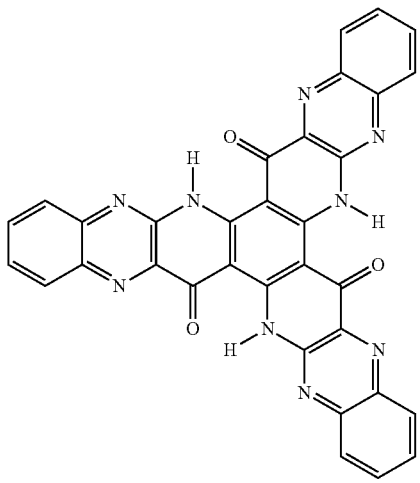

25
-continued
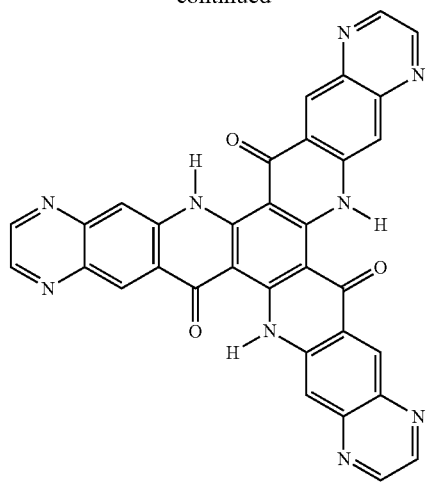
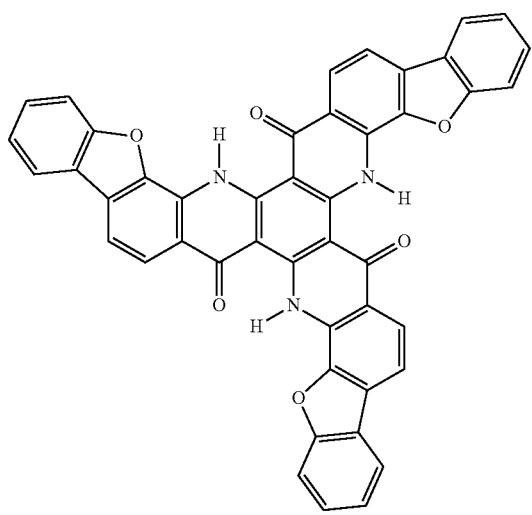
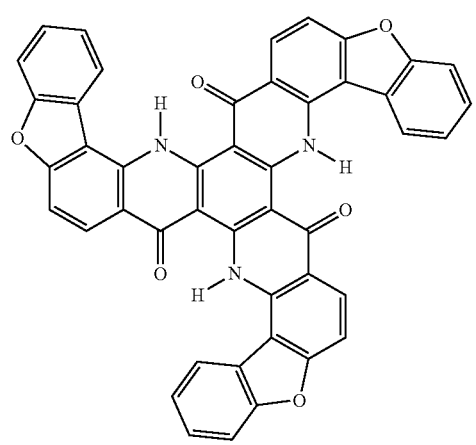
26
-continued
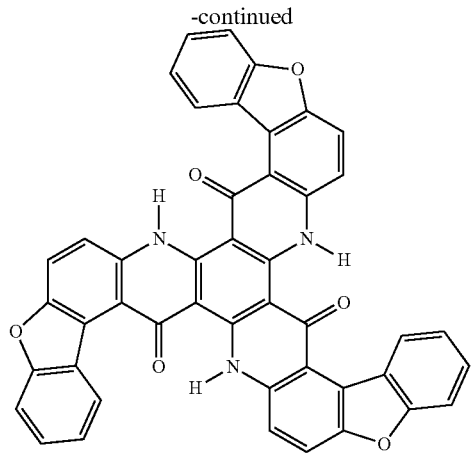
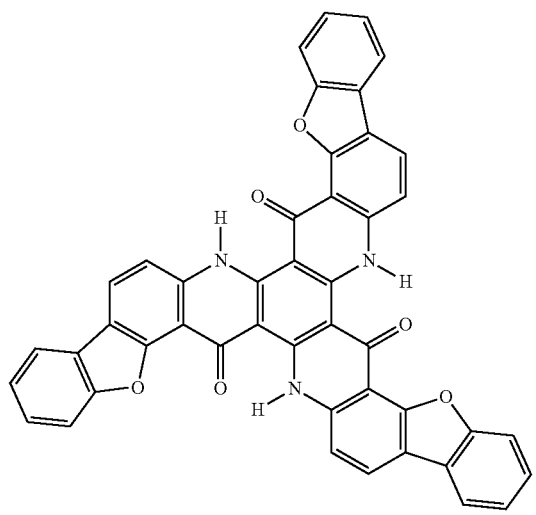
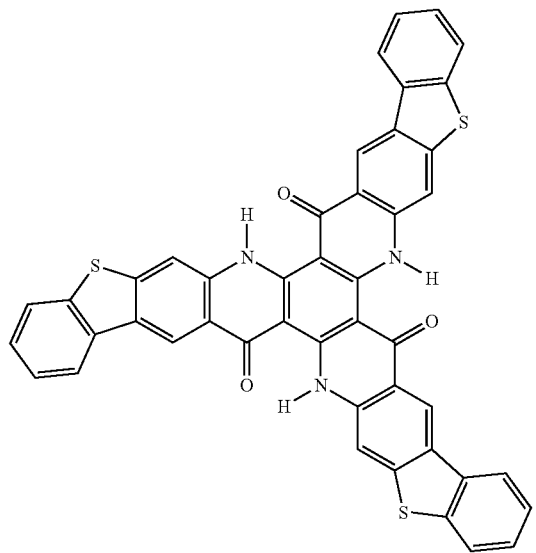

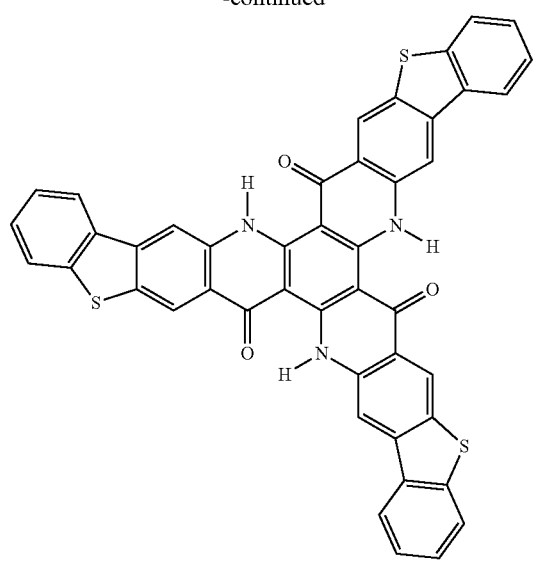
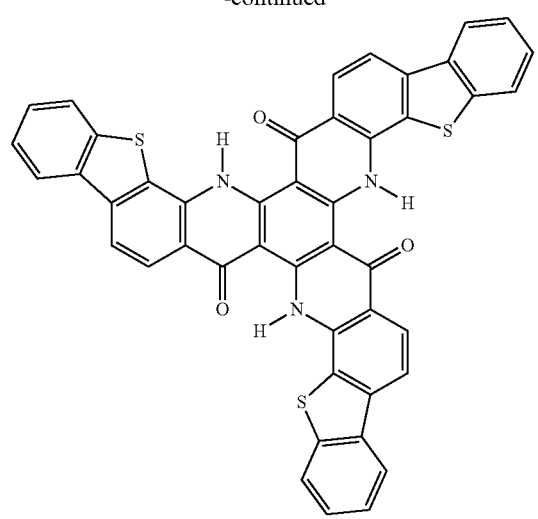
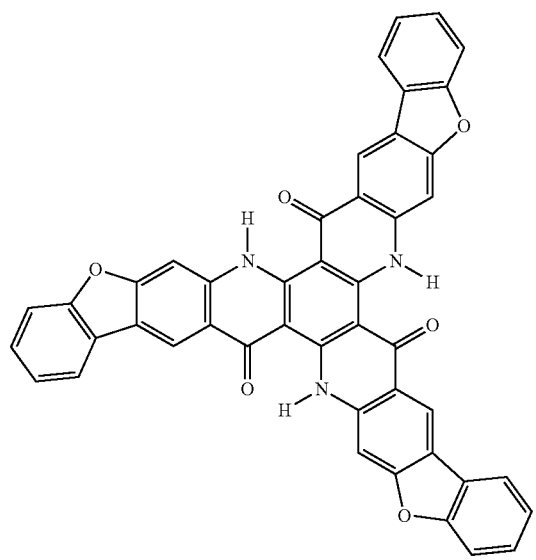
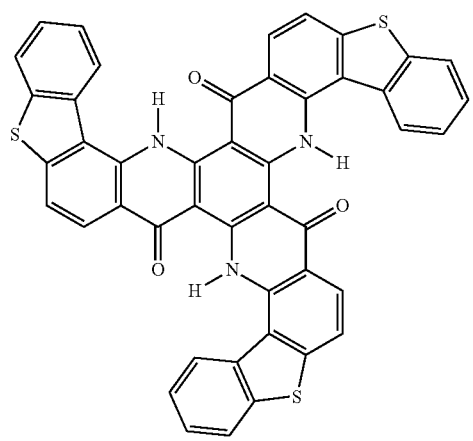
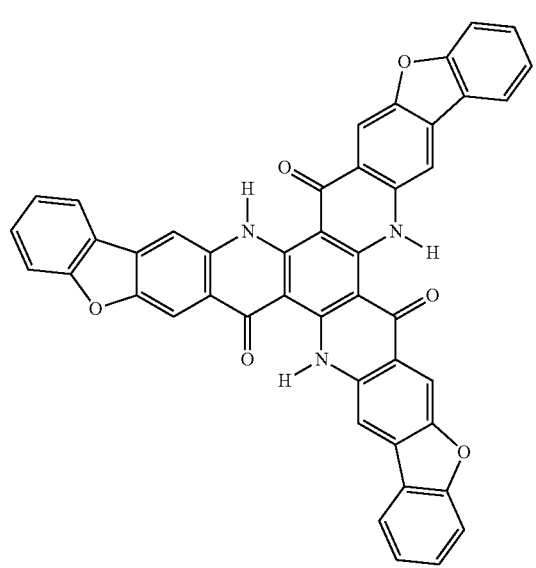
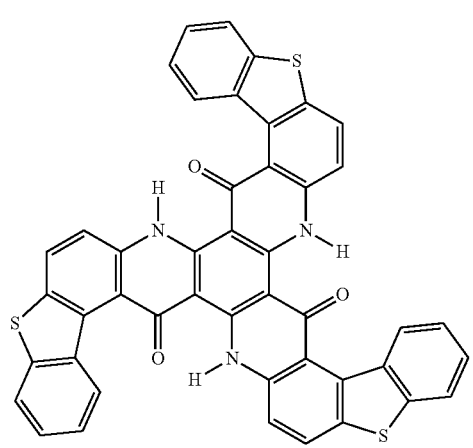

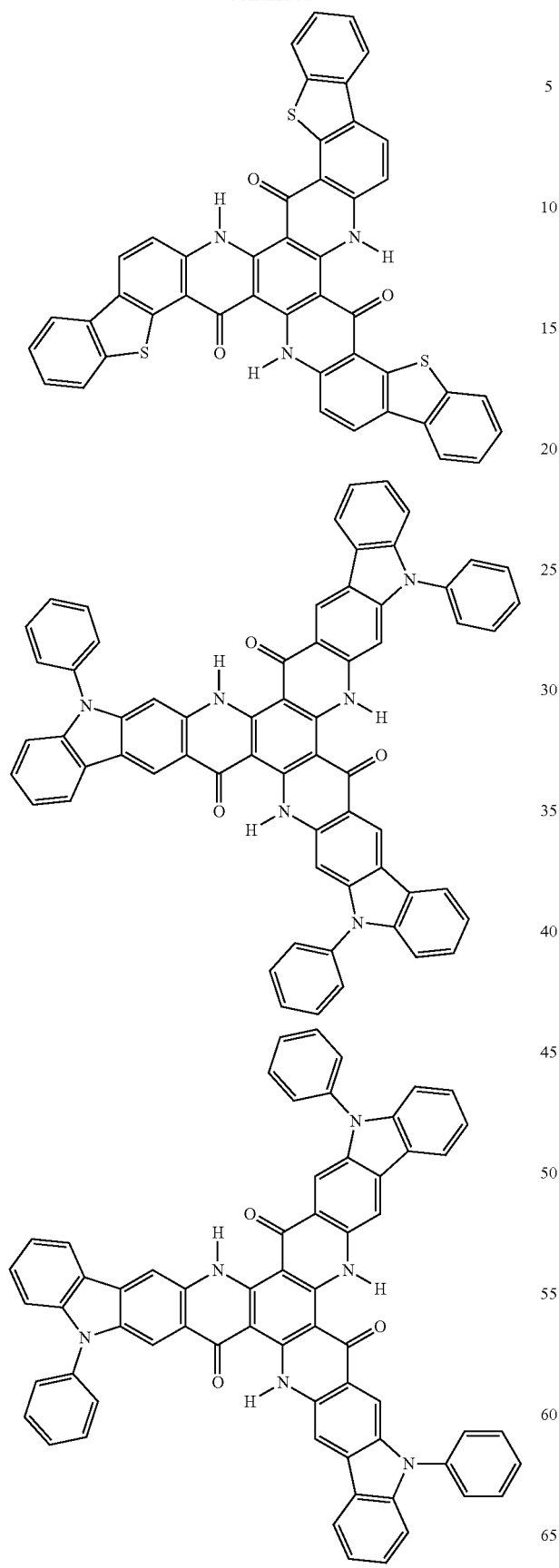

31
-continued
32
-continued
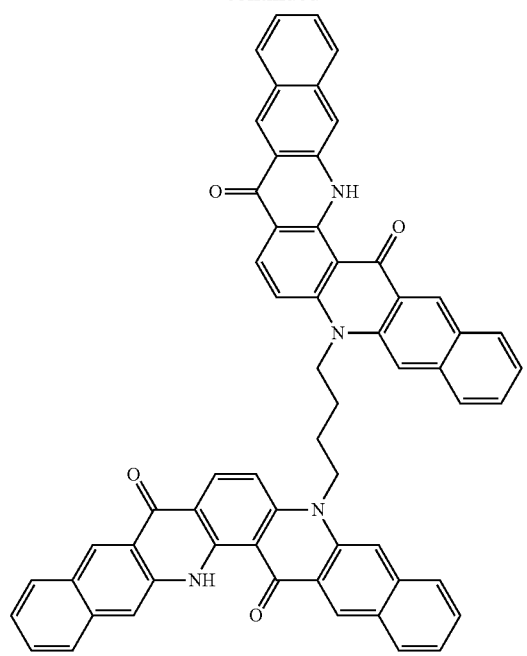
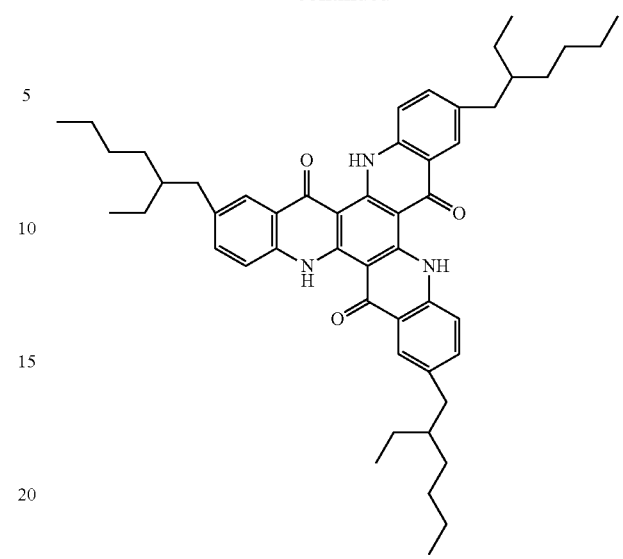
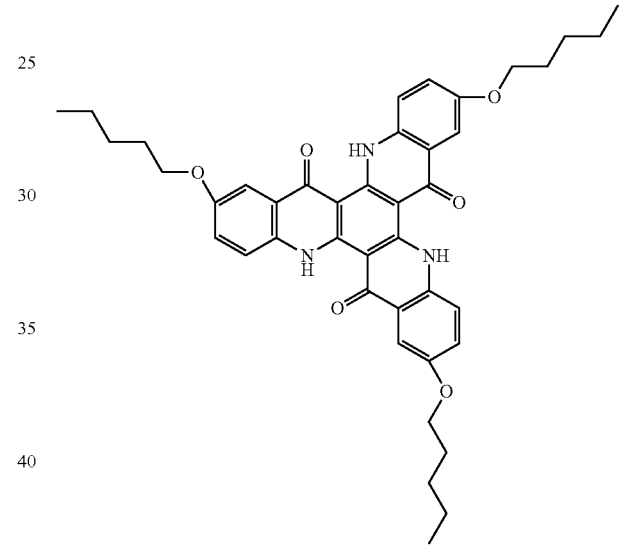
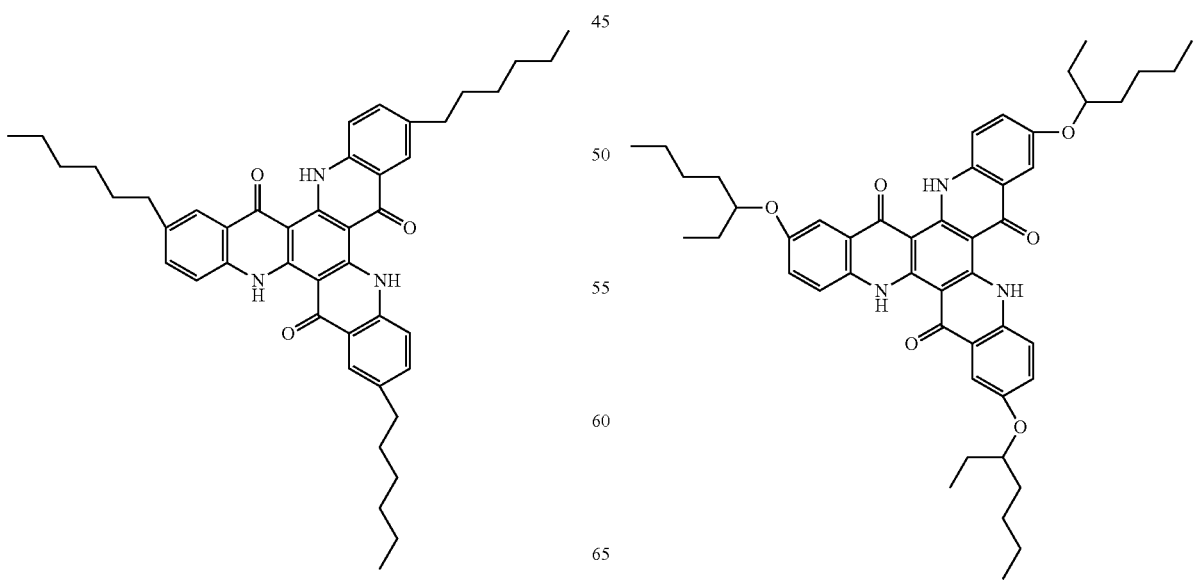

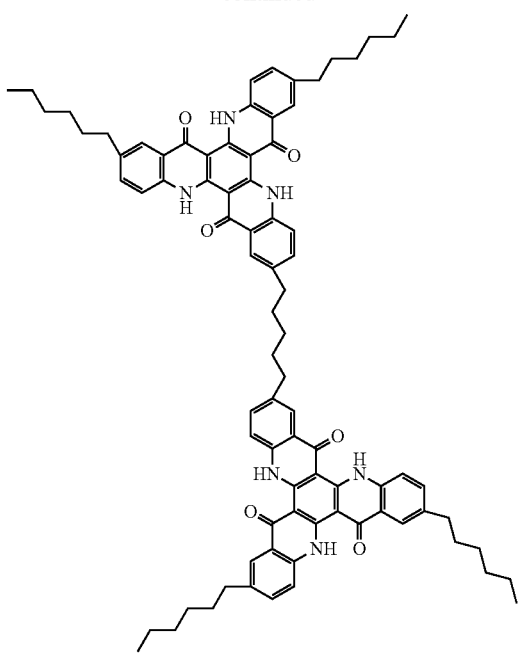 [SMILES: CCCCCOc1ccc2[nH]c3c4c(=O)c5cc(CCCCCc6ccc7[nH]c8c(c(=O)c7c6)c6[nH]c7ccc(OCCCCC)cc7c(=O)c6c6[nH]c7ccc(OCCCCC)cc7c(=O)c86)ccc5[nH]c4c4c(=O)c5cc(OCCCCC)ccc5[nH]c4c3c(=O)c2c1]

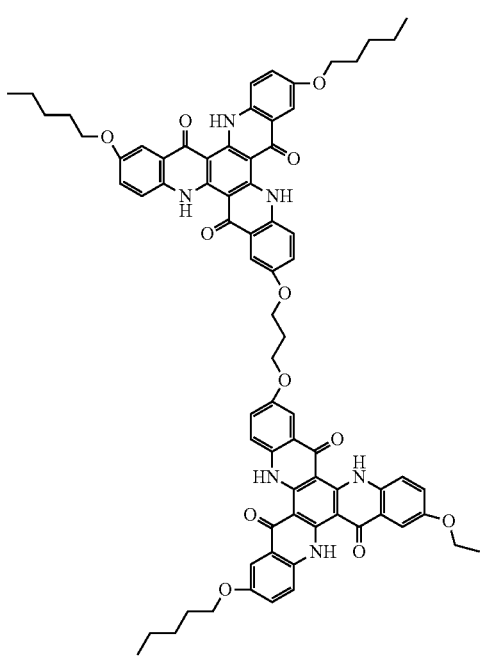

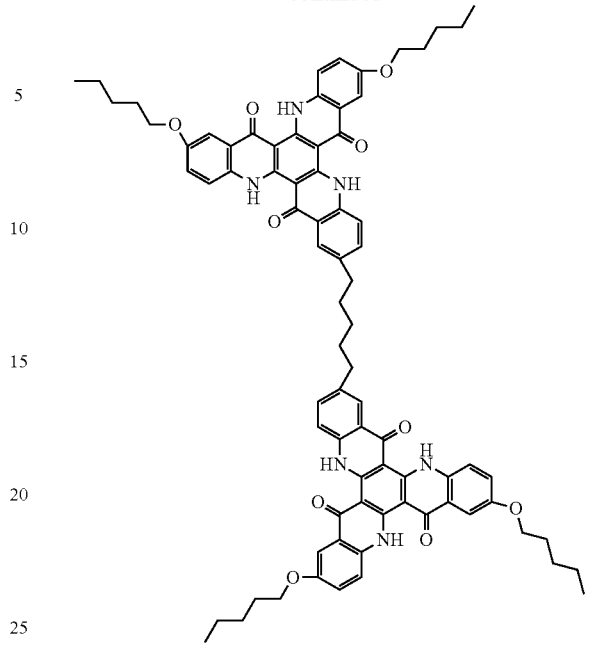

The molecular weight of the compound capable of emitting delayed fluorescence and capable of undergoing intramolecular hydron transfer and usable in the present invention, that is, the compound represented by the general formula (1) is, for example, in the case where an organic layer containing the compound is intended to be formed according to a vapor deposition method and used in devices, preferably 1500 or less, more preferably 1200 or less, even more preferably 1000 or less, and further more preferably 800 or less. The lower limit of the molecular weight is generally 247 or more, and is preferably 290 or more.

Irrespective of the molecular weight thereof, the compound may be formed into a film according to a coating method. When a coating method is employed, even a compound having a relatively large molecular weight can be formed into a film.

The compound capable of emitting delayed fluorescence and capable of undergoing intramolecular hydron transfer may be a polymer produced through polymerization of a polymerizable monomer capable of emitting delayed fluorescence and capable of undergoing intramolecular hydron transfer.

For example, it is considered that a polymerizable group is previously introduced into a structure represented by the general formula (1) or the general formula (2) and the polymerizable group is polymerized to give a polymer, and the polymer is used as a light-emitting material. Specifically, a monomer containing a polymerizable functional group in any of $R^1$ to $R^6$ in the general formula (1) or $R^{11}$ to $R^{22}$ in the general formula (2) is prepared, and this is homopolymerized or copolymerized with any other monomer to give a polymer having a recurring unit, and the polymer can be used as a material for organic light-emitting devices. Alternatively, compounds each having a structure represented by the general formula (1) or the general formula (2) are coupled to give a dimer or a trimer, and it can be used as a material for organic light-emitting devices.

Examples of the polymer having a recurring unit containing a structure represented by the general formula (1)

include polymers containing a structure represented by the following general formula (11) or (12).

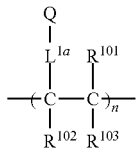

General Formula (11)

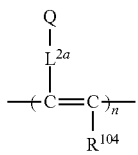

General Formula (12)

In the general formula (11) or (12), Q represents a group containing a structure represented by the general formula (1), and $L^1$ and $L^2$ each represent a linking group. The carbon number of the linking group is preferably 0 to 20, more preferably 1 to 15, even more preferably 2 to 10. Preferably, the linking group has a structure represented by —$X^{11}$-$L^{11}$-. Here, $X^{11}$ represents an oxygen atom or a sulfur atom and is preferably an oxygen atom. $L^{11}$ represents a linking group, and is preferably a substituted or unsubstituted alkylene group, or a substituted or unsubstituted arylene group, more preferably a substituted or unsubstituted alkylene group having 1 to 10 carbon atoms, or a substituted or unsubstituted phenylene group.

In the general formula (11) or (12), $R^{101}$, $R^{102}$, $R^{103}$ and each independently represent a substituent. Preferably, the substituent is a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of $R^1$ to $R^6$ in the structure of the general formula (1) constituting Q. Two or more linking groups may bond to one Q to form a crosslinked structure or a network structure.

Specific structural examples of the recurring unit include structures represented by the following formulae (13) to (16).

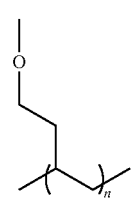

Formula (13)

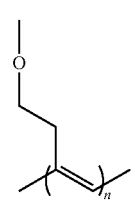

Formula (14)

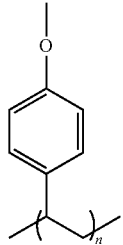

Formula (15)

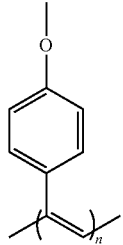

Formula (16)

The polymer having a recurring unit containing any of these formulae (13) to (16) may be synthesized by previously introducing a hydroxy group into any of $R^1$ to $R^6$ in the structure of the general formula (1), then reacting it as a linker with any of the following compounds to introduce a polymerizable group thereinto, and polymerizing the polymerizable group.

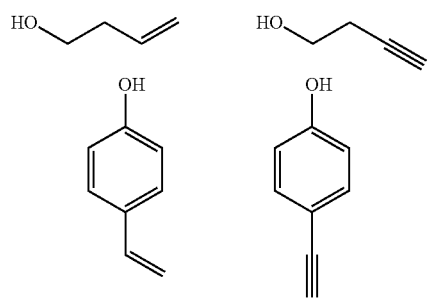

The polymer containing a structure represented by the general formula (1) in the molecule may be a polymer formed of the recurring unit having the structure represented by the general formula (1) or a polymer containing a recurring unit having any other structure. One kind alone or two or more kinds of recurring units having a structure represented by the general formula (1) may be contained in the polymer. The recurring unit not having a structure represented by the general formula (1) includes those derived from a monomer usable in ordinary copolymerization. Examples thereof include recurring units derived from monomers having an ethylenic unsaturated bond such as ethylene or styrene.

[Compound Represented by General Formula (1)]

A method for synthesizing the compound represented by the general formula (1) is not specifically limited. For synthesis of the compound represented by the general formula (1), for example, the synthesis method and the condition described in Dyes Pigments 1990, 12, 301 may be referred to. In addition, the compound represented by the general formula (1) may also be synthesized by combining any other known synthesis reactions.

[Organic Light-Emitting Device]

The organic light-emitting device of the present invention uses a compound capable of emitting delayed fluorescence and capable of undergoing intramolecular hydron transfer. The compound capable of emitting delayed fluorescence and capable of undergoing intramolecular hydron transfer exhibits a sufficiently high quantum yield enough for practical use and can be effectively used as a light-emitting material in the organic light-emitting device. In addition, the compound capable of emitting delayed fluorescence and capable of undergoing intramolecular hydron transfer can also be used as a host or an assist dopant for the organic light emitting device. For example, the organic light-emitting device using a compound capable of emitting delayed fluorescence and capable of undergoing intramolecular hydron transfer as a light-emitting material is characterized by having a high emission efficiency since the compound therein functions as a delayed fluorescent material. The principle will be described below with reference to an organic electroluminescent device taken as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing outdoor air or the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light, and thus the light is observed as fluorescent light that is delayed from the normal fluorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

Using a compound capable of emitting delayed fluorescence and capable of undergoing intramolecular hydron transfer as a light-emitting material in a light-emitting layer, excellent organic light-emitting devices such as organic photoluminescent device (organic PL device) and an organic electroluminescent device (organic EL device) can be provided. An organic photoluminescent device has a structure where at least a light-emitting layer is formed on a substrate. An organic electroluminescent device has a structure including at least an anode, a cathode and an organic layer formed between the anode and the cathode. The organic layer contains at least a light-emitting layer, and may be formed of a light-emitting layer alone, or may has one or more other organic layers in addition to a light-emitting layer. The other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. A configuration example of an organic electroluminescent device is shown in FIG. 1. In FIG. 1, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the organic electroluminescent device are described. The description of the substrate and the light-emitting layer given below may apply to the substrate and the light-emitting layer of an organic photoluminescent device.

(Substrate)

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

(Anode)

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

(Cathode)

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer in which holes and electrons injected from an anode and a cathode are recombined to give excitons for light emission. A light-emitting material may be used singly in the light-emitting layer, but preferably, the layer contains a light-emitting layer and a host material. As the light-emitting material, one or more selected from a group of compounds capable of emitting delayed fluorescence and capable of undergoing intramolecular hydron transfer can be used. In order that the organic electroluminescent device and the organic photoluminescent device of the present invention can express a high light emission efficiency, it is important to confine the singlet exciton and the triplet exciton formed in the light-emitting material to the light-emitting material. Accordingly, preferably, a host material is used in addition to the light-emitting material in the light-emitting layer. As the host material, an organic compound, of which at least any one of the excited singlet energy and the excited triplet energy is higher than that of the light-emitting material, may be used. As a result, the singlet exciton and the triplet exciton formed in the light-emitting material can be confined to the molecule of the light-emitting material to sufficiently derive the light emission efficiency thereof. Needless-to-say, there may be a case where a high light emission efficiency could be attained even though the singlet exciton and the triplet exciton could not be sufficiently confined, and therefore, any host material capable of realizing a high light emission efficiency can be used in the present invention with no specific limitation. In the organic light-emitting device or the organic electroluminescent device of the present invention, light emission occurs from the light-emitting material (compound capable of emitting delayed fluorescence and capable of undergoing intramolecular hydron transfer) contained in the light-emitting layer. The light emission contains both of fluorescent emission and delayed fluorescent emission. In addition, a part of light emission may be partially from a host material.

In the case where a host material is used, the content of the compound serving as a light-emitting material, that is, the compound capable of emitting delayed fluorescence and capable of undergoing intramolecular hydron transfer in the light-emitting layer is preferably 0.1% by weight or more, more preferably 1% by weight or more, and is preferably 50% by weight or less, more preferably 20% by weigh or less, even more preferably 10% by weight or less.

The host material in the light-emitting layer is preferably an organic compound having hole transport competence and electron transport competence, capable of preventing prolongation of emission wavelength and having a high glass transition temperature.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be inserted adjacent to the light-emitting layer on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy of the light-emitting layer, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

In producing the organic electroluminescent device, the compound capable of emitting delayed fluorescence and capable of undergoing intramolecular hydron transfer may be used not only in the light-emitting layer but also in any other layer than the light-emitting layer. In so doing, the compound capable of emitting delayed fluorescence and capable of undergoing intramolecular hydron transfer used in the light-emitting layer and the compound capable of emitting delayed fluorescence and capable of undergoing intramolecular hydron transfer used in the other layer than the light-emitting layer may be the same as or different from each other. For example, the compound capable of emitting delayed fluorescence and capable of undergoing intramolecular hydron transfer may be used in the above-mentioned injection layer, the blocking layer, the hole blocking layer, the electron blocking layer, the exciton blocking layer, the hole transport layer, and the electron transport layer. The method for forming these layers is not specifically limited, and the layers may be formed according to any of a dry process or a wet process.

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function. In the structural formulae of the following exemplary compounds, n represents an integer of 3 to 10.

First, preferred compounds for use as a host material in a light-emitting layer are mentioned below.

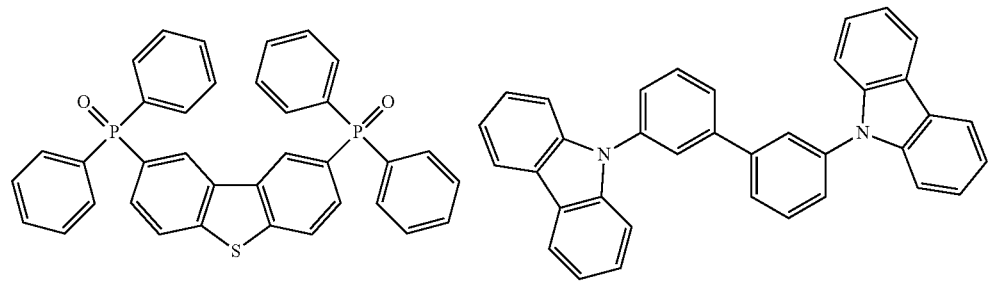

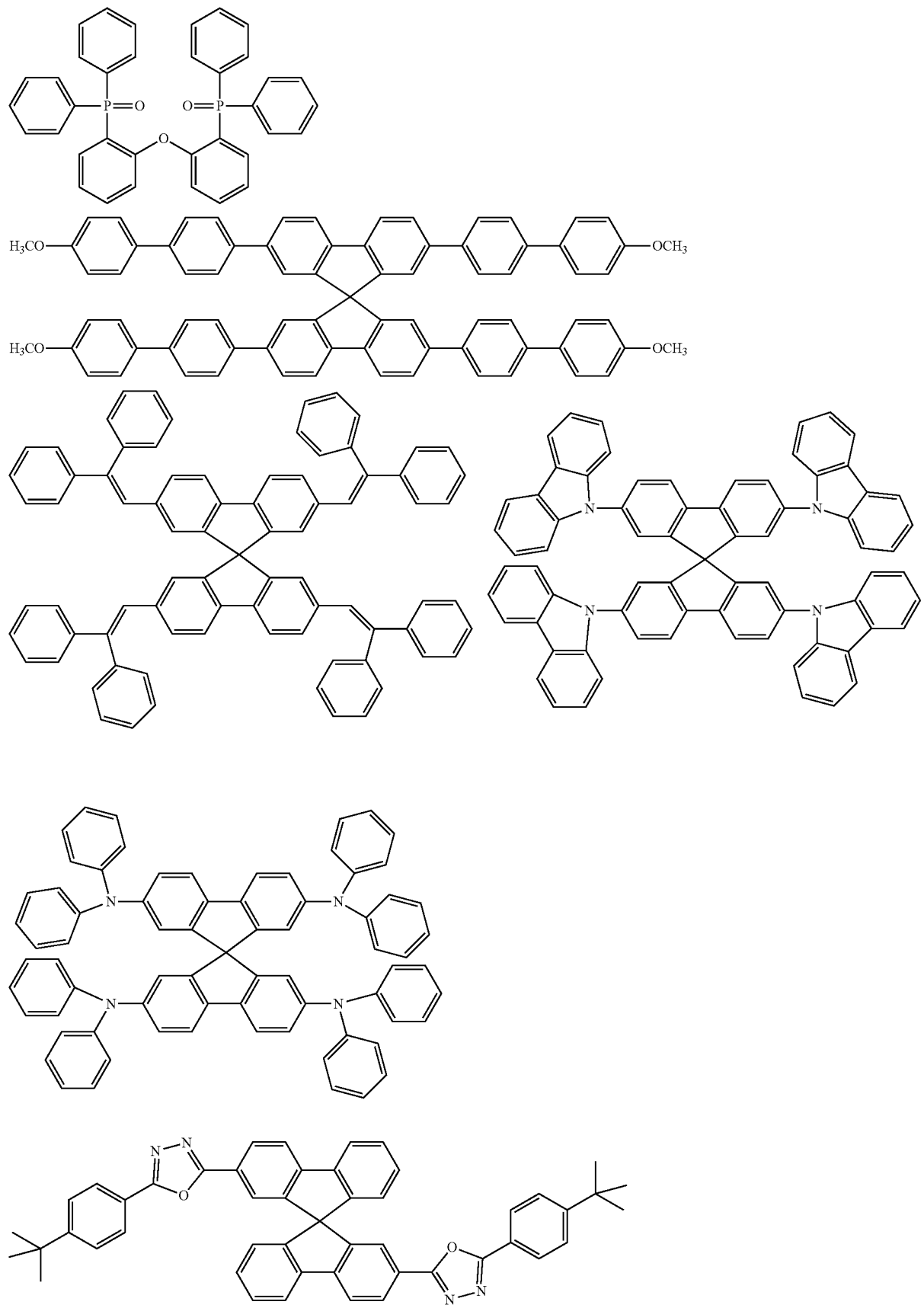

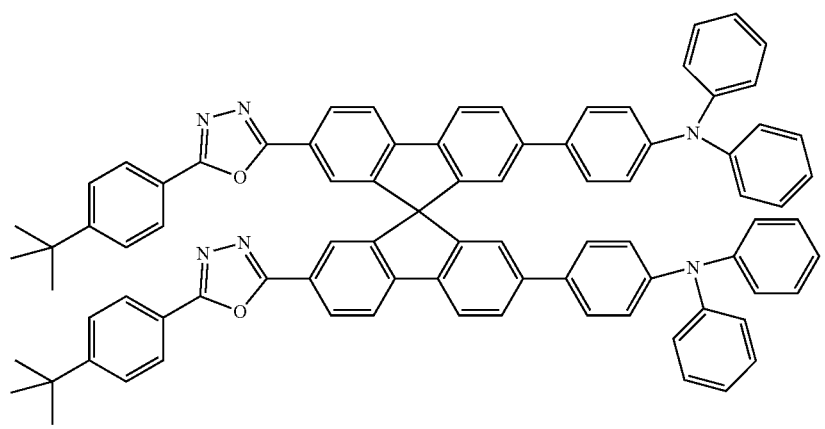
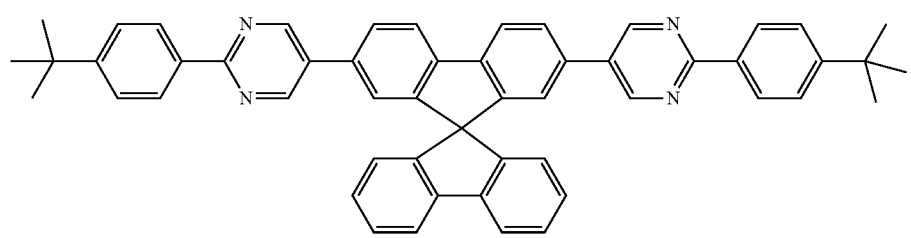
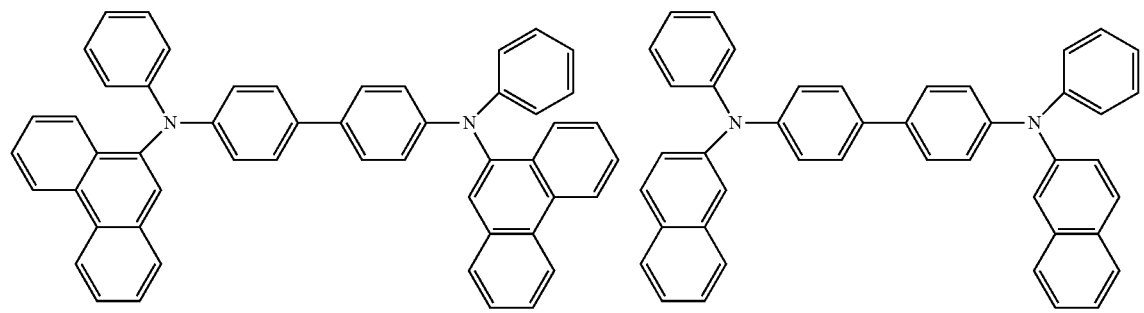
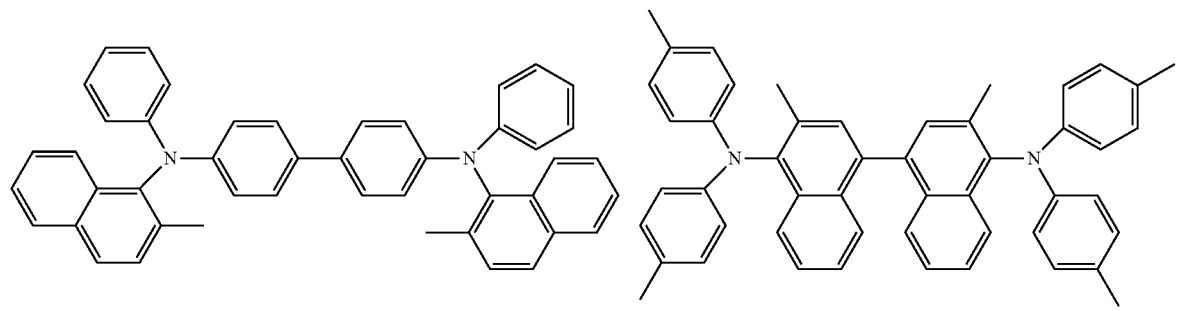

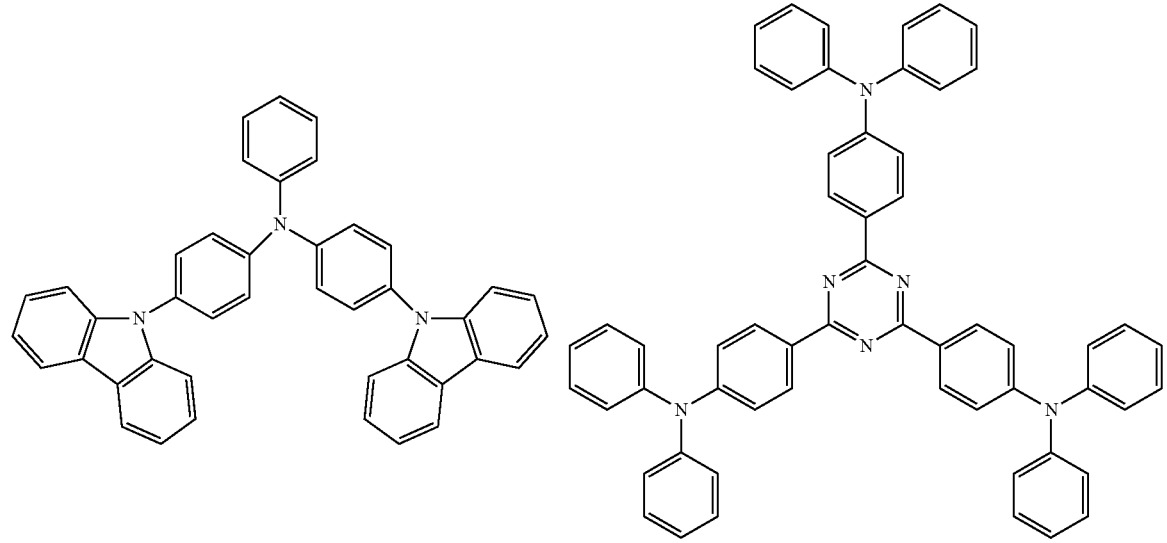
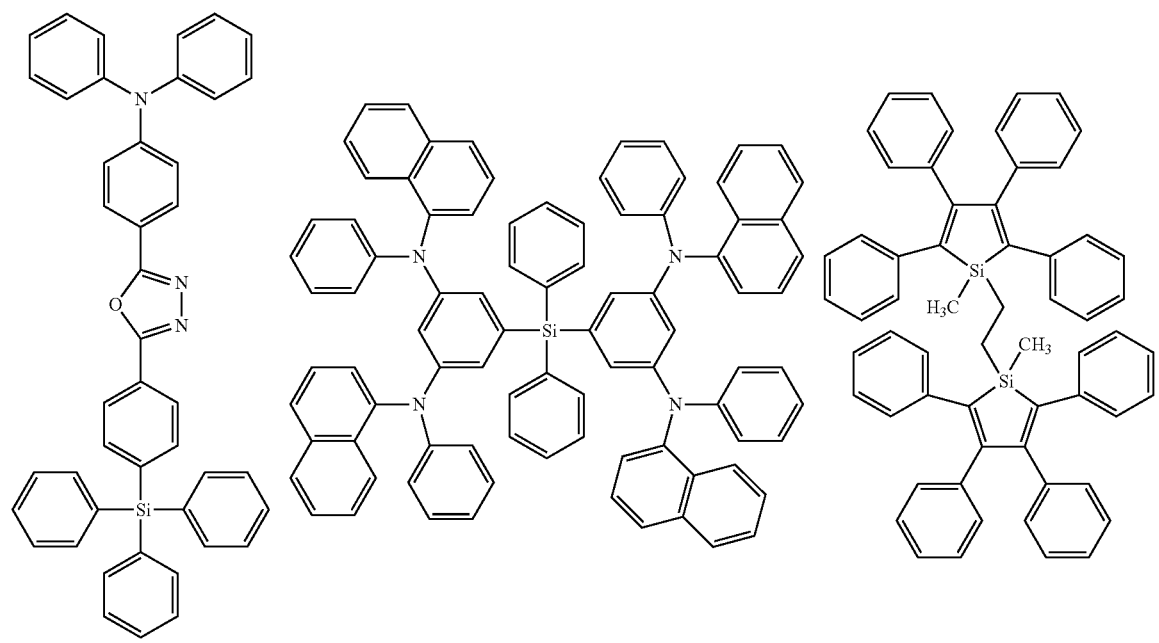
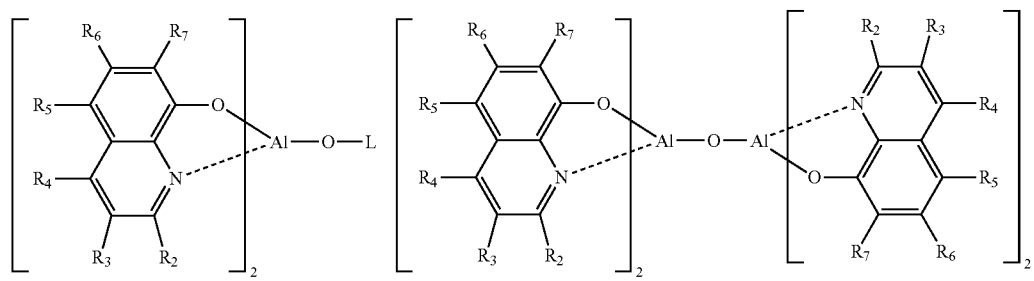
$R_2$-$R_7$ = H or substituent
L = ligand

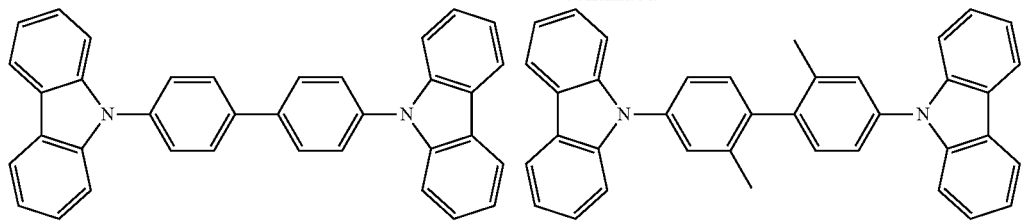
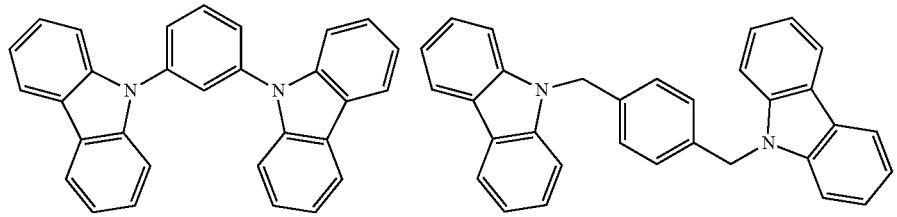
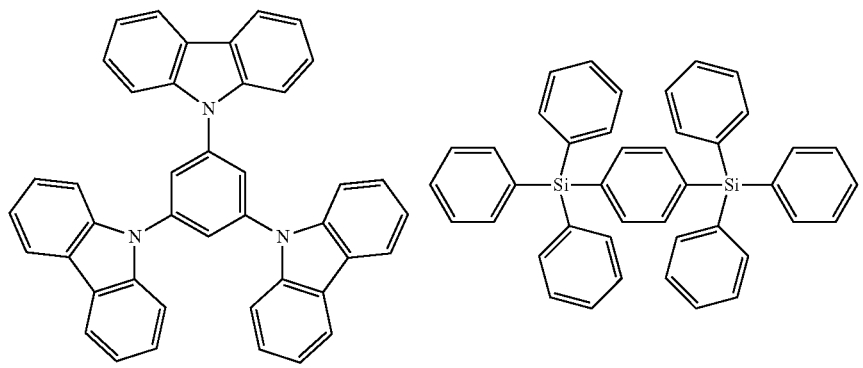
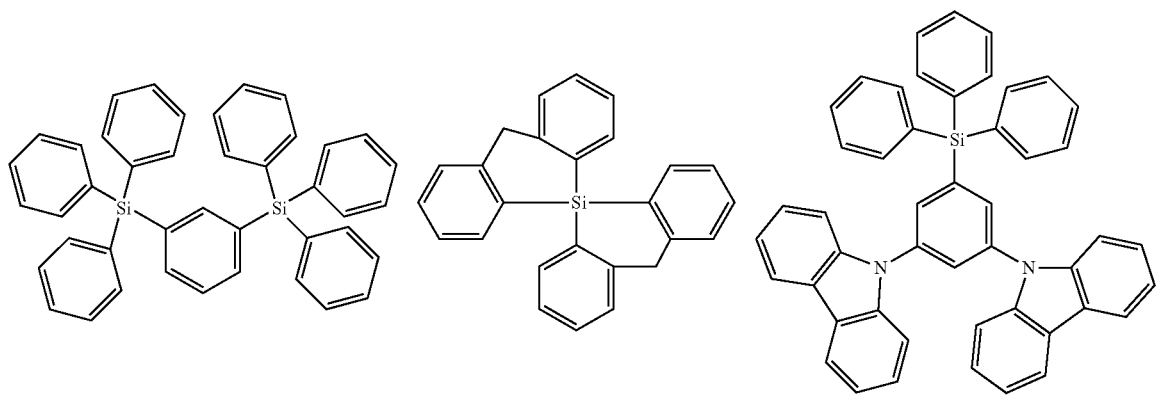
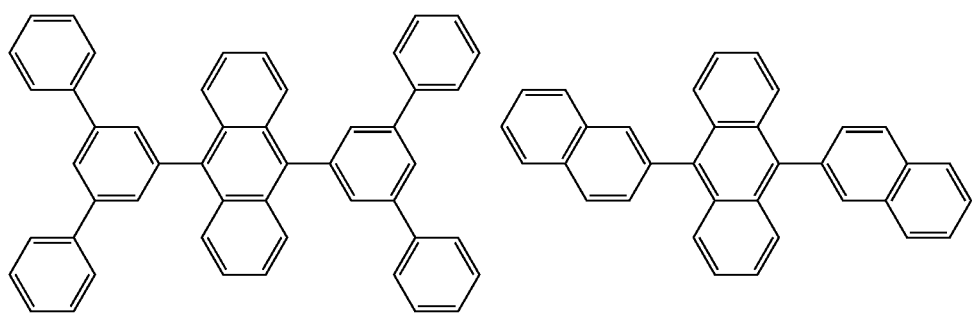

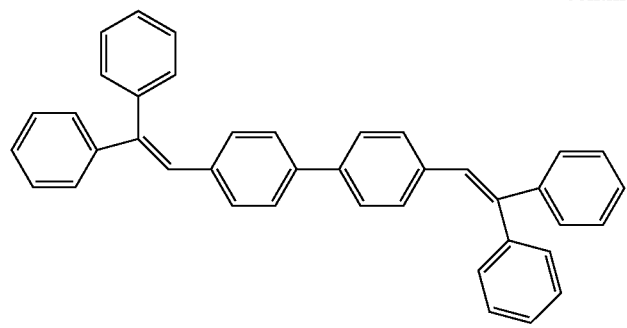
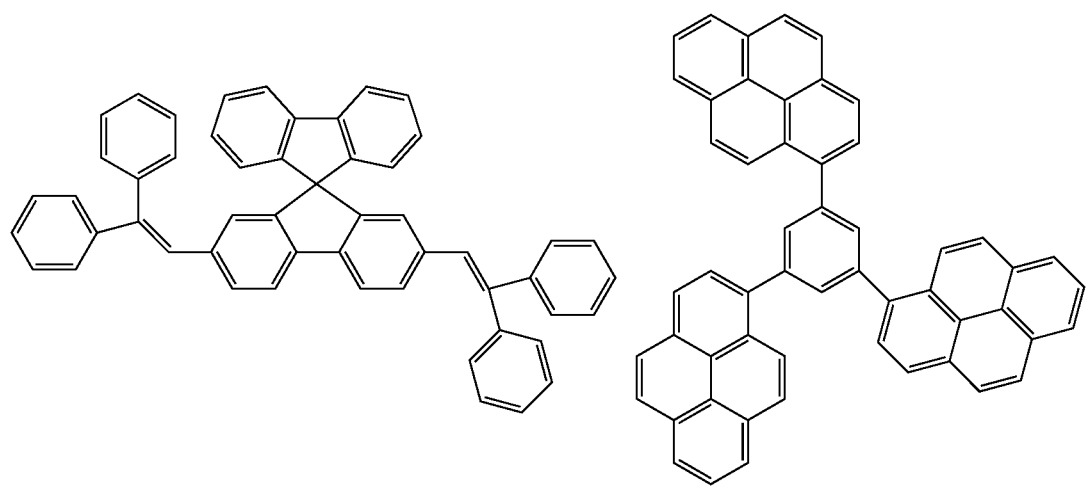
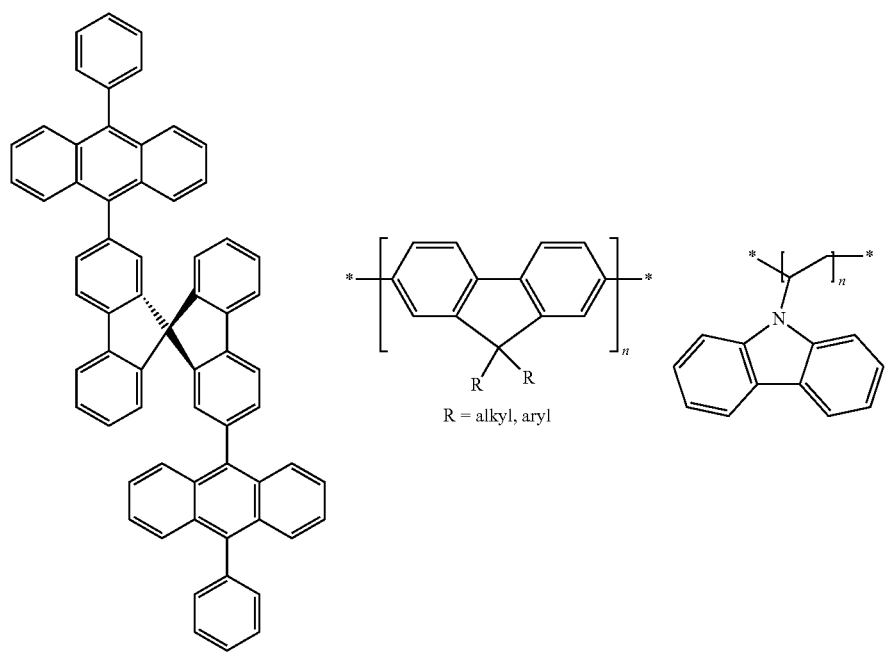

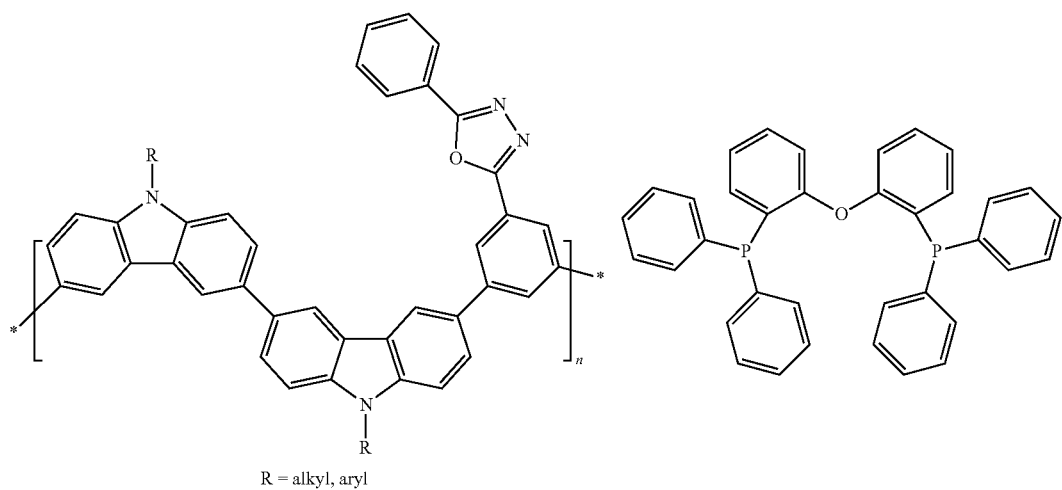
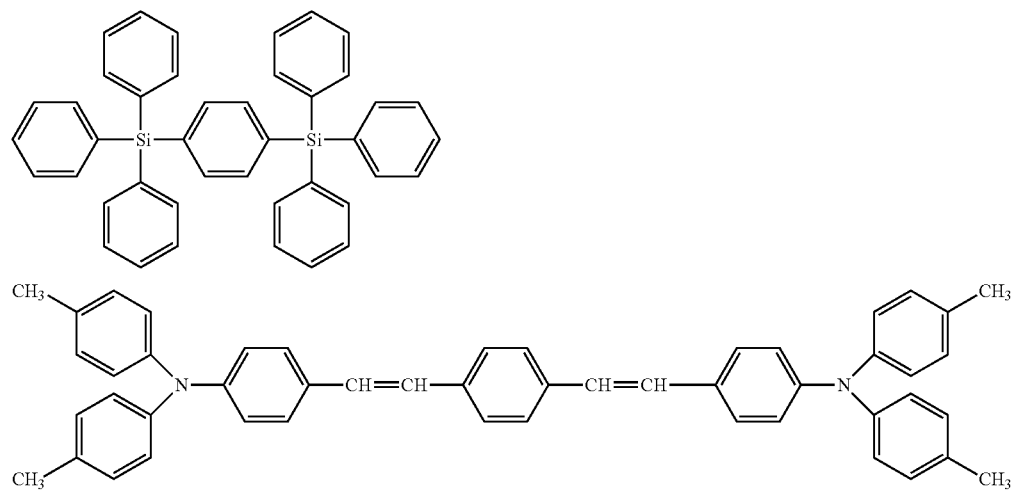
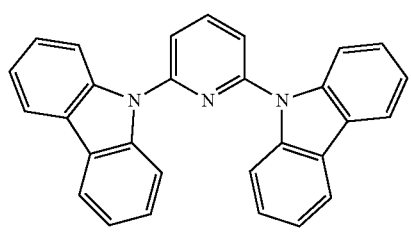

Next, preferred compounds for use as a hole injection material are mentioned below.
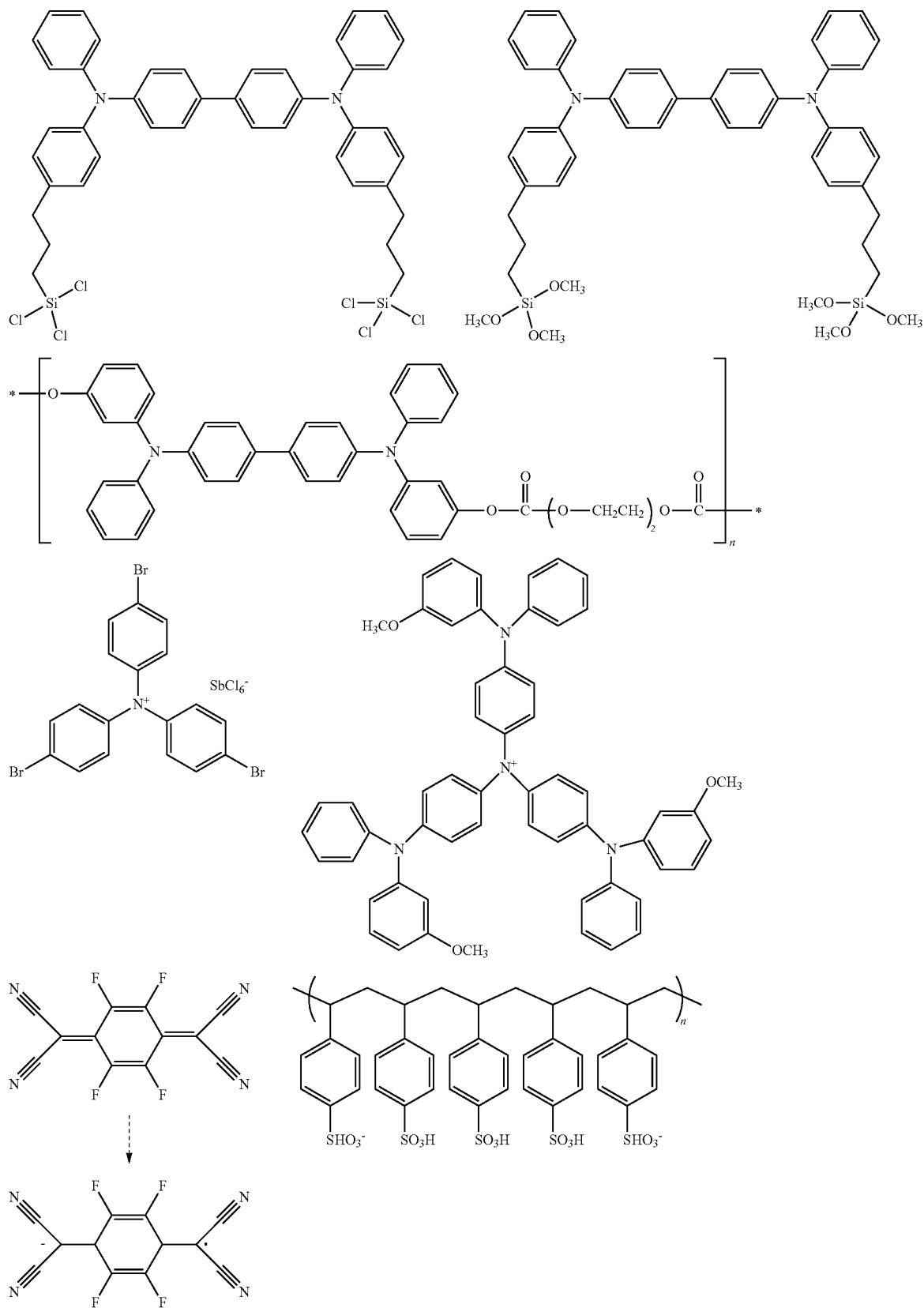

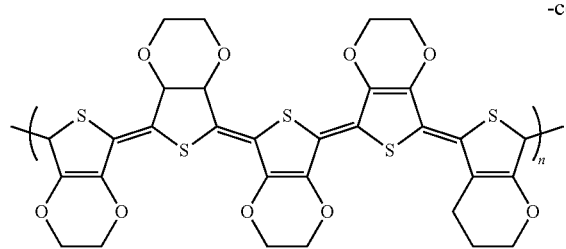
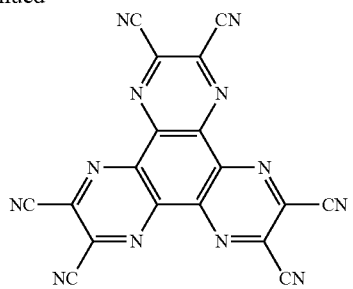
Next, preferred compounds for use as a hole transport material are mentioned below.
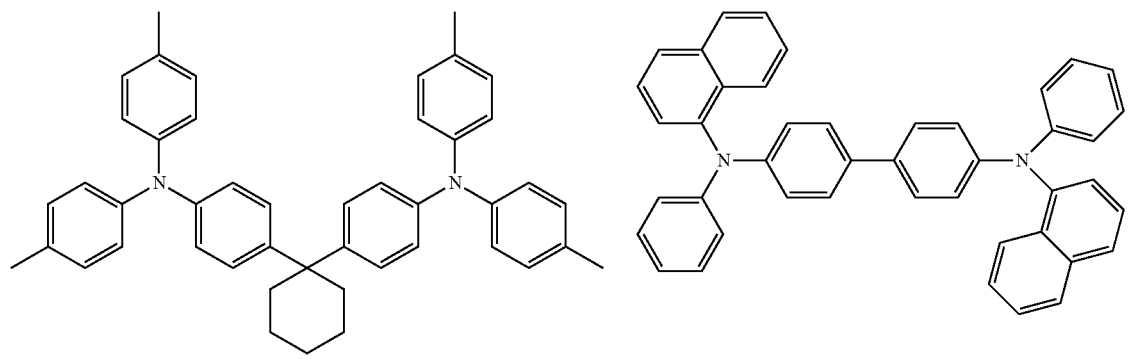
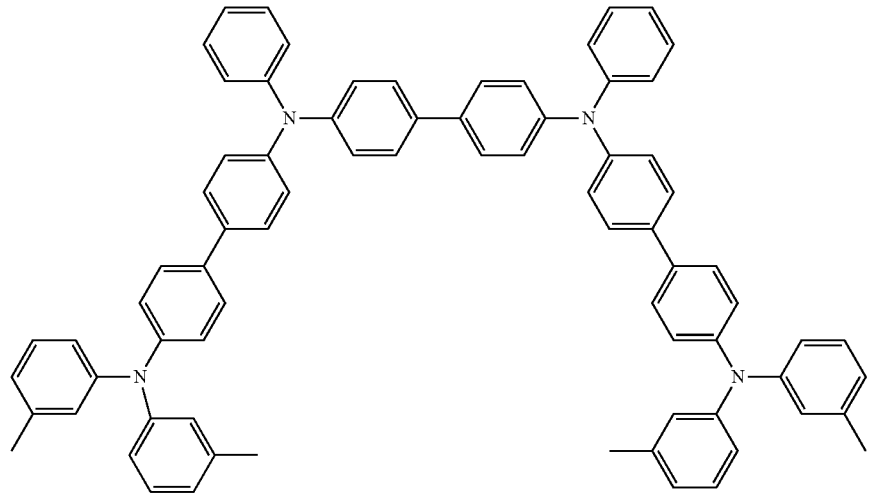
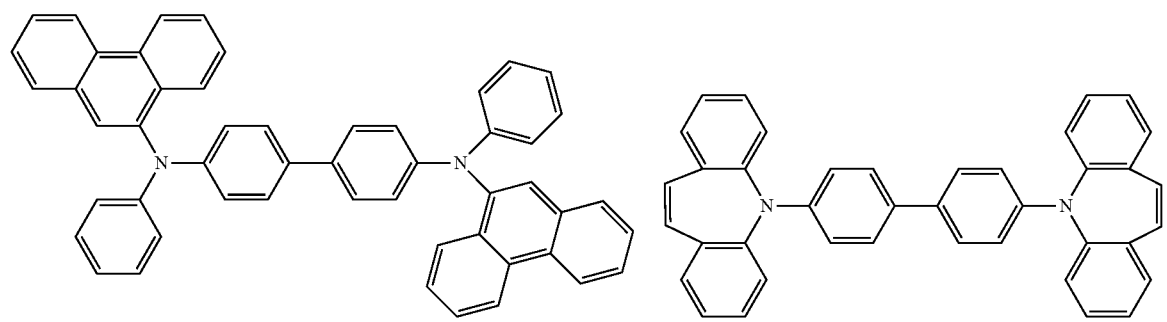

-continued
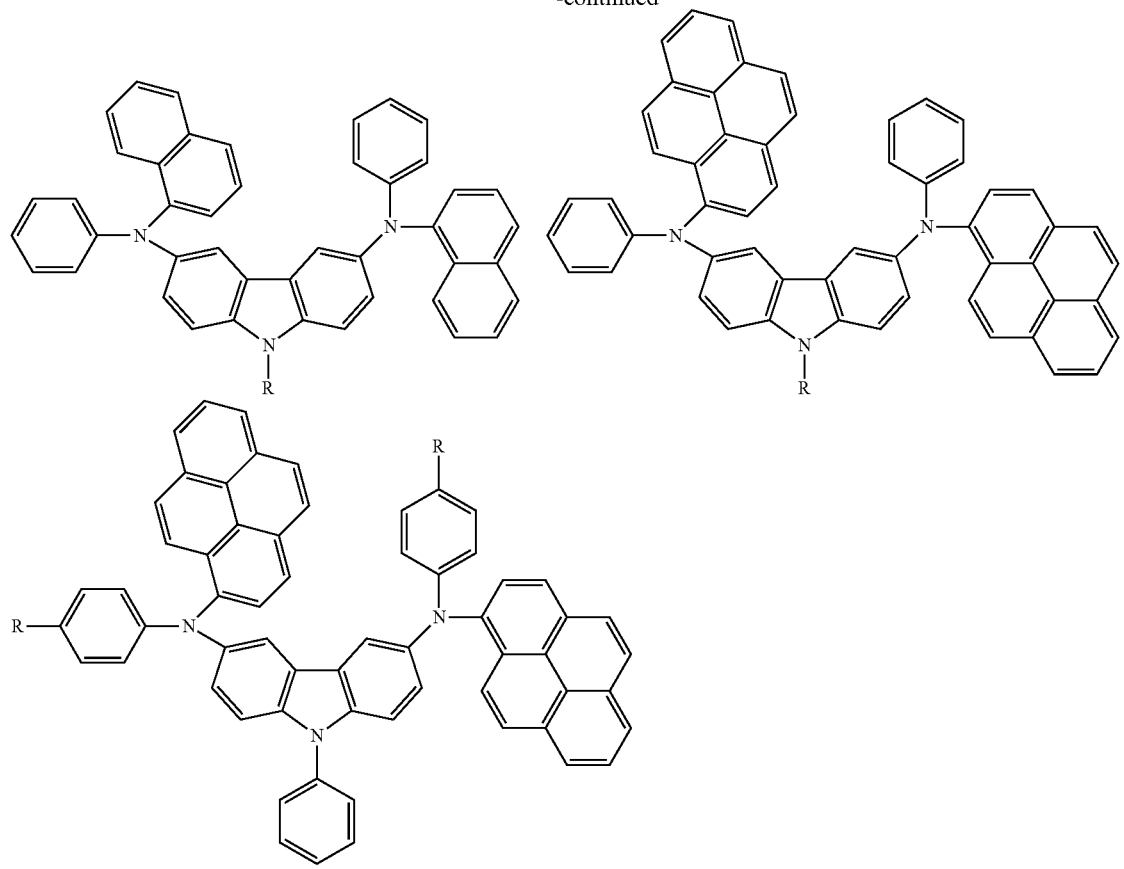
R = alkyl, aryl, alkoxy, aryloxy, 9,9'-dialkylfluorene
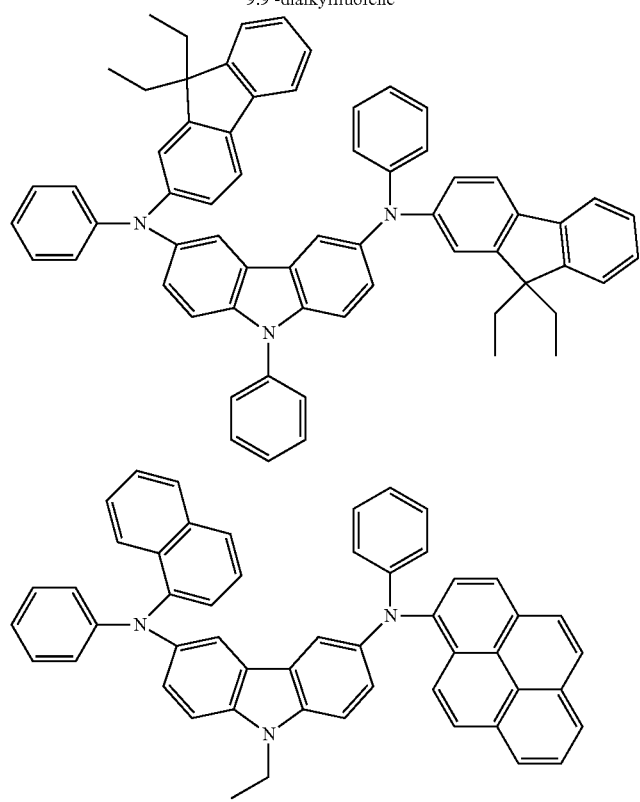

-continued
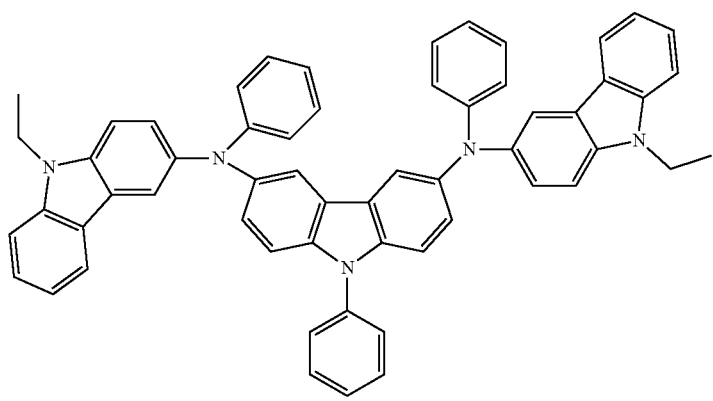
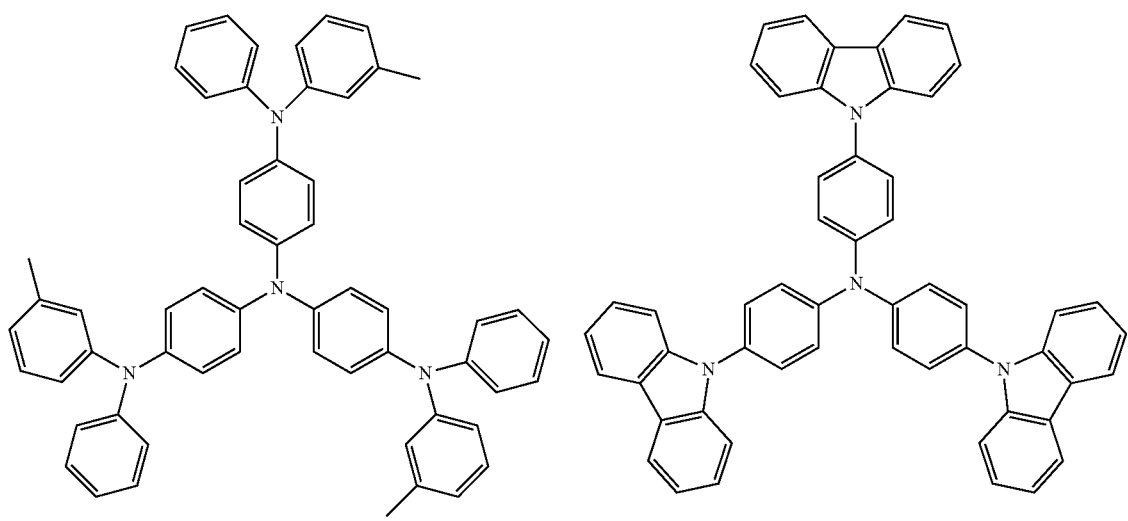
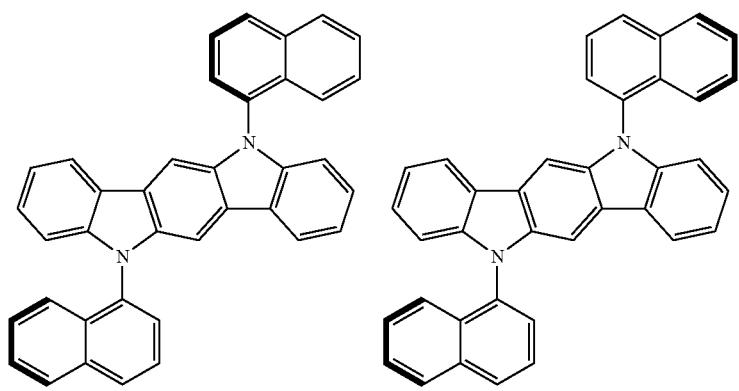

-continued
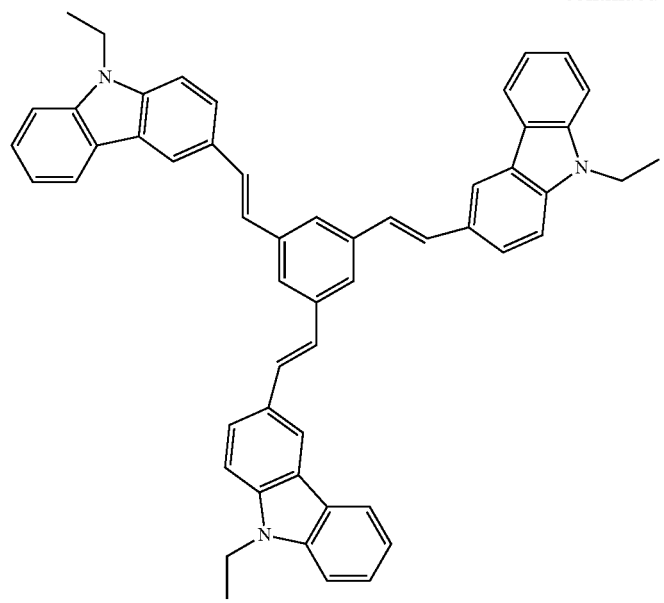
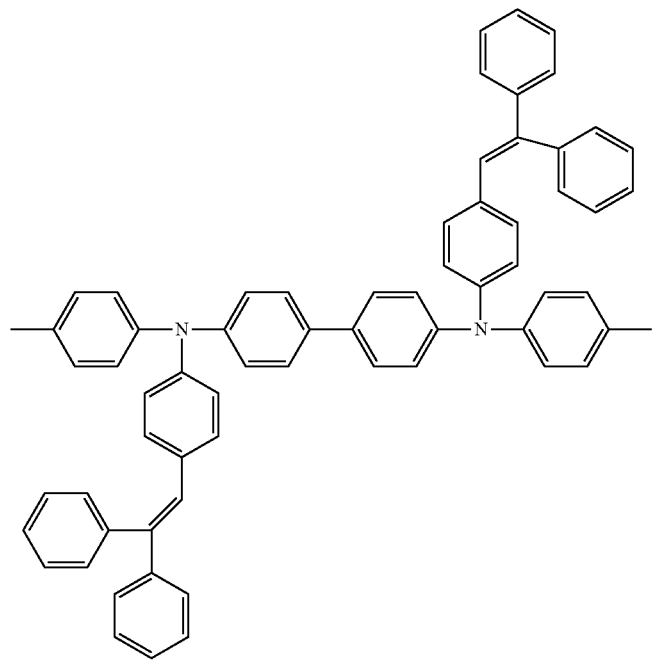
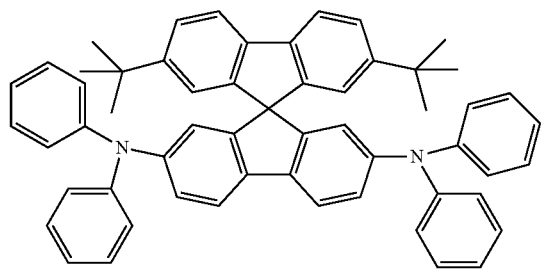
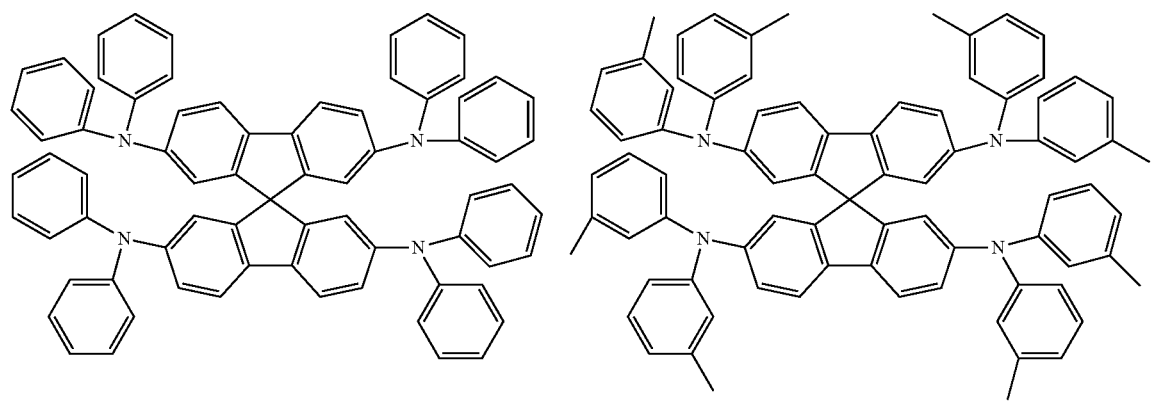

-continued
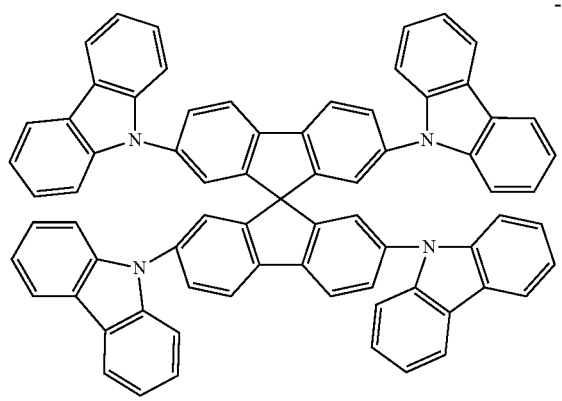
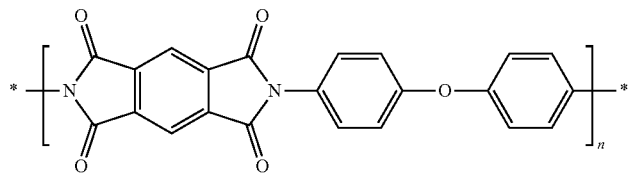
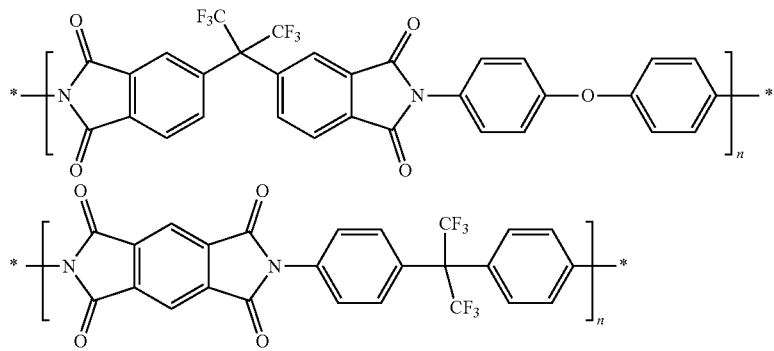
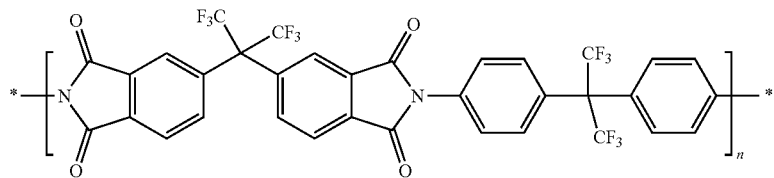
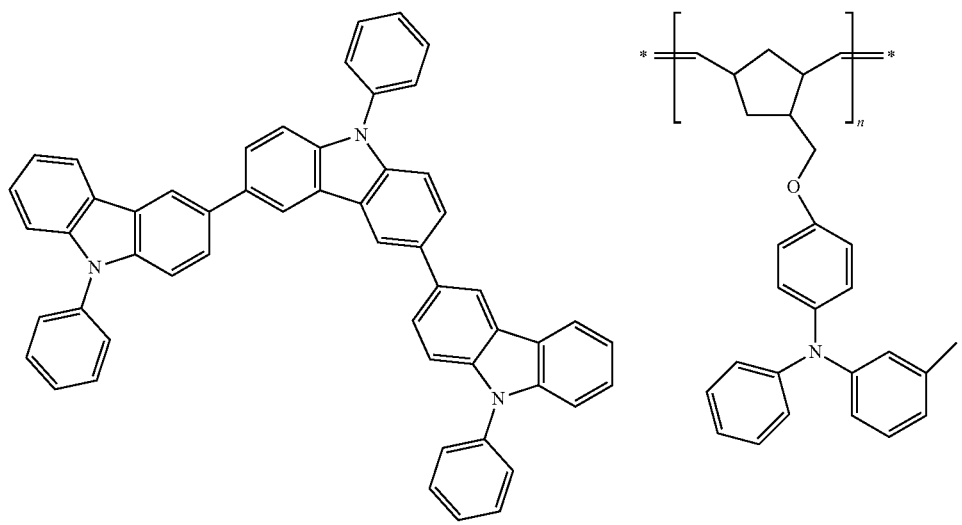

-continued
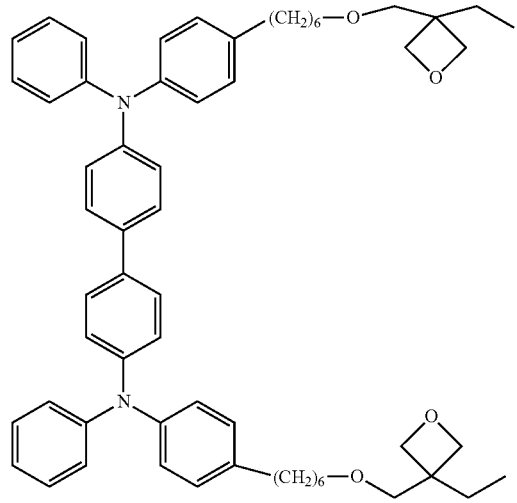
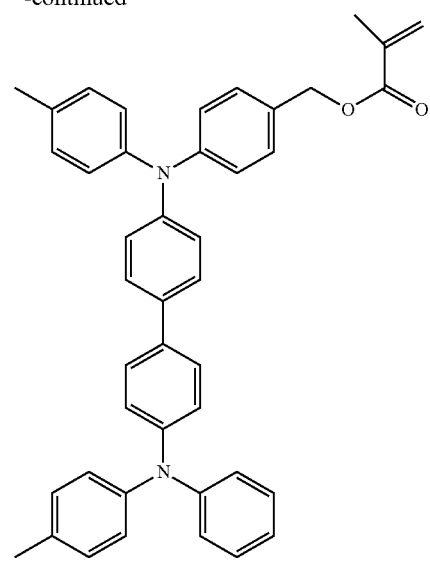
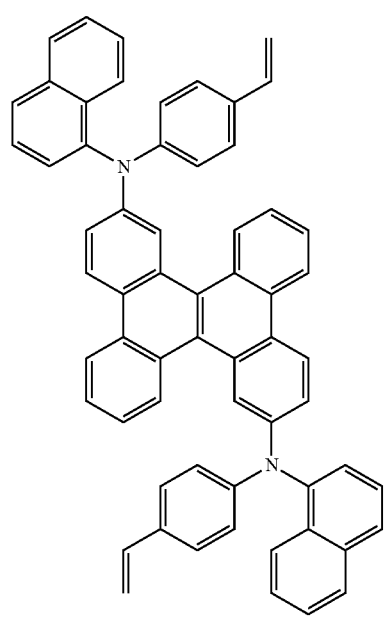
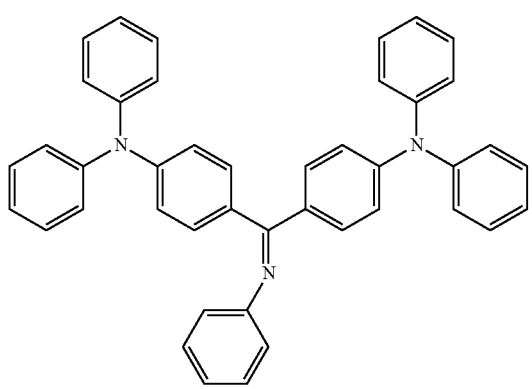
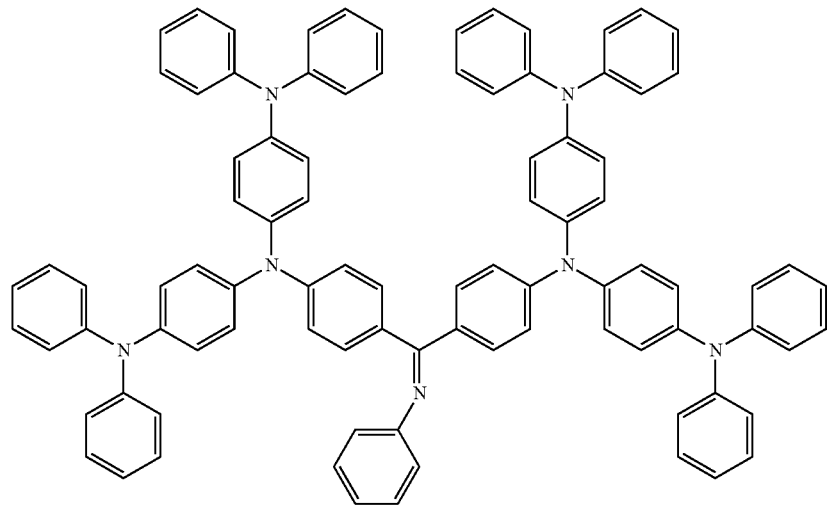

-continued
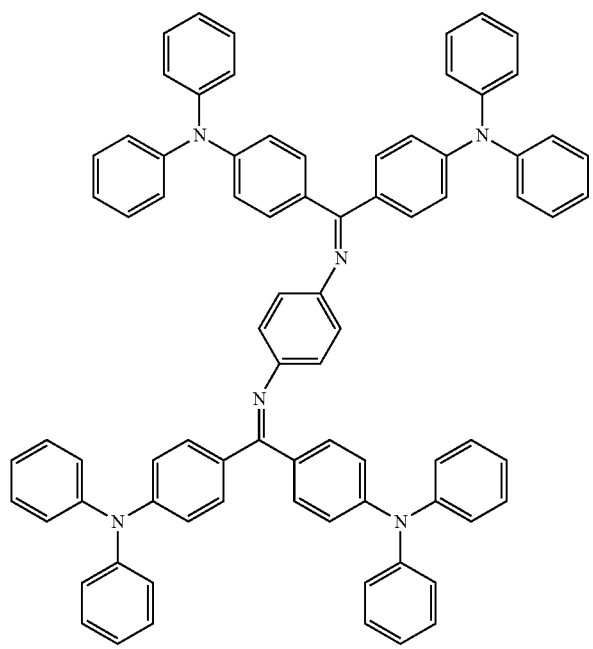
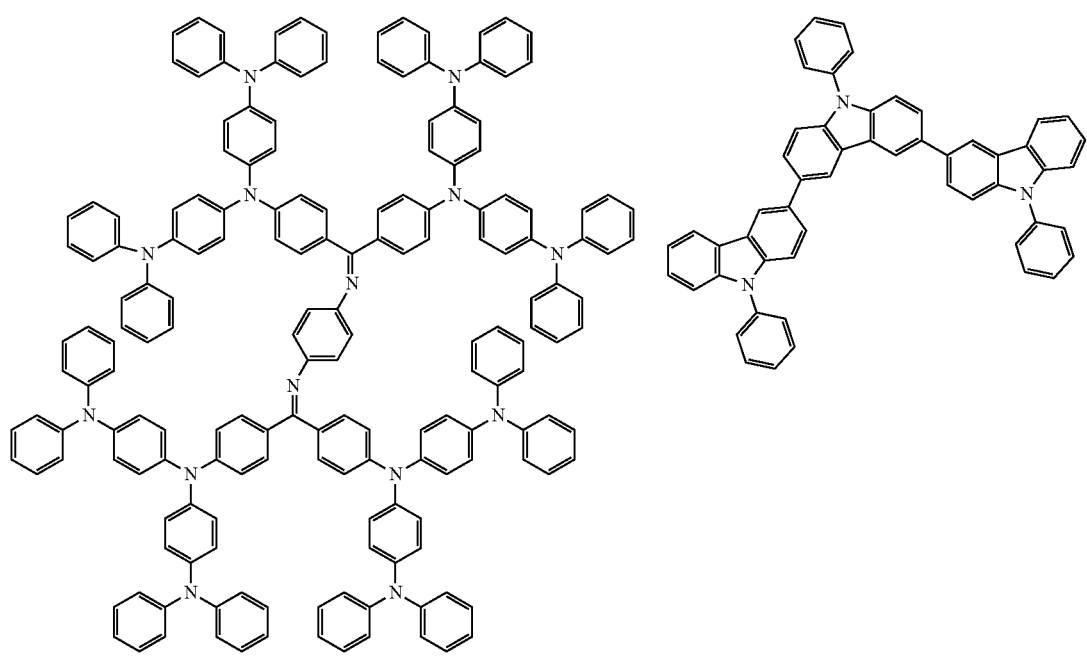

Next, preferred compounds for use as an electron blocking material are mentioned below.
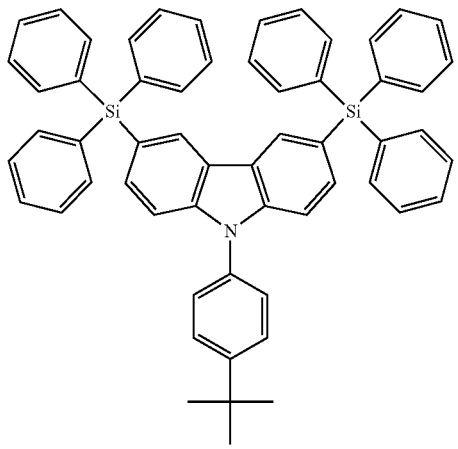
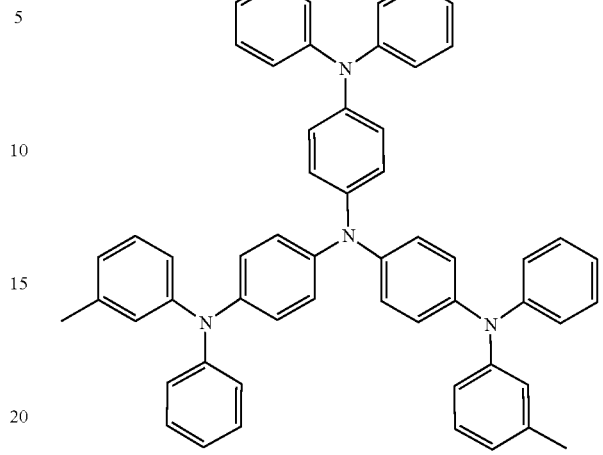
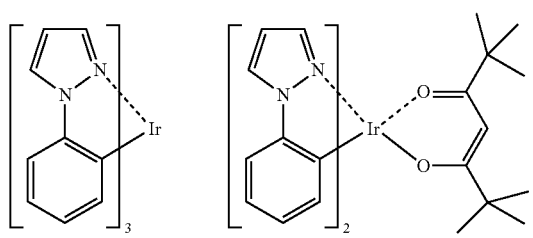
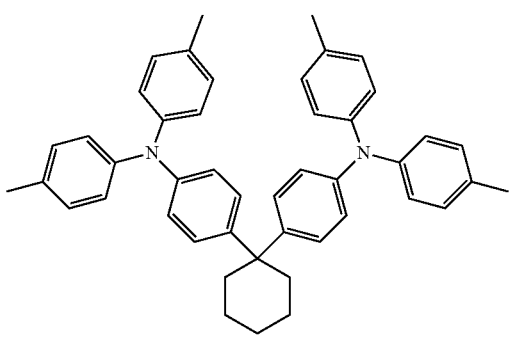
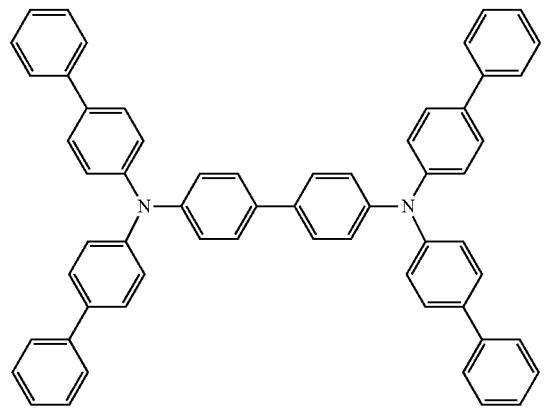
Next, preferred compounds for use as a hole blocking material are mentioned below.
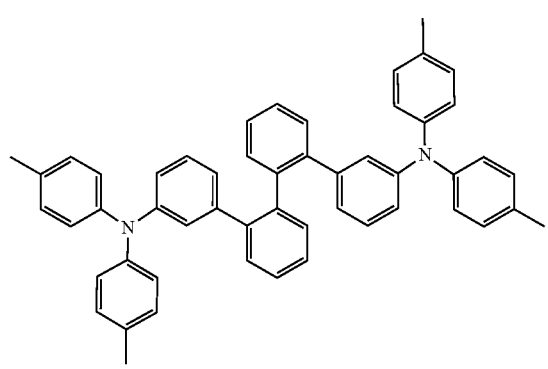
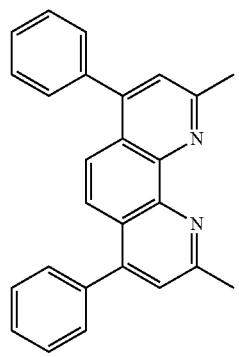

73
-continued
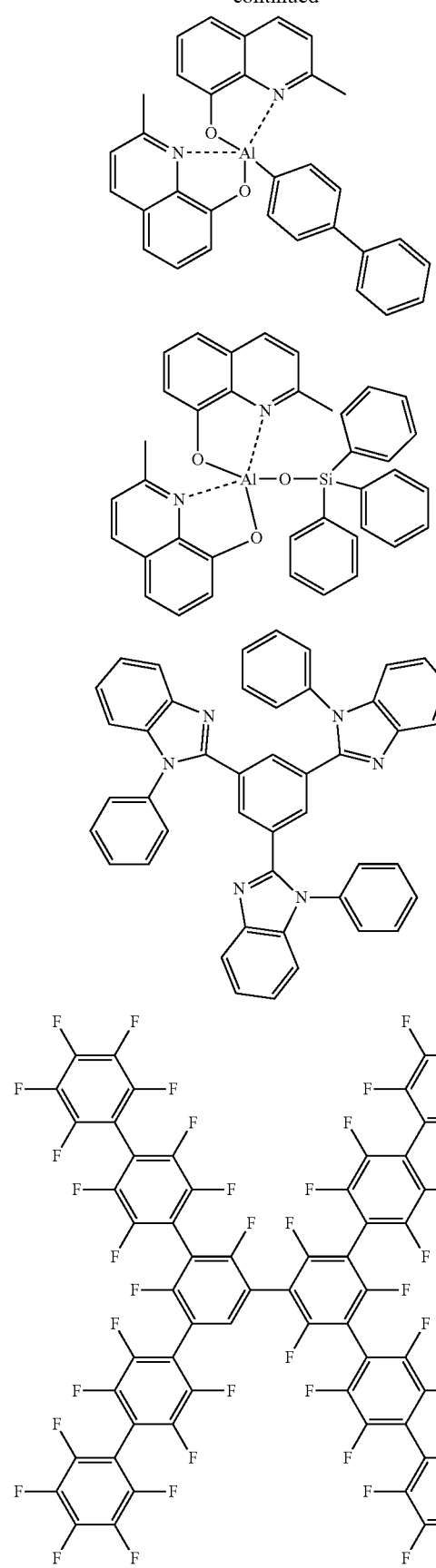
74
-continued
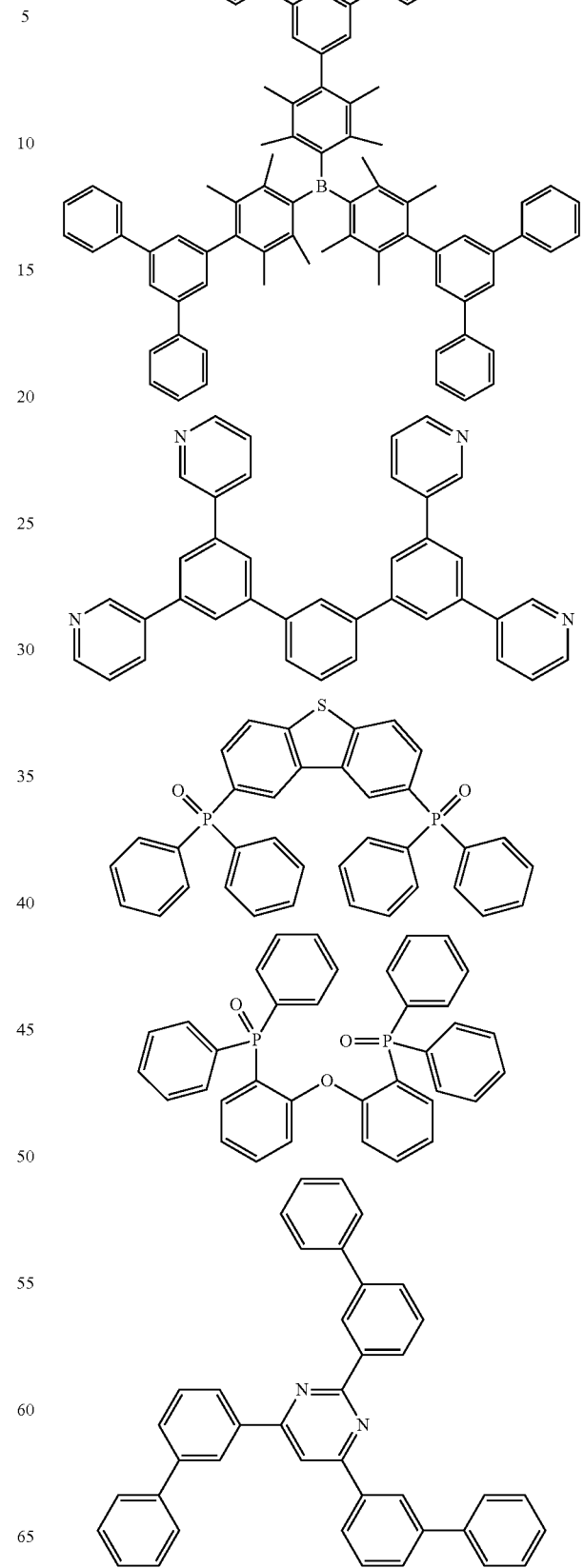

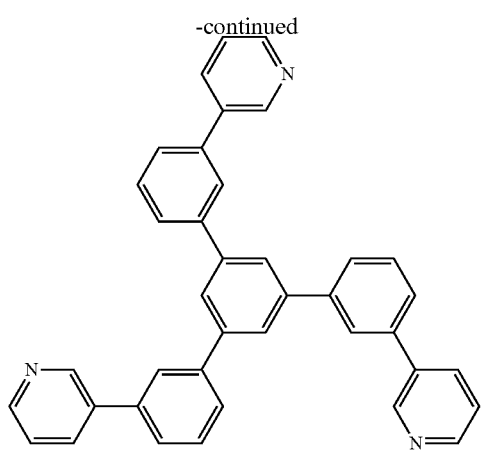
Next, preferred compounds for use as an electron transport material are mentioned below.
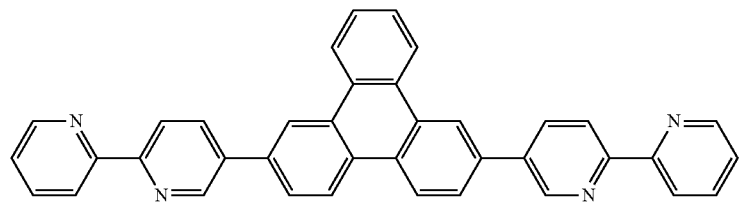
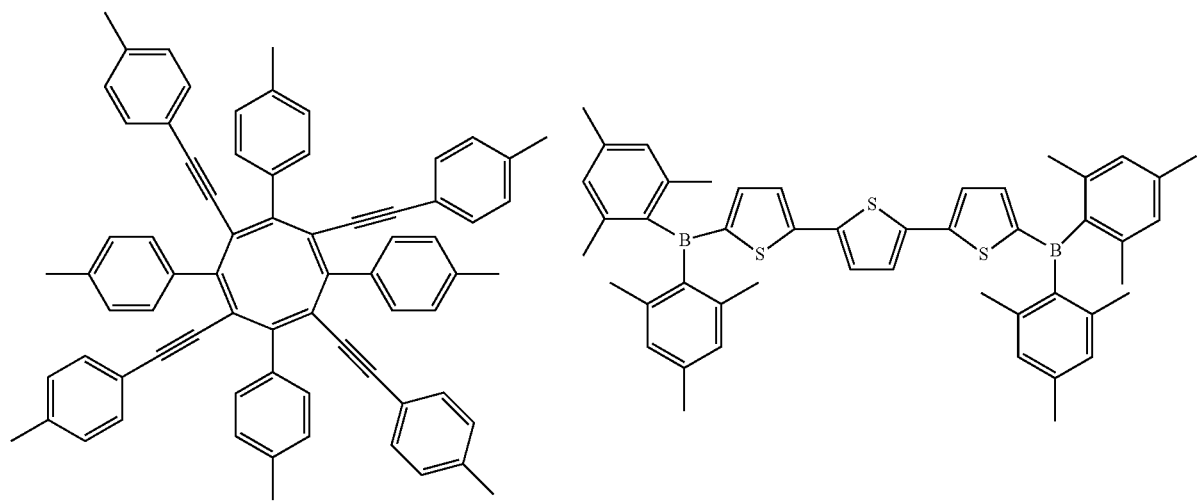
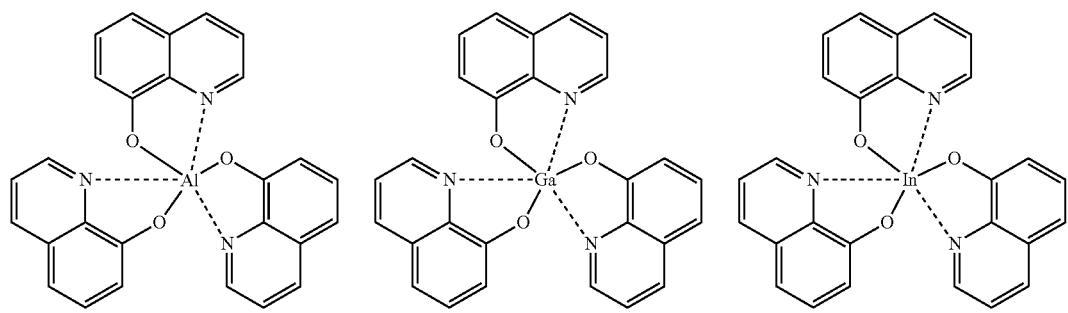

77
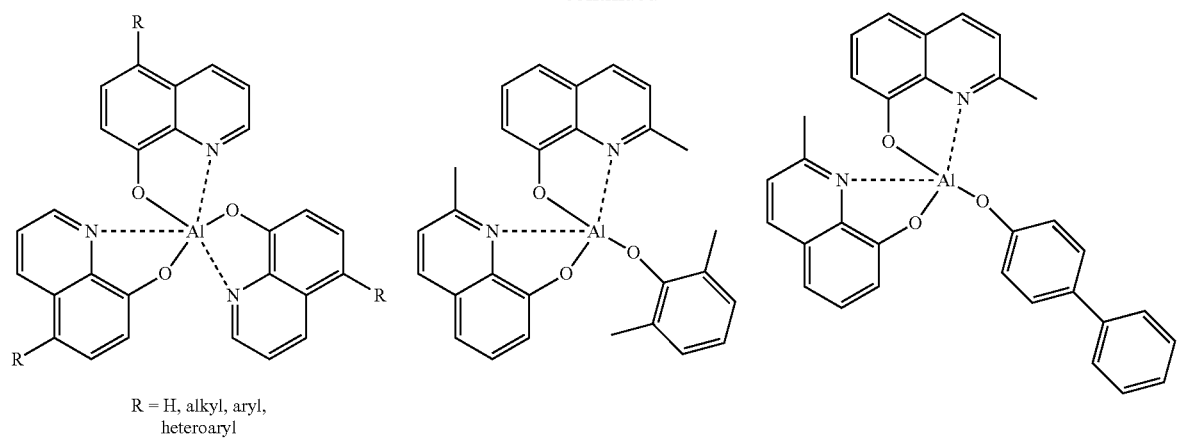
R = H, alkyl, aryl, heteroaryl
78
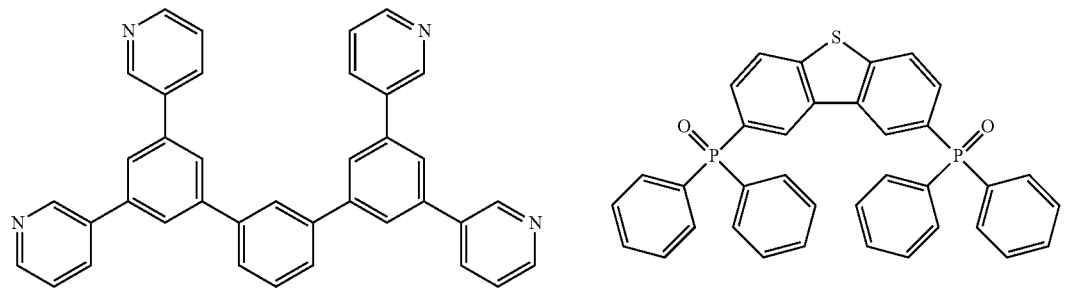
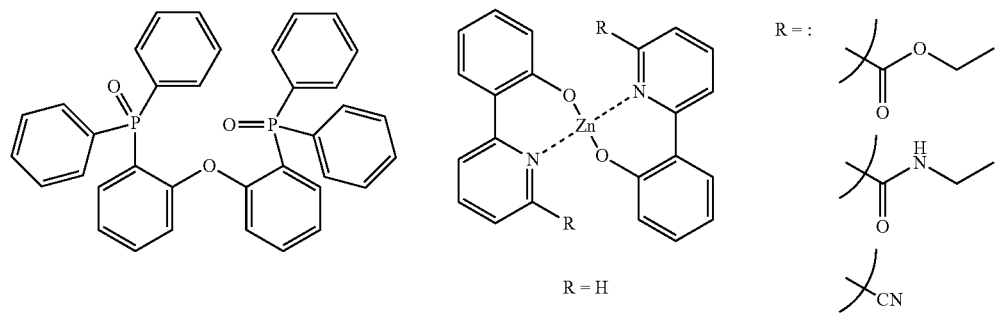
R = H
R = :
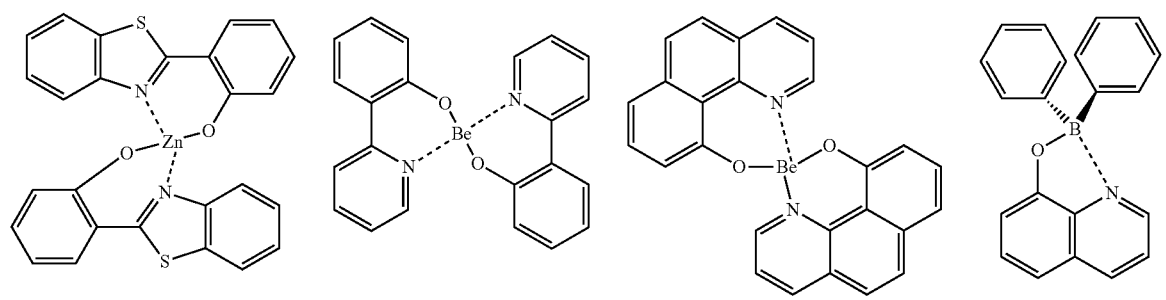

-continued
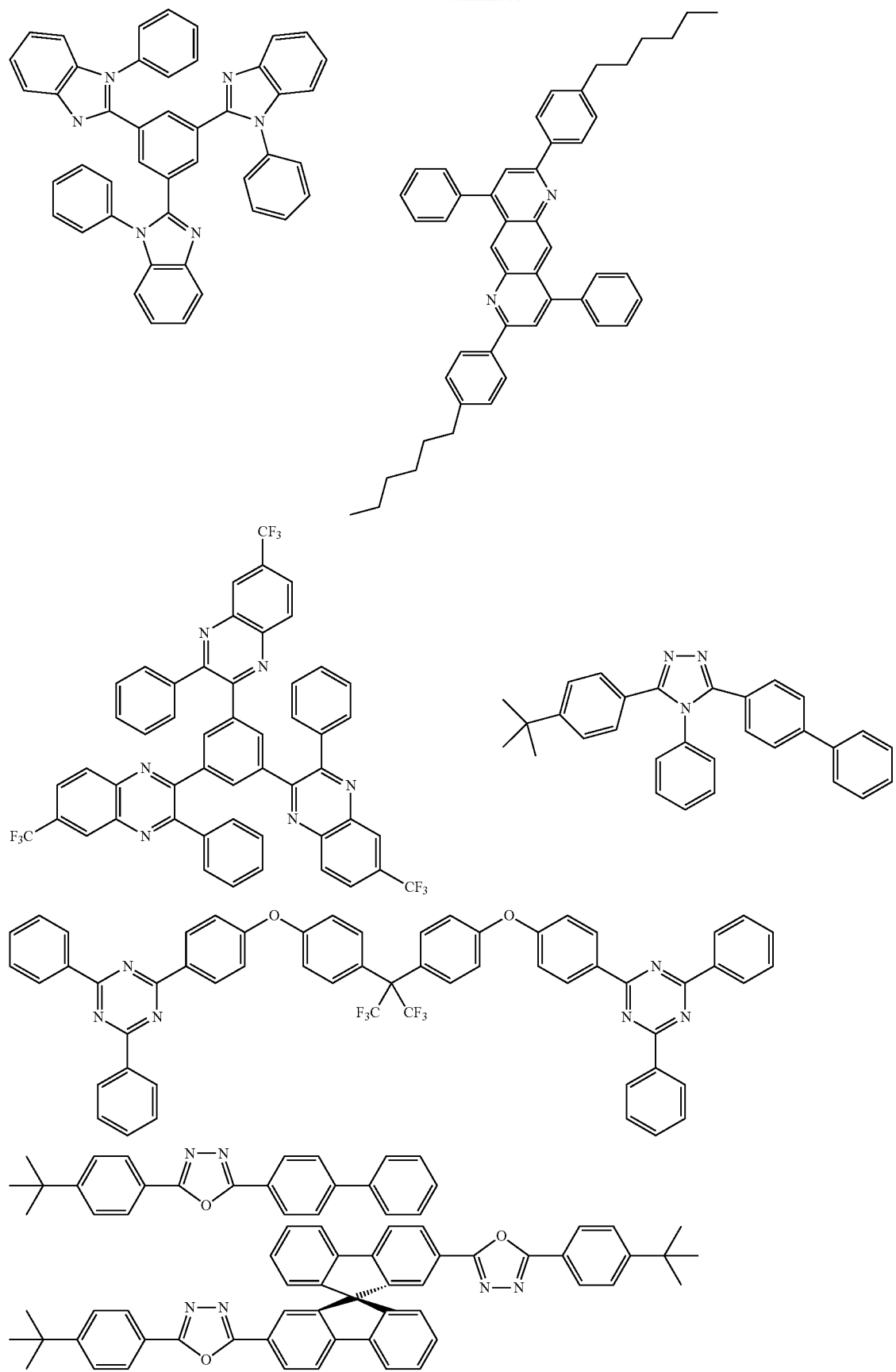

-continued
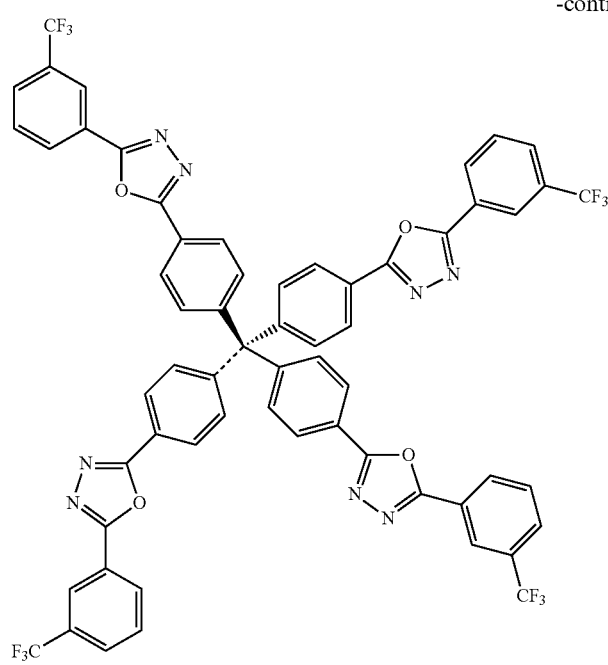
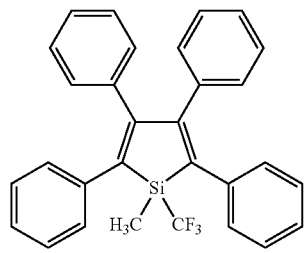
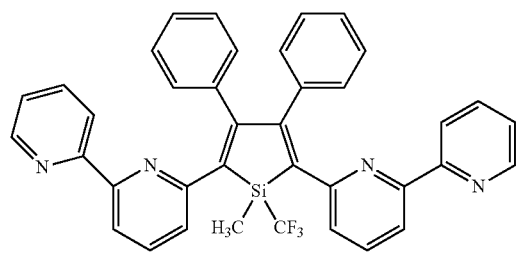
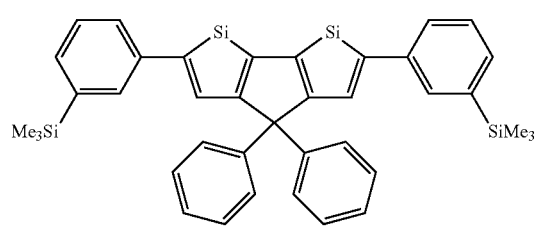
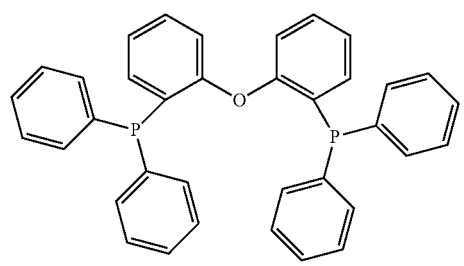
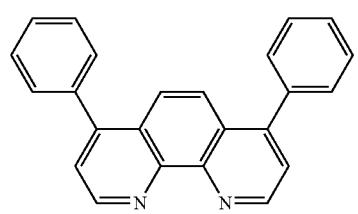
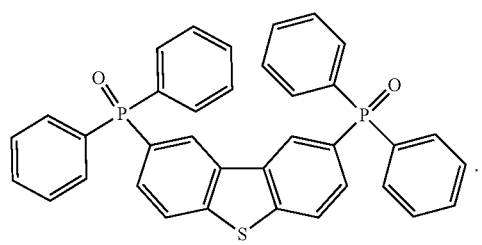 [SMILES: O=P(c1ccccc1)(c1ccccc1)c1ccc2sc3ccc(P(=O)(c4ccccc4)c4ccccc4)cc3c2c1]

Next, preferred compounds for use as an electron injection material are mentioned below.

LiF, CsF

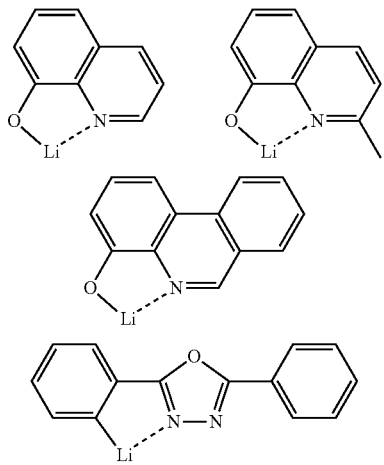

Further, preferred compounds for use as additional materials are mentioned below. For example, these are considered to be added as a stabilization material.

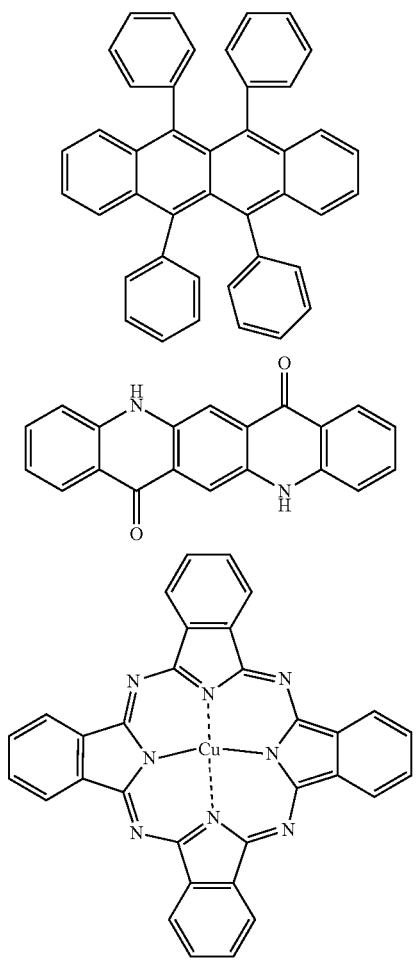

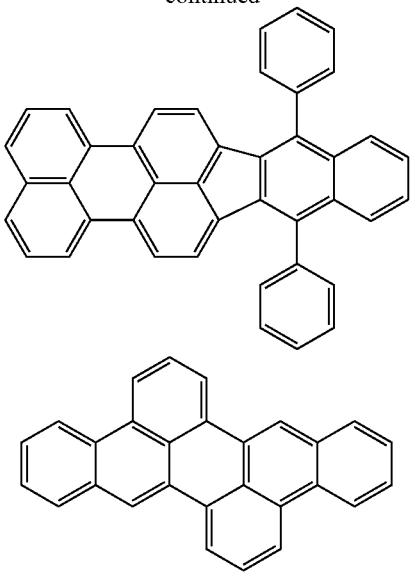

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with a normal organic compound such as the compound of the present invention at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the present invention using a compound capable of emitting delayed fluorescence and capable of undergoing intramolecular hydron transfer in a light-emitting layer, an organic light-emitting device having a markedly improved light emission efficiency can be obtained. The organic light-emitting device such as the organic electroluminescent device of the present invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

In addition, the organic light-emitting device of the present invention may also be an organic light-emitting transistor. An organic light-emitting transistor is, for example, so configured that a gate electrode is layered on an active layer serving also as a light-emitting layer, via a gate insulation layer, and a source electrode and a drain electrode are connected to the active layer. Using the compound capable of emitting delayed fluorescence and capable of undergoing intramolecular hydron transfer as the active layer of such an organic light-emitting transistor, an organic light-emitting transistor excellent both in carrier mobility and emission performance can be realized.

EXAMPLES

The features of the present invention will be described more specifically with reference to Examples given below. The materials, processes, procedures and the like shown below may be appropriately modified unless they deviate from the substance of the invention. Accordingly, the scope of the invention is not construed as being limited to the specific examples shown below. The light emission characteristics were evaluated using a source meter (2400 Series, produced by Keithley Instruments Inc.), an external quantum efficiency measuring system (Model C9920-12, produced by Hamamatsu Photonics K.K.), an optical spectrometer (Model PMA-12, produced by Hamamatsu Photonics K.K.), a fluorescent spectrophotometer (Model Fluoromax-4, produced by HORIBA, Ltd.), an absolute PL quantum yield measuring system (Model Quantaurus-QY, produced by Hamamatsu Photonics K.K.), a small-size fluorescent lifetime measuring system (Model Quantaurus-Tau, produced by Hamamatsu Photonics K.K.), and a streak camera (Model C4334, produced by Hamamatsu Photonics K.K.).

In the following, "instantaneous fluorescence" means fluorescence having an emission lifetime of less than 50 ns, and "delayed fluorescence" means fluorescence having an emission lifetime of 50 ns or more.

The following compound 1 used in each Example was synthesized using a synthesis method described in Dyes Pigments 1990, 12, 301. This compound has a melting point higher than 500° C. and has a sublimation temperature at 1 Pa of higher than 290° C. In heating the compound from room temperature, the weight loss thereof reached 5% at 466° C., that is, the compound is fairly thermally stable. The compound did not show any distinct glass transition temperature (Tg) at 300° C. or lower. H in the structural formula of the following compound 1 is a light hydrogen atom ($^1H$).

Compound 1

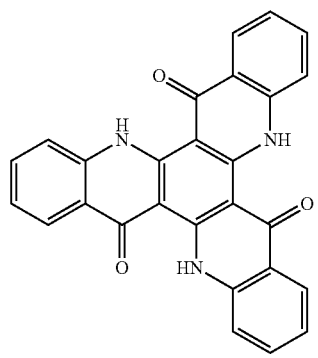

[Production and Evaluation of Organic Photoluminescent Device Using Compound 1]

Example 1

The compound 1 was dissolved in dimethylformamide, tetrahydrofuran or toluene to prepare solutions thereof (concentration $10^{-5}$ mol/L).

According to a sublimation method, a single crystal of the compound 1 was formed to be an organic photoluminescent device. In X-ray structural analysis, all the atoms of the resultant crystal were in one and the same plane, RMS (root-mean-square) of the other atoms than $^1H$ was 0.036 angstroms, and the compound had high planarity.

According to a vacuum evaporation method, a thin film of the compound 1 (hereinafter referred to as "single film") was formed on a quartz substrate under the condition of a vacuum degree of $10^{-3}$ Pa or less, in a thickness of 50 to 100 nm to be an organic photoluminescent device.

Apart from this and according to a vacuum evaporation method, the compound 1 and DPEPO were vapor-deposited from different evaporation sources on a quartz substrate under the condition of a vacuum degree of $10^{-3}$ Pa or less to form a thin film thereon having a concentration of the compound 1 of 6 to 15% by mass (hereinafter referred to as "doped film") in a thickness of 50 to 100 nm, thereby to be an organic photoluminescent device.

In the following, the solutions, the single crystal, the single film and the doped film with the compound 1 produced herein are collectively referred to as "measurement samples".

Results of measurement of absorption spectra (for the single crystal, an excitation spectrum thereof at 530 nm) and emission spectra with a 330-nm excitation light of the dimethylformamide solution (DMF solution), the tetrahydrofuran solution (THF solution), the toluene solution (Toluene solution) and the single crystal of the compound 1, as well as an absorption spectrum of the compound 1 obtained through calculation in density functional theory (DFT), and an emission spectrum of a hydron-transferred form of the compound 1 represented by the formula (A-1) also obtained through calculation in density functional theory (DFT) are shown in FIG. 2; and the photoluminescence quantum yield of each sample measured in air as well as the photoluminescence quantum yield of each solution measured with nitrogen bubbling are shown in Table 1.

Results of measurement of absorption spectra and emission spectra with a 330-nm excitation light of the single film, the doped film and the toluene solution of the compound 1 are shown in FIG. 3; and the photoluminescence quantum yield of each sample measured in air and in an argon atmosphere are shown in Table 2.

TABLE 1

| | Photoluminescence Quantum Yield | |
|---|---|---|
| Measurement Sample | in air | with nitrogen bubbling |
| DMF Solution of Compound 1 | 14.1% | 15.4% |
| THF Solution of Compound 1 | 23.7% | 31.7% |
| Toluene Solution of Compound 1 | 37.2% | 58.5% |
| Single Crystal of Compound 1 | 61.5% | — |

TABLE 2

| Measurement Sample | Photoluminescence Quantum Yield | |
|---|---|---|
| | in air | with nitrogen bubbling |
| Single Film of Compound 1 | 21.2% | 21.3% |
| Doped Film with Compound 1 | 44.1% | 57.0% |

As in FIGS. 2 and 3, all the measurement samples had an absorption maximum wavelength in a range of 250 to 350 nm, and an emission maximum wavelength in a range of 500 to 600 nm, that is, the Stokes shift thereof was more than 100 nm. In addition, the absorption-emission spectrum of each measurement sample well coincided with the absorption-emission spectrum thereof obtained in DFT calculation. These confirm that the compound 1 is a compound that undergoes intramolecular hydron transfer. In addition, as in Tables 1 and 2, the measurement samples containing the compound 1 all had a high quantum yield.

On the other hand, a toluene solution of a mixture of the following three compounds each having a structure shown below, which differ from the compound 1 in that $^1$H of the amino group of the compound 1 is substituted with a methyl group, was measured similarly. As a result, the emission maximum wavelength of the emission spectrum of the toluene solution showed a large Stokes shift at around 550 nm and a small Stokes shift at 400 nm or less. These confirm that, in the compound 1, $^1$H of the amino group undergoes hydron transfer, and owing to the hydron transfer, the compound 1 emits light.

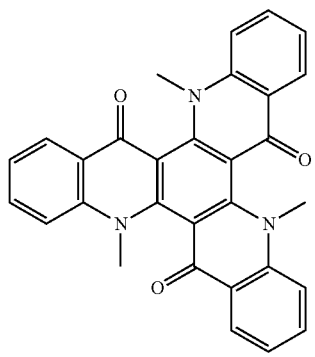

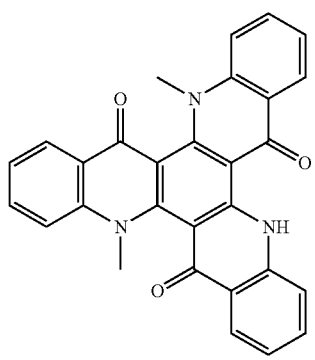

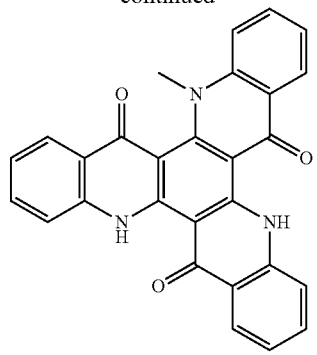

FIG. 4 shows a transient decay curve in light emission of the toluene solution (Toluene solution) of the compound 1, measured with nitrogen bubbling; FIG. 5 shows a transient decay curve in light emission of the tetrahydrofuran solution (THF solution) of the compound 1, measured with nitrogen bubbling; FIG. 6 shows a transient decay curve in light emission of the single crystal of the compound 1. Here, the transient decay curve in light emission was measured using a 340-nm excitation light. "IRF" in FIGS. 4 and 5 shows an instrumental response function.

FIGS. 4 to 6 confirm delayed fluorescence whose emission intensity gradually decays with the lapse of time. Here, the light emission lifetime of the toluene solution was 6.9 ns in instantaneous fluorescence and 74 μs in delayed fluorescence; the light emission lifetime of the tetrahydrofuran solution was 4.6 ns in instantaneous fluorescence and 90 μs in delayed fluorescence; and the light emission lifetime of the single crystal was 8.2 ns in instantaneous fluorescence and 1.2 μs in delayed fluorescence.

For comparison, using a comparative compound 1 having the following structure, various solutions and a single crystal were produced in the same manner as above, and the absorption emission spectra and the transient decay curve in light emission thereof were measured. However, these did not show delayed fluorescence, and the light emission thereof was weak. H in the structural formula of the following comparative compound 1 is a light hydrogen atom ($^1$H).

Comparative Compound 1

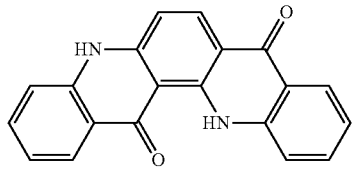

FIG. 7 shows a transient decay curve in light emission of a doped film with the compound 1, measured using a 337-nm excitation light (nitrogen gas laser) at a temperature of 6 K to 300 K; FIG. 8 shows light emission spectra of instantaneous light emission at 6 K, instantaneous light emission at 300 K and delayed light emission thereof at 300 K; and FIG. 9 is a graph of light emission intensity in irradiation with a laser light at a different intensity, as plotted relative to the laser light intensity.

FIG. 7 is referred to, in which the light emission lifetime is longer with the increase in the temperature, indicating a temperature dependency peculiar to a thermal activation type delayed fluorescent material. The inclination of the plotting in FIG. 9 is 1, which confirms that the compound 1 is not a delayed fluorescent material with triplet-triplet annihilation but a thermal activation type delayed fluorescent material.

FIG. 10 is a graph of a photoluminescence quantum efficiency of total emission (instantaneous fluorescence+delayed fluorescence), instantaneous fluorescence and delayed fluorescence of a doped film with the compound 1 measured at different temperature conditions, as plotted relative to the temperature. At 6 K, instantaneous fluorescence alone was observed but delayed fluorescence was not observed. FIG. 11 is a graph (Arrhenius plot) of a logarithm of the rate constant $k_{RISC}$ of reverse intersystem crossing, as plotted relative to the reciprocal of the absolute temperature.

The rate constant $k_{RISC}$ of reverse intersystem crossing of the compound 1 at room temperature is $3 \times 10^3$ s$^{-1}$, and $\Delta E_{ST}$ of the compound 1 derived from the Arrhenius plot in FIG. 11 was 200 meV.

FIG. 12 shows a transient decay curve in light emission of the single film of the compound 1, measured using a 337-nm excitation light at a temperature of 6 K to 300 K; and FIG. 13 shows light emission spectra of instantaneous light emission thereof observed at 6 K, instantaneous light emission thereof at 300 K and delayed light emission thereof at 300 K.

FIG. 12 confirms a temperature dependency of the single film of the compound 1 peculiar to a thermal activation type delayed fluorescent material. For determining the HOMO level and the LUMO level of the compound 1, a thin film of the compound 1 was provided on an indium tin oxide (ITO) electrode. Using an Ag/Ag$^+$ electrode, the thin film was measured and the cyclic voltammogram thereof based on ferrocene/ferrocenium (Fc/Fc$^+$) is shown in FIG. 14. FIG. 15 is a graph showing an UV irradiation energy dependency of (photoelectric emission yield)$^{0.5}$ of the thin film of the compound 1, measured using a photoelectron spectrometer (AC-3, produced by Riken Keiki Co., Ltd.). As in FIGS. 14 and 15, |HOMO| of the compound 1 was about 6.0 eV, and |LUMO| thereof was about 3.0 eV, and the values of the HOMO level and the LUMO level obtained from each drawing were almost coincident with each other.

[Production and Evaluation of Organic Electroluminescent Device Using Compound 1]

Layer configurations of the organic electroluminescent devices produced in the following Examples 2 to 5 are shown in Table 2. In the column of layer configuration in Table 2, "/" indicates a boundary between the adjacent layers, indicating that, via the boundary "/", the layer on the light-hand side is layered on the layer on the left-hand side.

TABLE 3

| Example No. | Layer Configuration |
|---|---|
| Example 2 | ITO (100 nm)/TAPC (30 nm)/TCTA (20 nm)/CzSi (10 nm)/10 wt % compound 1, PPT (30 nm)/PPT (40 nm)/LiF (0.8 nm)/Al (100 nm) |
| Example 3 | ITO (100 nm)/NPD (30 nm)/TCTA (20 nm)/CzSi (10 nm)/10 wt % compound 1, PPT (30 nm)/PPT (40 nm)/LiF (0.8 nm)/Al (100 nm) |
| Example 4 | ITO (100 nm)/NPD (35 nm)/mCP (10 nm)/10 wt % compound 1, PPT (30 nm)/PPT (40 nm)/LiF (0.8 nm)/Al (100 nm) |
| Example 5 | ITO (100 nm)/Tris-PCz (40 nm)/7 wt % compound 1, mCBP (30 nm)/T2T (10 nm)/Alq3 (40 nm)/LiF (0.8 nm)/Al (100 nm) |

Example 2

On a glass substrate with an anode of indium tin oxide (ITO) having a thickness of 100 nm formed thereon, thin films were layered according to a vacuum vapor deposition method under a vacuum degree of 10$^{-4}$ Pa. First, on ITO, TAPC was formed in a thickness of 30 nm. Subsequently, TCTA was formed thereon in a thickness of 20 nm, and further on this, CzSi was formed in a thickness of 10 nm. Next, the compound 1 and PPT were co-deposited from different evaporation sources to form a layer having a thickness of 30 nm as a light-emitting layer. At this time, the concentration of the compound 1 was 10% by weight. Next, PPT was formed in a thickness of 40 nm. Further, lithium fluoride (LiF) was vapor-deposited in a thickness of 0.8 nm, and then aluminum (Al) was vapor-deposited thereon in a thickness of 100 nm to form a cathode, thereby producing an organic electroluminescent device.

FIG. 16 shows light emission spectra of the produced organic electroluminescent device measured at a voltage of 6 V, 9 V and 12 V; FIG. 17 shows a current density-voltage characteristic thereof; and FIG. 18 shows an external quantum efficiency (EQE)-current density characteristic thereof. The organic electroluminescent device using the compound 1 as a light-emitting material attained a high external quantum efficiency of 13.7%.

Example 3

An organic electroluminescent device was produced in the same manner as in Example 2, except that NPD was formed in a thickness of 30 nm on ITO in place of forming TAPC in a thickness of 30 nm thereon.

FIG. 19 shows light emission spectra of the produced organic electroluminescent device measured at a voltage of 6 V, 9 V and 12 V; FIG. 20 shows a current density-voltage characteristic thereof; and FIG. 21 shows an external quantum efficiency (EQE)-current density characteristic thereof. The organic electroluminescent device using the compound 1 as a light-emitting material attained a high external quantum efficiency of 9.4%.

Example 4

On a glass substrate with an anode of indium tin oxide (ITO) having a thickness of 100 nm formed thereon, thin films were layered according to a vacuum vapor deposition method under the same condition as in Example 1. First, on ITO, NPD was formed in a thickness of 35 nm, and mCP was formed thereon in a thickness of 10 nm. Next, the compound 1 and PPT were co-deposited from different evaporation sources to form a layer having a thickness of 30 nm as a light-emitting layer. At this time, the concentration of the compound 1 was 10% by weight. Next, PPT was formed in a thickness of 40 nm. Further, lithium fluoride (LiF) was vapor-deposited in a thickness of 0.8 nm, and then aluminum (Al) was vapor-deposited thereon in a thickness of 100 nm to form a cathode, thereby producing an organic electroluminescent device.

FIG. 22 shows light emission spectra of the produced organic electroluminescent device measured at a voltage of 6 V, 9 V and 12 V; FIG. 23 shows a current density-voltage characteristic thereof; and FIG. 24 shows an external quantum efficiency (EQE)-current density characteristic thereof. The organic electroluminescent device using the compound 1 as a light-emitting material attained a high external quantum efficiency of 5.7%.

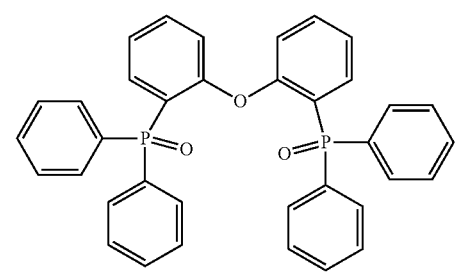
DPEPO
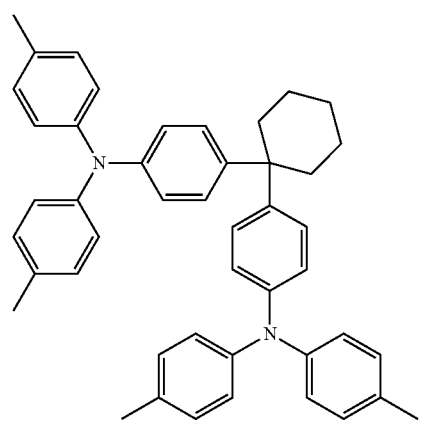
TAPC
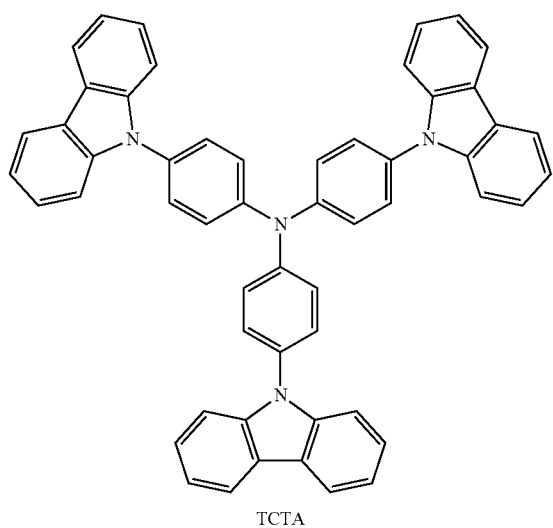
TCTA
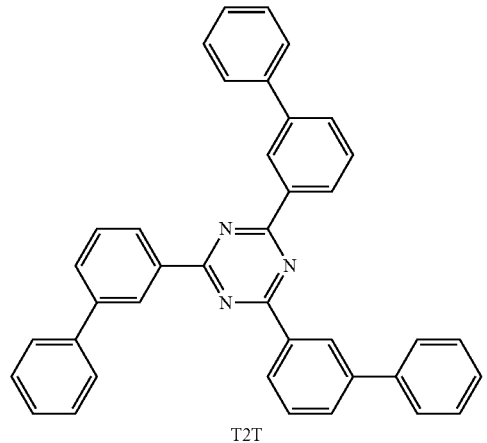
T2T
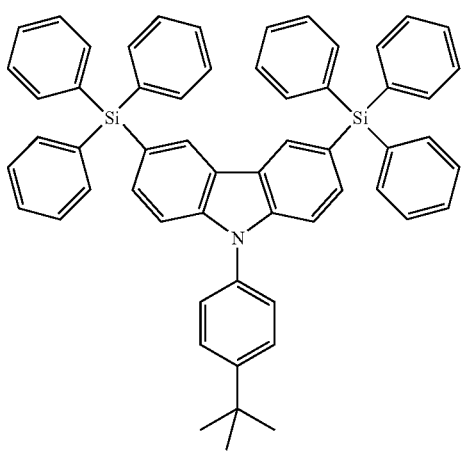
CzSi
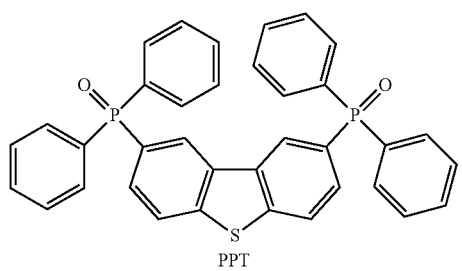
PPT
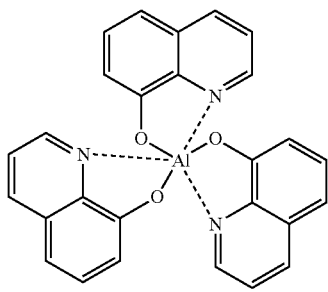
Alq3
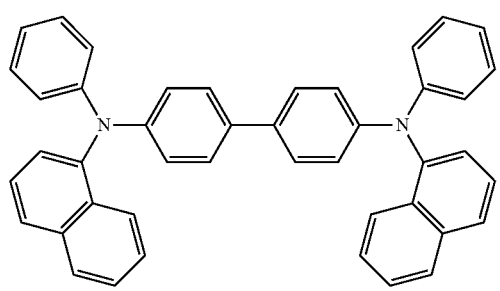
NPD
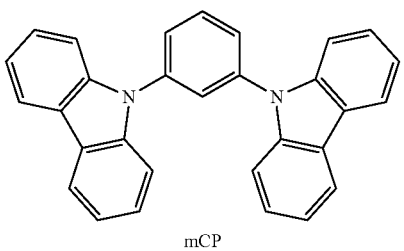
mCP

93
-continued

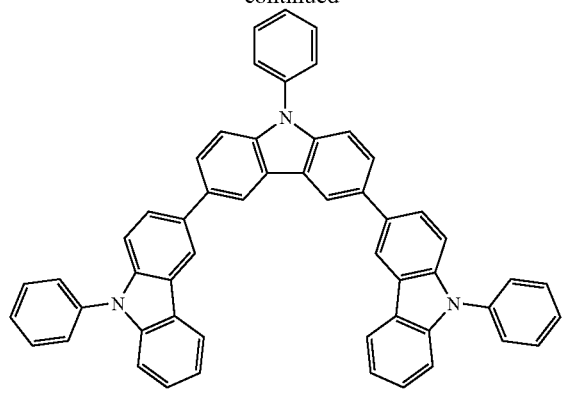

Tris-PCz

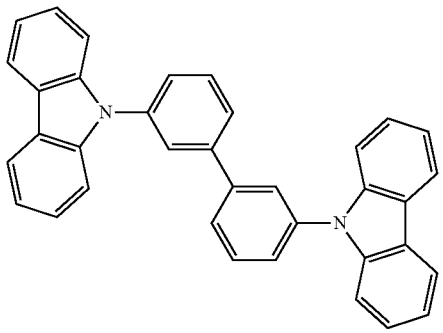

mCBP

INDUSTRIAL APPLICABILITY

The compound for use in the organic light-emitting device of the present invention emits delayed fluorescence even though not having a D-A type structure in a ground state thereof, and exhibits a sufficiently high quantum yield enough for practical use as a device material. Accordingly, the present invention can realize an organic light-emitting device having a high light emission efficiency and can realize a delayed fluorescent material having a broad latitude in molecular planning of a delayed fluorescent material, having high planarity and having good stability or alignability. Consequently, the industrial applicability of the present invention is great.

REFERENCE SIGNS LIST

1 Substrate
2 Anode
3 Hole Injection Layer
4 Hole Transport Layer
5 Light-Emitting Layer
6 Electron Transport Layer
7 Cathode

The invention claimed is:

1. An organic light-emitting device using a compound capable of emitting delayed fluorescence and capable of undergoing intramolecular hydron transfer, wherein the compound is represented by the following general formula (1):

94

General Formula (1)

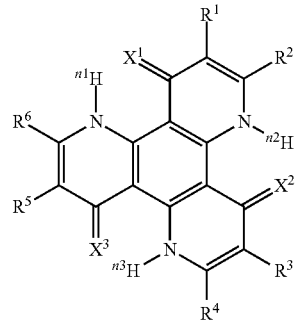

wherein $X^1$ to $X^3$ each independently represent O or S; $R^1$ to $R^6$ each independently represent ″H or a substituent; n, n1 to n3 each independently represent an integer of 1 to 3; $R^1$ and $R^2$, $R^3$ and $R^4$, $R^5$ and $R^6$ each may bond to each other to form a cyclic structure.

2. The organic light-emitting device according to claim 1, wherein $R^1$ and $R^2$, $R^3$ and $R^4$, $R^5$ and $R^6$ in the general formula (1) each bond to each other to form a cyclic structure.

3. The organic light-emitting device according to claim 1, wherein the compound capable of emitting delayed fluorescence and capable of undergoing intramolecular hydron transfer is a compound represented by the following general formula (2):

General Formula (2)

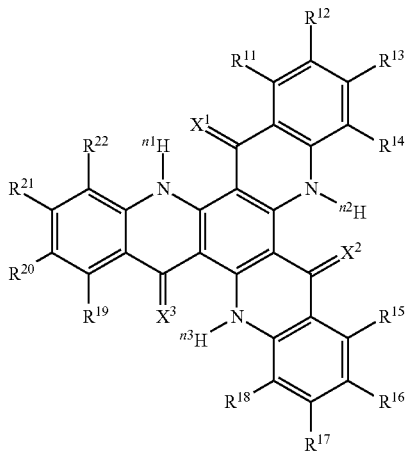

wherein $X^1$ to $X^3$ each independently represent O or S; $R^{11}$ to $R^{22}$ each independently represent ″H or a substituent; n, n1 to n3 each independently represent an integer of 1 to 3; $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, $R^{19}$ and $R^{20}$, $R^{20}$ and $R^{21}$, $R^{21}$ and $R^{22}$ each may bond to each other to form a cyclic structure.

4. The organic light-emitting device according to claim 3, wherein $R^{11}$, $R^{14}R^{15}$, $R^{18}$, $R^{19}$ and $R^{22}$ each are ″H.

5. A light-emitting film comprising a host material and a compound represented by the following general formula (1):

General Formula (1)
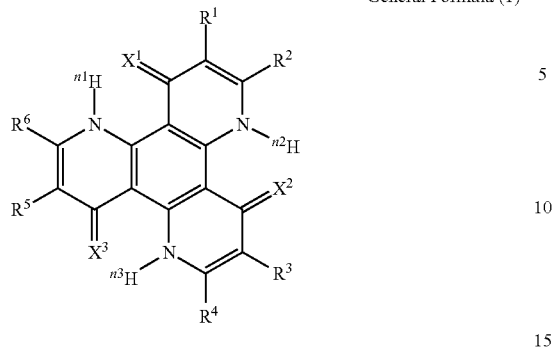
wherein $X^1$ to $X^3$ each independently represent O or S; $R^1$ to $R^6$ each independently represent $^n$H or a substituent; n and n1 to n3 each independently represent an integer of 1 to 3; and $R^1$ and $R^2$, $R^3$ and $R^4$, $R^5$ and $R^6$ each may bond to each other to form a cyclic structure.
* * * * *